US008492400B2

(12) United States Patent
Mudumba et al.

(10) Patent No.: US 8,492,400 B2
(45) Date of Patent: Jul. 23, 2013

(54) STABLE FORMULATIONS, AND METHODS OF THEIR PREPARATION AND USE

(75) Inventors: Sreenivasu Mudumba, Union City, CA (US); Thierry Nivaggioli, Atherton, CA (US); Sudeep Kaur Takhar, Gilroy, CA (US)

(73) Assignee: Santen Pharmaceutical Co., Ltd., Osaka (JP)

( * ) Notice: Subject to any disclaimer, the term of this patent is extended or adjusted under 35 U.S.C. 154(b) by 1395 days.

(21) Appl. No.: 11/704,442

(22) Filed: Feb. 9, 2007

(65) Prior Publication Data

US 2007/0203173 A1    Aug. 30, 2007

Related U.S. Application Data

(60) Provisional application No. 60/772,018, filed on Feb. 9, 2006.

(51) Int. Cl.
*A61K 31/445* (2006.01)

(52) U.S. Cl.
USPC .......................................................... 514/291

(58) Field of Classification Search
USPC .......................................................... 514/291
See application file for complete search history.

(56) References Cited

U.S. PATENT DOCUMENTS

| | | | |
|---|---|---|---|
| 3,416,530 A | 12/1968 | Ness | |
| 3,630,200 A | 12/1971 | Higuchi | |
| 3,828,777 A | 8/1974 | Ness | |
| 3,914,402 A | 10/1975 | Shell | |
| 3,926,188 A | 12/1975 | Baker et al. | |
| 4,014,335 A | 3/1977 | Arnold | |
| 4,093,709 A | 6/1978 | Choi et al. | |
| 4,300,557 A | 11/1981 | Refojo et al. | |
| 4,316,885 A | 2/1982 | Rakhit | |
| 4,650,803 A | 3/1987 | Stella et al. | |
| 4,853,224 A | 8/1989 | Wong | |
| 4,946,450 A | 8/1990 | Erwin | |
| 4,997,652 A | 3/1991 | Wong | |
| 5,011,844 A | 4/1991 | Fehr | |
| 5,023,262 A | 6/1991 | Caufield et al. | |
| 5,078,999 A | 1/1992 | Warner et al. | |
| 5,100,899 A | 3/1992 | Calne | |
| 5,120,725 A | 6/1992 | Kao et al. | |
| 5,120,727 A | 6/1992 | Kao et al. | |
| 5,120,842 A | 6/1992 | Failli et al. | |
| 5,147,647 A | 9/1992 | Darougar | |
| 5,164,188 A | 11/1992 | Wong | |
| 5,177,203 A | 1/1993 | Failli et al. | |
| 5,178,635 A | 1/1993 | Gwon et al. | |
| 5,189,042 A | 2/1993 | Goulet et al. | |
| 5,192,773 A | 3/1993 | Armistead et al. | |
| 5,192,802 A | 3/1993 | Rencher | |
| 5,258,389 A | 11/1993 | Goulet et al. | |
| 5,300,114 A | 4/1994 | Gwon et al. | |
| 5,322,691 A | 6/1994 | Darougar et al. | |
| 5,368,865 A | 11/1994 | Asakura et al. | |
| 5,378,475 A | 1/1995 | Smith et al. | |
| 5,387,589 A | 2/1995 | Kulkarni | |
| 5,395,618 A | 3/1995 | Darougar et al. | |
| 5,403,901 A | 4/1995 | Namdaran et al. | |
| 5,443,505 A | 8/1995 | Wong et al. | |
| 5,457,111 A | 10/1995 | Luly et al. | |
| 5,466,233 A | 11/1995 | Weiner et al. | |
| 5,514,686 A | 5/1996 | Mochizuki et al. | |
| 5,516,522 A | 5/1996 | Peyman et al. | |
| 5,516,770 A | 5/1996 | Waranis et al. | |
| 5,516,781 A | 5/1996 | Morris et al. | |
| 5,527,907 A | 6/1996 | Or et al. | |
| 5,530,006 A | 6/1996 | Waranis et al. | |
| 5,532,248 A | 7/1996 | Goulet et al. | |
| 5,536,729 A | 7/1996 | Waranis et al. | |
| 5,559,121 A | 9/1996 | Harrison et al. | |
| 5,583,139 A | 12/1996 | Or et al. | |
| 5,601,844 A | 2/1997 | Kagayama et al. | |
| 5,614,547 A | 3/1997 | Hamilton et al. | |
| 5,616,588 A | 4/1997 | Waranis et al. | |
| 5,621,108 A | 4/1997 | Smith, III et al. | |
| 5,632,984 A | 5/1997 | Wong et al. | |
| 5,672,605 A | 9/1997 | Or et al. | |
| 5,679,666 A | 10/1997 | Clark | |
| 5,696,135 A | 12/1997 | Steiner et al. | |
| 5,725,493 A | 3/1998 | Avery et al. | |
| 5,743,274 A | 4/1998 | Peyman | |
| 5,766,242 A | 6/1998 | Wong et al. | |
| 5,766,619 A | 6/1998 | Aiache et al. | |

(Continued)

FOREIGN PATENT DOCUMENTS

| | | |
|---|---|---|
| CN | 1333018 A | 1/2002 |
| CN | 1340358 A | 3/2002 |

(Continued)

OTHER PUBLICATIONS

RAPMUNE (http://www.nanotechproject.org/inventories/medicine/apps/ immunosuppressant/rapamune (2000)).*
Hafizi, S. et al. (2005). "Differential Effects of Rapamycin, Cyclosporine A, and FK506 on Human Coronary Artery Smooth Muscle Cell Proliferation and Signalling," *Vasul. Pharmacol.* 41:167-176.
Hayward, C.M. et al. (1993). "Total Synthesis of Rapamycin via a Novel Titanium-Mediated Aldol Macrocyclization Reaction," *J. Am. Chem. Soc.* 115(20):9345-9346.
Kulkarni, P.S. (1994). "Steroidal and Nonsteroidal Drugs in Endotoxin-Induced Uveitis," *J. Ocul. Pharmacol.* 10(1):329-334.
Nicolaou, K.C. et al. (1993). "Total Synthesis of Rapamycin," *J. Am. Chem. Soc.* 115(10):4419-4420.
Ohia, E.O. et al. (1992). "Effects of Steroids and Immunosuppressive Drugs on Endotoxin-Uveitis in Rabbits," *J. Ocul. Pharmacol.* 8(4):295-307.
Paiva, N.L. et al. (Jan.-Feb. 1991). "Incorporation of Acetate, Propionate, and Methionine Into Rapamycin by *Streptomyces hygroscopicus*," *J. Nat. Prod.* 54(1):167-177.

(Continued)

*Primary Examiner* — Jake Vu
(74) *Attorney, Agent, or Firm* — Morrison & Foerster LLP

(57) ABSTRACT

Described herein are formulations comprising therapeutic agents, including but not limited to formulations comprising rapamycin, pharmaceutical formulations, unit dose forms, kits, methods of preparing formulations, and methods of using formulations. Such formulations and methods have increased stability.

26 Claims, 15 Drawing Sheets

U.S. PATENT DOCUMENTS

| | | | |
|---|---|---|---|
| 5,770,592 A | 6/1998 | Clark | |
| 5,773,019 A | 6/1998 | Ashton et al. | |
| 5,773,021 A | 6/1998 | Gurtler et al. | |
| 5,798,355 A | 8/1998 | Steiner et al. | |
| 5,824,072 A | 10/1998 | Wong | |
| 5,830,173 A | 11/1998 | Avery et al. | |
| 5,883,082 A | 3/1999 | Bennett et al. | |
| 5,902,598 A | 5/1999 | Chen et al. | |
| 5,904,144 A | 5/1999 | Hammang et al. | |
| 5,912,253 A | 6/1999 | Cottens et al. | |
| 6,004,973 A | 12/1999 | Guitard et al. | |
| 6,007,510 A | 12/1999 | Nigam | |
| 6,015,815 A | 1/2000 | Mollison | |
| 6,074,661 A | 6/2000 | Olejnik et al. | |
| 6,110,485 A | 8/2000 | Olejnik et al. | |
| 6,126,687 A | 10/2000 | Peyman | |
| 6,142,969 A | 11/2000 | Nigam | |
| 6,217,895 B1 | 4/2001 | Guo et al. | |
| 6,239,102 B1 | 5/2001 | Tiemessen | |
| 6,239,113 B1 | 5/2001 | Dawson et al. | |
| 6,254,860 B1 | 7/2001 | Garst | |
| 6,258,856 B1 | 7/2001 | Chamberlain et al. | |
| 6,267,985 B1 | 7/2001 | Chen et al. | |
| 6,306,422 B1 | 10/2001 | Batich et al. | |
| 6,326,387 B1 | 12/2001 | Armistead | |
| 6,329,386 B1 | 12/2001 | Mollison | |
| 6,331,313 B1 | 12/2001 | Wong et al. | |
| 6,350,442 B2 | 2/2002 | Garst | |
| 6,361,760 B1 | 3/2002 | Murata et al. | |
| 6,375,972 B1 | 4/2002 | Guo et al. | |
| 6,376,517 B1 | 4/2002 | Ross et al. | |
| 6,378,526 B1 | 4/2002 | Bowman et al. | |
| 6,387,918 B1 | 5/2002 | Yamanaka et al. | |
| 6,397,849 B1 | 6/2002 | Bowman et al. | |
| 6,399,629 B1 | 6/2002 | Chamberland et al. | |
| 6,413,245 B1 | 7/2002 | Yaacobi et al. | |
| 6,413,540 B1 | 7/2002 | Yaacobi | |
| 6,416,777 B1 | 7/2002 | Yaacobi | |
| 6,440,990 B1 | 8/2002 | Cottens et al. | |
| 6,455,518 B2 | 9/2002 | Zenke et al. | |
| 6,482,802 B1 | 11/2002 | Hu et al. | |
| 6,489,335 B2 | 12/2002 | Peyman | |
| 6,534,693 B2 | 3/2003 | Fischell et al. | |
| 6,569,443 B1 | 5/2003 | Dawson et al. | |
| 6,576,224 B1 | 6/2003 | Osbakken et al. | |
| 6,617,345 B1 | 9/2003 | Gregory et al. | |
| 6,632,836 B1 | 10/2003 | Baker et al. | |
| 6,656,460 B2 | 12/2003 | Benita et al. | |
| 6,699,493 B2 | 3/2004 | Wong | |
| 6,713,081 B2 | 3/2004 | Robinson et al. | |
| 6,719,750 B2 | 4/2004 | Varner et al. | |
| 6,777,000 B2 | 8/2004 | Ni et al. | |
| 6,812,220 B2 | 11/2004 | Jackson et al. | |
| 6,852,729 B2 * | 2/2005 | Navarro et al. | 514/291 |
| 6,864,232 B1 | 3/2005 | Ueno | |
| 6,872,383 B2 | 3/2005 | Ueno | |
| 6,890,546 B2 | 5/2005 | Mollison et al. | |
| 6,939,878 B2 | 9/2005 | Naicker et al. | |
| 6,956,043 B2 | 10/2005 | Guitard et al. | |
| 7,014,861 B2 | 3/2006 | Roorda et al. | |
| 7,018,808 B2 | 3/2006 | Leadlay et al. | |
| 7,026,374 B2 | 4/2006 | Nathan et al. | |
| 7,033,604 B2 | 4/2006 | Ueno | |
| 7,033,605 B2 | 4/2006 | Wong | |
| 7,034,037 B2 | 4/2006 | Arnold et al. | |
| 7,063,857 B1 | 6/2006 | Ueno | |
| 7,083,802 B2 | 8/2006 | Peyman | |
| 7,083,803 B2 | 8/2006 | Peyman | |
| 7,087,237 B2 | 8/2006 | Peyman | |
| 7,128,897 B2 | 10/2006 | Osbakken et al. | |
| 7,160,867 B2 | 1/2007 | Abel et al. | |
| 7,181,287 B2 | 2/2007 | Greenberg | |
| 7,183,289 B2 | 2/2007 | Zhang et al. | |
| 7,186,518 B2 | 3/2007 | Wang et al. | |
| 7,223,286 B2 | 5/2007 | Wright et al. | |
| 7,354,574 B2 | 4/2008 | Peyman | |
| 7,402,399 B2 | 7/2008 | Mukherjeei et al. | |
| 7,846,940 B2 * | 12/2010 | Falotico et al. | 514/291 |
| 2002/0123505 A1 | 9/2002 | Mollison et al. | |
| 2002/0187998 A1 | 12/2002 | Ueno | |
| 2003/0018044 A1 | 1/2003 | Peyman | |
| 2003/0027744 A1 | 2/2003 | Dana et al. | |
| 2003/0069232 A1 | 4/2003 | Chiou | |
| 2003/0069560 A1 | 4/2003 | Adamis et al. | |
| 2003/0077297 A1 | 4/2003 | Chen et al. | |
| 2003/0171320 A1 | 9/2003 | Guyer | |
| 2003/0190286 A1 | 10/2003 | Dugger, III | |
| 2003/0203892 A1 | 10/2003 | Keller et al. | |
| 2004/0018228 A1 | 1/2004 | Fischell et al. | |
| 2004/0054012 A1 * | 3/2004 | Dietlin et al. | 514/646 |
| 2004/0057958 A1 | 3/2004 | Waggoner, Jr. et al. | |
| 2004/0167152 A1 | 8/2004 | Rubino et al. | |
| 2004/0175428 A1 | 9/2004 | Appel et al. | |
| 2004/0180075 A1 | 9/2004 | Robinson et al. | |
| 2004/0198763 A1 | 10/2004 | Ueno | |
| 2004/0219181 A1 | 11/2004 | Viscasillas | |
| 2004/0224394 A1 | 11/2004 | Katz et al. | |
| 2004/0234611 A1 | 11/2004 | Ahlheim et al. | |
| 2005/0032826 A1 | 2/2005 | Mollison et al. | |
| 2005/0037048 A1 * | 2/2005 | Song | 424/423 |
| 2005/0042215 A1 | 2/2005 | Owen et al. | |
| 2005/0048123 A1 | 3/2005 | Su et al. | |
| 2005/0064010 A1 | 3/2005 | Cooper et al. | |
| 2005/0074497 A1 | 4/2005 | Schultz | |
| 2005/0084514 A1 | 4/2005 | Shebuski et al. | |
| 2005/0123605 A1 | 6/2005 | Hunter et al. | |
| 2005/0142162 A1 | 6/2005 | Hunter et al. | |
| 2005/0143363 A1 | 6/2005 | De Juan et al. | |
| 2005/0187241 A1 | 8/2005 | Wen et al. | |
| 2005/0196440 A1 | 9/2005 | Masters et al. | |
| 2005/0222191 A1 | 10/2005 | Falotico et al. | |
| 2005/0232952 A1 | 10/2005 | Lambert et al. | |
| 2005/0249710 A1 | 11/2005 | Wong | |
| 2005/0250804 A1 | 11/2005 | Kannan et al. | |
| 2005/0255144 A1 | 11/2005 | Schultz | |
| 2006/0002971 A1 | 1/2006 | Saltzman et al. | |
| 2006/0024350 A1 | 2/2006 | Varner et al. | |
| 2006/0034891 A1 | 2/2006 | Lawin et al. | |
| 2006/0073182 A1 | 4/2006 | Wong et al. | |
| 2006/0182771 A1 | 8/2006 | Dor et al. | |
| 2006/0182783 A1 | 8/2006 | Hughes et al. | |
| 2006/0198867 A1 | 9/2006 | Toner et al. | |
| 2006/0216288 A1 | 9/2006 | Chang | |
| 2006/0228393 A1 | 10/2006 | Peyman | |
| 2006/0228394 A1 | 10/2006 | Peyman | |
| 2006/0247265 A1 | 11/2006 | Clackson et al. | |
| 2006/0257450 A1 | 11/2006 | Mudumba et al. | |
| 2006/0258698 A1 | 11/2006 | Mudumba et al. | |
| 2006/0263409 A1 | 11/2006 | Peyman | |
| 2006/0264453 A1 | 11/2006 | Mudumba et al. | |
| 2006/0275218 A1 | 12/2006 | Tamarkin et al. | |
| 2007/0014760 A1 | 1/2007 | Peyman | |
| 2007/0015697 A1 | 1/2007 | Peyman | |
| 2007/0134244 A1 | 6/2007 | Slakter et al. | |
| 2007/0197567 A1 | 8/2007 | Sherris | |
| 2007/0265294 A1 | 11/2007 | Kleinman et al. | |

FOREIGN PATENT DOCUMENTS

| | | |
|---|---|---|
| CN | 1456350 A | 11/2003 |
| CN | 1556694 A | 12/2004 |
| CN | 1671385 A | 9/2005 |
| DE | 40225553 A1 | 1/1992 |
| DE | 19810655 A1 | 9/1999 |
| EP | 0041745 A1 | 12/1981 |
| EP | 0041795 A2 | 12/1981 |
| EP | 0 467 606 A1 | 1/1992 |
| EP | 0904787 A1 | 3/1999 |
| EP | 1142566 A1 | 10/2001 |
| EP | 1126849 B1 | 3/2005 |
| FR | 2382240 C1 | 9/1978 |
| GB | 2278780 A | 12/1994 |
| JP | 8-333257 A | 12/1996 |
| JP | 09-030966 | 2/1997 |
| JP | 09-315954 | 12/1997 |
| JP | 10-218787 | 8/1998 |
| JP | 2001-064198 | 3/2001 |
| JP | 2002-332225 | 11/2002 |

| | | | |
|---|---|---|---|
| JP | 2002-332225 A | 11/2002 | |
| JP | 2003-113078 A | 4/2003 | |
| RU | 2123314 C1 | 12/1998 | |
| RU | 2149615 C1 | 5/2000 | |
| WO | WO-89/01772 A1 | 3/1989 | |
| WO | WO-92/05179 A1 | 4/1992 | |
| WO | WO-93/19763 A1 | 10/1993 | |
| WO | WO-94/05257 A1 | 3/1994 | |
| WO | WO-94/21642 A1 | 9/1994 | |
| WO | WO-95/14023 A1 | 5/1995 | |
| WO | WO-95/26734 A1 | 10/1995 | |
| WO | WO-95/28984 A1 | 11/1995 | |
| WO | WO-96/36377 A1 | 11/1996 | |
| WO | WO-96/40140 A1 | 12/1996 | |
| WO | WO-96/41865 A1 | 12/1996 | |
| WO | WO-97/10806 A1 | 3/1997 | |
| WO | WO-97/16068 A1 | 5/1997 | |
| WO | WO-99/07418 A2 | 2/1999 | |
| WO | WO-99/11244 A1 | 3/1999 | |
| WO | WO-99/20261 A2 | 4/1999 | |
| WO | WO-99/22722 A2 | 5/1999 | |
| WO | WO-99/34830 A1 | 7/1999 | |
| WO | WO-99/37667 A1 | 7/1999 | |
| WO | WO-99/45920 A2 | 9/1999 | |
| WO | WO-99/58126 A1 | 11/1999 | |
| WO | WO-00/06121 A1 | 2/2000 | |
| WO | WO-00/09109 A2 | 2/2000 | |
| WO | WO-00/09109 A3 | 2/2000 | |
| WO | WO-00/09112 A2 | 2/2000 | |
| WO | WO-00/09479 A2 | 2/2000 | |
| WO | WO-00/28945 A2 | 5/2000 | |
| WO | WO-00/33878 A2 | 6/2000 | |
| WO | WO-00/37066 A2 | 6/2000 | |
| WO | WO-00/38703 A2 | 7/2000 | |
| WO | WO-00/40089 A1 | 7/2000 | |
| WO | WO-00/56340 A1 | 9/2000 | |
| WO | WO-00/66122 A1 | 11/2000 | |
| WO | WO-01/28522 A2 | 4/2001 | |
| WO | WO-01/30386 A1 | 5/2001 | |
| WO | WO-01/42219 A2 | 6/2001 | |
| WO | WO-01/47495 A1 | 7/2001 | |
| WO | WO-01/93830 A1 | 12/2001 | |
| WO | WO-02/28387 A1 | 4/2002 | |
| WO | WO-02/062335 A2 | 8/2002 | |
| WO | WO-02/066019 A2 | 8/2002 | |
| WO | WO-02/074196 A1 | 9/2002 | |
| WO | WO-02/100318 A2 | 12/2002 | |
| WO | WO-03/017990 A2 | 3/2003 | |
| WO | WO-03/051385 A1 | 6/2003 | |
| WO | WO-03/068186 A1 | 8/2003 | |
| WO | WO-03/074027 A2 | 9/2003 | |
| WO | WO-03/074029 A1 | 9/2003 | |
| WO | WO-03/090684 A2 | 11/2003 | |
| WO | WO-2004/007709 A2 | 1/2004 | |
| WO | 2004/011000 A1 | 2/2004 | |
| WO | WO-2004/011000 A1 | 2/2004 | |
| WO | WO-2004/014373 A1 | 2/2004 | |
| WO | WO-2004/019904 A1 | 3/2004 | |
| WO | WO-2004/027027 A2 | 4/2004 | |
| WO | WO-2004/027027 A3 | 4/2004 | |
| WO | WO-2004/028477 A2 | 4/2004 | |
| WO | WO-2004/028477 A3 | 4/2004 | |
| WO | WO-2004/043480 A2 | 5/2004 | |
| WO | WO-2004/060283 A2 | 7/2004 | |
| WO | WO-2004/074445 A2 | 9/2004 | |
| WO | WO-2004/096261 A1 | 11/2004 | |
| WO | WO-2005/002625 A2 | 1/2005 | |
| WO | WO-2005/011813 A2 | 2/2005 | |
| WO | WO-2005/020962 A1 | 3/2005 | |
| WO | WO-2005/027906 A1 | 3/2005 | |
| WO | WO-2005/030205 A1 | 4/2005 | |
| WO | WO-2005/051452 A2 | 6/2005 | |
| WO | WO-2005/055945 A2 | 6/2005 | |
| WO | WO-2005/082376 A1 | 9/2005 | |
| WO | WO-2005/094279 A2 | 10/2005 | |
| WO | WO-2005/099715 A2 | 10/2005 | |
| WO | WO-2005/110436 A2 | 11/2005 | |
| WO | WO-2005/110473 A2 | 11/2005 | |
| WO | WO-2006/002365 A2 | 1/2006 | |
| WO | WO-2006/002366 A2 | 1/2006 | |
| WO | WO-2006/002399 A2 | 1/2006 | |
| WO | WO-2006/014484 A2 | 2/2006 | |
| WO | WO-2006/020755 A2 | 2/2006 | |
| WO | WO-2006/023627 A1 | 3/2006 | |
| WO | WO-2006/026531 A1 | 3/2006 | |
| WO | WO-2006/039336 A2 | 4/2006 | |
| WO | WO-2006/041942 A2 | 4/2006 | |
| WO | WO-2006/053007 A2 | 5/2006 | |
| WO | WO-2006/086744 A1 | 8/2006 | |
| WO | WO-2006/086750 A1 | 8/2006 | |
| WO | WO-2006/102378 A2 | 9/2006 | |
| WO | WO-2006/102378 A3 | 9/2006 | |
| WO | WO-2006/108239 A1 | 10/2006 | |
| WO | WO-2006/110487 A1 | 10/2006 | |
| WO | WO-2006/116716 A2 | 11/2006 | |
| WO | WO-2006/133052 A2 | 12/2006 | |
| WO | WO-2007/011880 A2 | 1/2007 | |
| WO | WO-2007/065588 A1 | 6/2007 | |
| WO | WO-2007/083316 A2 | 7/2007 | |
| WO | WO-2007/092620 A2 | 8/2007 | |
| WO | WO-2007/112052 A2 | 10/2007 | |

OTHER PUBLICATIONS

Raghava, S. et al. (Nov. 2004). "Periocular Routes for Retinal Drug Delivery," *Expert. Opin. Drug. Deliv.* 1(1):99-114.

Romo, D. et al. (1993). "Total Synthesis of (−)-Rapamycin Using an Evans-Tishchenko Fragment Coupling," *J. Am. Chem. Soc.* 115(17):7906-7907.

Sehgal, S.N. et al. (Oct. 1975). "Rapamycin (AY-22,989), A New Antifungal Antibiotic. II. Fermentation, Isolation and Characterization," *J. Antibiot.* 28(10):727-732.

Sehgal, S.N. et al. (Apr. 1983). "Demethoxyrapamycin (AY-24,668), A New Antifungal Antibiotic," *J. Antibiot.* 36(4):351-354.

Simamora, P. et al. (2001). "Solubilization of Rapamycin," *Intl. J. Pharma.* 213:25-29.

Vézina, C. et al. (Oct. 1975). "Rapamycin (AY-22,989), A New Antifungal Antibiotic. I. Taxonomy of the Producing Streptomycete and Isolation of the Active Principle," *J. Antibiot.* 28(10):721-726.

Arias, L. (2007). "Management of Diabetic Macular Edema with Antiangiogenic Therapy," *Expert Review of Ophthalmology* 2(1):23-26.

Averbukh, E. et al. (Feb. 2006). "Diabetic Macular Edema: Towards Therapy Aimed at the Underlying Pathogenic Mechanisms," *The Israel Medical Association Journal* 8:127-128.

Bertelmann, E. et al. (2004). "Immunomodulatory Therapy in Ophthalmology—Is There a Place for Topical Application?," *Ophthalmologica* 218:359-367.

Chusid, M. J. et al. (Oct. 1986). "The Role of the Polymorphonuclear Leukocyte in the Induction of Corneal Edema," *Investigative Ophthalmology & Visual Science* 27(10):1466-1469.

Ciulla, T. A. et al. (Sep. 2003). "Diabetic Retinopathy and Diabetic Macular Edema: Pathophysiology, Screening, and Novel Therapies," *Diabetes Care* 26(9):2653-2664.

Ciulla. T. A. et al. (Sep.-Oct. 1998). "Age-Related Macular Degeneration: A Review of Experimental Treatments," *Survey of Ophthalmology* 43(2):134-146.

Gardner, T. W. et al. (2008). "Novel Potential Mechanisms for Diabetic Macular Edema: Leveraging New Investigational Approaches," *Current Diabetes Reports* 8:263-269.

International Search Report and Written Opinion mailed Feb. 6, 2009, for PCT Application No. PCT/US2007/003573 filed Aug. 18, 2008, 22 pages.

Lal, A. (1993). "Drop Volume of Commercial Anti-Glaucoma Eye Drops," *Indian Journal of Pharmacology* 25:163-164.

MacuSight, Inc. "Safety and Tolerability of MS-R001 in Patients with Diabetic Macular Edema Secondary to Diabetic Retinopathy," located at <http://clinicaltrials.gov/ct2/show/NCT00401115?term=macular+edema+and+rapamycin&rank=3> visited on Jan. 26, 2009. (3 pages).

National Eye Institute (NEI). "Sirolimus to Treat Diabetic Macular Edema," located at <http://clinicaltrials.gov/ct2/show/NCT00711490?term=macular+edema+and+rapamycin&rank=1> visited on Jan. 26, 2009. (6 pages).

Pavan-Langston, D. (1996). *Manual of Ocular Diagnosis and Therapy.* Fourth Edition, Little, Brown and Company: New York, pp. 162-165.

United States Office Action mailed Apr. 22, 2009, for U.S. Appl. No. 11/386,290, filed Mar. 21, 2006, 13 pages.

United States Office Action mailed Apr. 3, 2008, for U.S. Appl. No. 10/665,203, filed Sep. 18, 2003, 6 pages.

United States Office Action mailed Aug. 6, 2008, for U.S. Appl. No. 11/386,290, filed Mar. 21, 2006, 8 pages.

United States Office Action mailed Feb. 11, 2009, for U.S. Appl. No. 11/352,092, filed Feb. 9, 2006, 13 pages.

United States Office Action mailed Feb. 2, 2009, for U.S. Appl. No. 11/351,761, filed Feb. 9, 2006, 14 pages.

United States Office Action mailed Feb. 7, 2008, for U.S. Appl. No. 10/945,682, filed Sep. 20, 2004, 8 pages.

United States Office Action mailed Jan. 12, 2009, for U.S. Appl. No. 10/665,203, filed Sep. 18, 2003, 6 pages.

United States Office Action mailed Jan. 29, 2009, for U.S. Appl. No. 10/945,682, filed Sep. 20, 2004, 8 pages.

United States Office Action mailed Jan. 5, 2010, for U.S. Appl. No. 11/351,844, filed Feb. 9, 2006, 11 pages.

United States Office Action mailed Jul. 6, 2007, for U.S. Appl. No. 10/665,203, filed Sep. 18, 2003, 4 pages.

United States Office Action mailed Jun. 11, 2009, for U.S. Appl. No. 11/726,813, filed Mar. 23, 2007, 17 pages.

United States Office Action mailed Mar. 12, 2009, for U.S. Appl. No. 11/351,844, filed Feb. 9, 2006, 22 pages.

United States Office Action mailed Mar. 16, 2010, for U.S. Appl. No. 11/726,813, filed Mar. 23, 2007, 12 pages.

United States Office Action mailed Nov. 12, 2009, for U.S. Appl. No. 11/351,761, filed Feb. 9, 2006, 10 pages.

United States Office Action mailed Nov. 25, 2009, for U.S. Appl. No. 11/352,092, filed Feb. 9, 2006, 7 pages.

Xue et al. (Nov. 15, 2008). "Palomid 529, a novel small-molecule drug, is a TORC1/TORC2 inhibitor that reduces tumor growth, tumor angiogenesis, and vascular permeability," *Cancer Res.* 68(22):9551-9557.

Akselband, Y. et al. (Dec. 1991). "Rapamycin Inhibits Spontaneous and Fibroblast Growth Factor Beta-Stimulated Proliferation of Endothelial Cells and Fibroblasts," *Transplantation Proceedings* 23(6):2833-2836.

Alteheld, A. et al. (2005). "Biodegradable Amorphous Copolyester-Urethane Networks Having Shape-Memory Properties," *Angewandte Chemie International Edition* 44:1188-1192.

Apel, A. et al. (Aug. 1995). "A Subconjuctival Degradable Implant for Cyclosporine Delivery in Corneal Transplant Therapy," *Current Eye Research* 14(8):659-667.

Aramoto, H. et al. (Oct. 2004). "Vascular Endothelial Growth Factor Stimulates Differential Signaling Pathways in In Vivo Microcirculation," *American Journal of Physiology—Heart and Circulatory Physiology* 287:H1590-H1598.

Auricchio, A. et al. (Aug. 2002). "Pharmacological Regulation of Protein Expression from Adeno-Associated Viral Vectors in the Eye," *Molecular Therapy* 6(2):238-242.

Bainbridge, J. W. B. et al. (2003). "Hypoxia-Regulated Transgene Expression in Experimental Retinal Choroidal Neovascularization," *Gene Therapy* 10:1049-1054.

Beeley, N. R. F. et al. (Mar. 15, 2006). "Development, Implantation, In Vivo Elution, and Retrieval of a Biocompatible, Sustained Release Subretinal Drug Delivery System," *Journal of Biomedical Materials Research Part A* 76A:690-698.

Behl, C. (Dec. 1997). "Amyloid Beta-Protein Toxicity and Oxidative Stress in Alzheimer's Disease," *Cell & Tissue Research* 290(3):471-480.

Bergers, G. et al. (Jun. 2003). "Tumorigenesis and the Angiogenic Switch," *Nature Reviews—Cancer* 3(6):401-410.

Bourne, R. R. et al., (1998). "Epidemic Optic Neuropathy in Primary School Children in Dar es Salaam, Tanzania," *British Journal of Ophthalmology* 82:232-234.

Bucci, M. et al. (Dec. 2000). "In Vivo Delivery of the Caveolin-1 Scaffolding Domain Inhibits Nitric Oxide Synthesis and Reduces Inflammation," *Nature Medicine* 6(12):1362-1367.

Cancer Weekly Editors. (Jan. 14, 2003). "Cancer Therapy: Study of Possible Anticancer Drug Reveals New Mechanism of Gene Regulation," *Cancer Weekly* via NewsRx.com and NewsRx.net, 2 pages.

Cicciarelli, N. et al. (Mar. 15, 2001). "Pharmacokinetics of Subconjunctivally Administered Cyclosporine A: Local Delivery Prior to Chemotherapy for Retinoblastoma," *IOVS*, Apr. 29-May 4, 2001, Fort Lauderdale, Florida, 42(4):S332, Abstract 1792-B42.

Edinger, A. L. et al. (Dec. 1, 2003). "Differential Effects of Rapamycin on Mammalian Target of Rapamycin Signaling Functions in Mammalian Cells," *Cancer Research* 63:8451-8460.

Geroski, D. H. et al. (2001). "Transscleral Drug Delivery for Posterior Segment Disease," *Advanced Drug Delivery Reviews* 52:37-48.

Gilbard, J. P. (Feb. 1999). "EW Interview: Electrolyte Balance is Key to Dry-eye Product's Success," *Eye World*, pp. 20-21.

Guba, M. et al. (2001). "Rapamycin Inhibits Tumor Growth and Metastasis by Antiangiogenesis," *Chirurgisches Forum 2001*, pp. 37-39. (English Abstract attached).

Guba, M. et al. (Feb. 2002). "Rapamycin Inhibits Primary and Metastatic Tumor Growth by Antiangiogenesis: Involvement of Vascular Endothelial Growth Factor," *Nature Medicine* 8(2):128-135.

Hackstein, H. et al. (Aug. 1, 2002). "Rapamycin Inhibits Macropinocytosis and Mannose Receptor-Mediated Endocytosis by Bone Marrow-Derived Dendritic Cells," *Blood* 100(3):1084-1087.

Harris, A. et al. (2001). "Implantation of a Sustained-Release Ganciclovir Implant," Chapter 45 *In Vitreoretinal Surgical Techniques*, pp. 521-531.

Humar, R. et al. (2002). "Hypoxia Enhances Vascular Cell Proliferation and Angiogenesis In Vitro Via Rapamycin (mTOR)-Dependent Signaling," *The FASEB Journal* 16:771-780.

Invitation to Pay Additional Fees mailed Sep. 12, 2008, for PCT Application No. PCT/US2007/003573 filed Feb. 2, 2007, 15 pages.

Kuroki, A. et al. (2003). "Rapamycin Inhibits Retinal and Choroidal Neovascularization in Mice," *Investigative Ophthalmology & Visual Science* 44:E-Abstract 573, 2 pages.

Lallemand, F. et al. (2003). "Cyclosporine A Delivery to the Eye: A Pharmaceutical Challenge," *European Journal of Pharmaceutics and Biopharmaceutics* 56:307-318.

Lipner, M. (Feb. 1999). "Dry Eye 101: Developing Etiologies and Treatments for the Widespread Syndrome," *Eye World*, pp. 19, 21.

Macular Photocoagulation Study Group. (May 1986). "Argon Laser Photocoagulation for Neovascular Maculopathy, Three-Year Results from Randomized Clinical Trials," *Archives of Ophthalmology* 104:694-701.

Macular Photocoagulation Study Group. (Sep. 1991). "Laser Photocoagulation of Subfoveal Neovascular Lesions in Age-Related Macular Degeneration, Results of a Randomized Clinical Trial," *Archives of Ophthalmology* 109:1220-1231.

Macular Photocoagulation Study Group. (Sep. 1991). "Laser Photocoagulation of Subfoveal Recurrent Neovascular Lesions in Age-Related Macular Degeneration, Results of a Randomized Clinical Trial," *Archives of Ophthalmology* 109:1232-1241.

Macular Photocoagulation Study Group. (Sep. 1991). "Subfoveal Neovascular Lesions in Age-Related Macular Degeneration, Guidelines for Evaluation and Treatment in the Macular Photocoagulation Study," *Archives of Ophthalmology* 109:1242-1257.

Marsland, A. M. et al. (Nov.-Dec. 2002). "The Macrolide Immunosuppressants in Dermatology: Mechanisms of Action," *European Journal of Dermatology* 12:618-621.

Martin, D. F. et al. (Jan. 15, 1995). "Synergistic Effect of Rapamycin and Cyclosporin A in the Treatment of Experimental Autoimmune Uveoretinitis," *The Journal of Immunology* 154(2):922-927.

Mayhan, W. G. et al. (Sep. 1984). "The Effect of Altering the External Calcium Concentration and a Calcium Channel Blocker, Verapamil, on Microvascular Leaky Sites and Dextran Clearance in the Hamster Cheek Pouch," *Microvascular Research* 28(2):159-179.

MediVas. (2007). "MediVas Announces Signing of Collaboration Agreement with Pfizer," located at <www.medivas.com/News/news_MediVas_Announces_Signing_of_Collaboration_Agreement_with_Pfizer.html> visited on Jul. 28, 2008. (1 page).

Murphy, R. P. (Mar. 1995). "Management of Diabetic Retinopathy," *American Family Physician* 51(4):785-796.

Napoli, K. L. et al. (2001). "From Beach to Bedside: History of the Development of Sirolimus," *Therapeutic Drug Monitoring* 23(5):559-586.

Olsen, T. W. et al. (Nov. 1994). "Rapamycin Inhibits Corneal Allograft Rejection and Neovascularization," *Archives of Ophthalmology* 112:1471-1475.

Passos, E. et al. (Mar./Apr. 2002). "Ocular Toxcity of Intravitreal Tacrolimus," *Ophthalmic Surgery and Lasers* 33(2):140-144.

Phung, T. L. et al. (Aug. 2006). "Pathological Angiogenesis is Induced by Sustained Akt Signaling and Inhibited by Rapamycin," *Cancer Cell* 10:159-170.

Renau, T. E. et al. (2003). "Conformationally-Restricted Analogues of Efflux Pump Inhibitors that Potentiate the Activity of Levofloxaxin in *Pseudomonas aeruginosa*," *Bioorganic & Medicinal Chemistry Letters* 13:2755-2758.

Renau, T. E. et al., (2001). "Addressing the Stability of C-Capped Dipeptide Efflux Pump Inhibitors that Potentiate the Activity of Levofloxacin in *Pseudomonas aeruginosa*," *Bioorganic & Medicinal Chemistry Letters* 11:663-667.

Rivera, V. M. et al. (Jul. 1999). "Long-Term Regulated Expression of Growth Hormone in Mice after Intramuscular Gene Transfer," *Proceedings of the National Academy of Sciences of the United States of America* 96:8657-8662.

Robinson, J. R. et al. (1995). "Bioadhesive and Phase-Change Polymers for Ocular Drug Delivery," *Advanced Drug Delivery Reviews* 16:45-50.

Schlingemann, R. O. et al. (Jun. 1997). "Role of Vascular Permeability Factor/Vascular Endothelial Growth Factor in Eye Disease," *British Journal of Ophthalmology* 81(6):501-512.

Shen, W.-Y. et al. (Jul. 2001). "Combined Effect of Cyclosporine and Sirolimus on Improving the Longevity of Recombinant Adenovirus-Mediated Transgene Expression in the Retina," *Archives of Ophthalmology* 119:1033-1043.

Spaide, R. F. et al. (Aug. 2003). "Combined Photodynamic Therapy With Verteporfin and Intravitreal Triamcinolone Acetonide for Choroidal Neovascularization," *Ophthalmology* 110(8):1517-1525.

Stepkowski, S. M. et al. (Jan. 1991). "Rapamycin, a Potent Immunosuppressive Drug for Vascularized Heart, Kidney, and Small Bowel Transplantation in the Rat," *Transplantation* 51(1):22-26.

Treatment of Age-Related Macular Degeneration with Photodynamic Therapy (TAP) Study Group. (Apr. 2000). Correction for "Photodynamic Therapy of Subfoveal Choroidal Neovascularization in Age-Related Macular Degeneration with Verteporfin, One-Year Results of 2 Randomized Clinical Trials—TAP Report 1," *Archives of Ophthalmology* 118:488.

Treatment of Age-Related Macular Degeneration with Photodynamic Therapy (TAP) Study Group. (Oct. 1999). "Photodynamic Therapy of Subfoveal Choroidal Neovascularization in Age-Related Macular Degeneration With Verteporfin, One-Year Results of 2 Randomized Clinical Trials—TAP Report 1," *Archives of Ophthalmology* 117:1329-1345.

Treins, C. et al. (Aug. 2, 2002). "Insulin Stimulates Hypoxia-Inducible Factor 1 Through a Phosphatidylinositol 3-kinase/Target of Rapamycin-Dependent Signaling Pathway," *The Journal of Biological Chemistry* 277(31):27975-27981.

Wen, R. et al. (2003). "Rapamycin Inhibits Choroidal Neovascularization," *Investigative Ophthalmology & Visual Science* 44:E-Abstract 3928, 2 pages.

Office Action received for Japanese Patent Application No. 2008-554395, mailed on Nov. 6, 2012, 9 pages (6 pages of English Translation and 3 pages of Office Action).

Naito, Shuichi, "Stability of Medicine (Yakuzai no Anteisei)", Pharmaceutics System II, Third Edition, Apr. 1, 1976, pp. 130-131. (English Abstract submitted).

* cited by examiner

110

120

B.

STABLE FORMULATIONS, AND METHODS OF THEIR PREPARATION AND USE

CROSS-REFERENCE TO RELATED APPLICATION

The present application is related to and claims priority from U.S. Provisional Patent Application Ser. No. 60/772,018, titled "Stable Formulations, And Methods Of Their Preparation And Use," filed Feb. 9, 2006, the contents of which is incorporated herein by reference in its entirety for all purposes.

FIELD

Described herein are formulations comprising therapeutic agents, and methods of their preparation and use. Described herein are rapamycin formulations, and methods of their preparation and use.

BACKGROUND

Many formulations comprising therapeutic agents are sensitive to one or more elements or conditions which render them unstable after some period of time, for example when stored for a period of time. One such element or condition is sensitivity to one or more elements of the air, including but not limited to oxygen, in the space surrounding the formulation, such as the dead space or head space of a container containing the formulation. Another such element or condition is the presence of gases or dissolved gases in the formulation, including but not limited to oxygen, or exposure of one or more elements of the formulation to light, contaminating materials, or organisms such as bacteria. Another such condition or element is the ratio of the head space to the fill volume. Another such condition or element is the amount of a particular molecule relative to the amount of one or more components in a formulation, including but not limited to the active agent of the formulation.

Previous efforts to stabilize formulations include addition of one or more antioxidants such as BHT (butylated hydroxytoluene) or ascorbyl palmitate. Ascorbyl palmitate is generally used in oral and topical pharmaceuticals, as opposed to injectable formulations. Handbook Of Pharmaceutical Excipients 2003, American Pharmaceutical Association, Washington, D.C., USA and Pharmaceutical Press, London, UK. BHT is suggested at levels of about 0.0009 to about 0.002% for intravenous injectables in the Handbook Of Pharmaceutical Excipients (2003). It is thought that these stabilizing antioxidants are toxic at certain levels when administered to eye tissues. It would be preferable to have stable formulations that did not require additional formulation elements, including but not limited to preservatives, to retain their stability.

There is a need for formulations, including pharmaceutical formulations, that retain stability of one or more of a therapeutic agent or other elements present in a formulation comprising a therapeutic agent when the formulation is stored for a period of time. There is a need for stable formulations comprising therapeutic agents that are sensitive to exposure to one or more elements of the air. There is a need for stable formulations of rapamycin.

SUMMARY

Described herein are stable formulations comprising therapeutic agents, including stable formulations comprising rapamycin, pharmaceutical formulations, unit dose forms, kits, methods of preparing stable formulations, and methods of using stable formulations. The stable formulations include, without limitation, solutions, suspensions, self-emulsifying formulations, and in situ gelling formulations.

Described herein are liquid formulations comprising a therapeutic agent, including but not limited to rapamycin, comprising a level of dissolved nitrogen at least about 50% higher than the level of the formulation prepared without sparging with nitrogen.

Described herein are liquid formulations comprising a therapeutic agent, including but not limited to an immunophilin binding compound or rapamycin, comprising a level of oxygen in the dissolved gases of no greater than 20%, no greater than 19%, no greater than 17.5% or no greater than 16.5%.

Described herein are liquid formulations comprising a therapeutic agent, including but not limited to an immunophilin binding compound or rapamycin, comprising a level of nitrogen in the dissolved gases of greater than 80%, greater than 85%, greater than 90% or greater than 95%.

Described herein are sealed vessels comprising a liquid formulation comprising an immunophilin binding compound, wherein the liquid formulation is in contact with a head space gas having no greater than 20% oxygen gas, no greater than 15% oxygen gas, no greater than 10% oxygen gas, or no greater than 5% oxygen gas.

Described herein are sealed vessels comprising a liquid formulation comprising an immunophilin binding compound, wherein the liquid formulation is in contact with a head space gas having greater than 80% nitrogen gas, greater than 85% nitrogen gas, greater than 90% nitrogen gas, or greater than 95% nitrogen gas.

Described herein are ophthalmically acceptable liquid formulations comprising rapamycin, wherein the formula strength is at least 70% after 1 week of storage at one or more of −20° C., 5° C., or 25° C., at least 80% after 2 weeks of storage at one or more of −20° C., 5° C., or 25° C., at least 90% after 1 month of storage at one or more of −20° C., 5° C., or 25° C., at least 90% after 2 months of storage at one or more of −20° C., 5° C., or 25° C., at least 90% after 8 months of storage at one or more of −20° C. or 5° C.

Described herein are liquid formulations comprising a therapeutic agent sensitive to one or more components of the air, wherein the formula strength is at least 70% for at least 2 months at 25° C., at least 80% for at least 2 months at 25° C., at least 90% for at least 2 months at 25° C., and at least 95% for 2 months at 25° C., and wherein the formulation does not contain an amount of a preservative that is toxic to one or more tissues of the eye. Described herein are liquid formulations comprising a therapeutic agent sensitive to one or more components of the air, wherein the formula strength is at least 70% for at least 8 months at 5° C., at least 80% for at least 8 months at 5° C., at least 90% for at least 8 months at 5° C. and wherein the formulation does not contain an amount of a preservative that is toxic to one or more tissues of the eye.

Described herein are liquid formulations comprising a therapeutic agent, including but not limited to rapamycin, comprising a therapeutic agent sensitive to one or more components of the air, wherein the formulation when packaged is stable for at least about 3 months at 25° C. and 60% relative humidity, and wherein the formulation does not comprise an amount of an antioxidant that is toxic to one or more tissues of the eye. In some variations, the formulation when packaged is stable for at least about 12 months at 5° C. In some variations, the formulation when packaged is stable for at least about 12 months at −20° C.

In some variations, the formulation strength is at least 60% for at least 1 week, 2 weeks, 1 month, and 2 months at 25° C. and 60% relative humidity. In some variations, the formulation strength is at least 80% for at least 1 week, 2 weeks, 1 month, 2 months, 3 months, 4 months, 8 months, 10 months, 12 months, 14 months, 16 months, 18 months, 20 months, 22 months, or 24 months at 25° C. and 60% relative humidity. In some variations, the formulation strength is at least 90% for at least 1 week, 2 weeks, 1 month, 2 months, 3 months, 4 months, 8 months, 10 months, 12 months, 14 months, 16 months, 18 months, 20 months, 22 months, or 24 months at 25° C. and 60% relative humidity.

In some variations, the formulation strength is at least 60% for a period of at least 1 week, 2 weeks, 1 month, 2 months, 3 months, 4 months, 8 months, 10 months, 12 months, 14 months, 16 months, 18 months, 20 months, 22 months, or 24 months at 5° C. In some variations, the formulation strength is at least 80% for a period of at least 1 week, 2 weeks, 1 month, 2 months, 4 months, 8 months, 10 months, 12 months, 14 months, 16 months, 18 months, 20 months, or 24 at 5° C. In some variations, the formulation strength is at least 90% for a period of at least 1 week, 2 weeks, 1 month, 2 months, 4 months, 8 months, 10 months, 12 months, 14 months, 16 months, 18 months, 20 months, 22 months, or 24 months at 5° C.

In some variations, the formulation strength is at least 60% for a period of at least 1 week, 2 weeks, 1 month, 2 months, 4 months, 8 months, 10 months, 12 months, 14 months, 16 months, 18 months, 20 months, or 24 at −20° C. In some variations, the formulation strength is at least 80% for a period of at least 1 week, 2 weeks, 1 month, 2 months, 4 months, 8 months, 10 months, 12 months, 14 months, 16 months, 18 months, 20 months, 22 months, or 24 months at −20° C. In some variations, the formulation strength is at least 90% for a period of at least 1 week, 2 weeks, 1 month, 2 months, 4 months, 8 months, 10 months, 12 months, 14 months, 16 months, 18 months, 20 months, 22 months, or 24 months at −20° C.

In some variations, the liquid formulation is a stable pharmaceutical formulation. In some variations the liquid formulation is sterile.

In some variations the liquid formulations described herein are prepared by a process including one or more of sonicating, evaporating, sparging with an inert gas, heating, centrifuging or blanketing with an inert gas one or more components of the liquid formulation with an inert gas.

In some variations the stable formulations or pharmaceutical formulations when administered intraocularly or periocularly delivers an amount of therapeutic agent effective to treat, prevent, or delay onset of a disease or condition of the eye.

In some variations the liquid formulation when administered intraocularly or periocularly delivers an amount of therapeutic agent effective to treat, prevent, or delay onset of a disease or condition of the eye for a time period of at least 30 days following administration of the liquid formulation.

In some variations the liquid formulation is a solution, suspension, emulsion, self-emulsifying formulation, gel, or in situ gelling formulation in a liquid medium.

In some variations the container is designed to minimize the surface area to volume ratio for a fill volume of less than about 50 μl.

In some variations, the liquid formulations described herein have a head space volume to liquid formulation volume ratio of no greater than 1.5. In some variations the ratio of the head space volume to liquid formulation volume is no greater than 0.5.

In some variations, the liquid formulations described herein have no greater than 1 μl of oxygen in the head space per milligram of the active agent in the liquid formulation. In some variations the liquid formulations have no greater than 0.5 μl of oxygen in the head space per milligram of the active agent in the liquid formulation. In some variations the liquid formulations have no greater than 0.25 μl of oxygen in the head space per milligram of the active agent in the liquid formulation. In some variations the liquid formulations have no greater than 0.09 μl of oxygen in the head space per milligram of the active agent in the liquid formulation.

In some variations the container comprising the liquid formulation is surrounded by a secondary packaging which reduces the amount of light to which the liquid formulation is exposed.

Provided herein are unit dosage forms comprising a liquid formulation as described herein. In some variations the unit dosage form is in a prefilled syringe.

In some variations the therapeutic agent is an immunophilin binding compound, including but not limited to rapamycin, SDZ-RAD, tacrolimus, everolimus, pimecrolimus, CCI-779, AP23841, ABT-578, and prodrugs, analogs, derivatives, salts and esters thereof. In some variations the therapeutic agent is rapamycin.

In some variations the stable formulations or pharmaceutical formulations described herein comprise any of the liquid formulations recited in Table 2.

In some variations the disease or condition of the eye being treated, prevented, or having the onset delayed is angiogenesis. In some variations the angiogenesis is choroidal neovascularization.

Provided herein are methods of preparing a stable formulation comprising one or more formulation components that are sensitive to one or more air components, wherein the method comprises reducing the exposure of the one or more formulation components to the one or more air components, wherein the method does not comprise the addition of a level of and antioxidant or preservative that is toxic to the eye.

In some variations the method comprises any one or more of sonicating, sparging with an inert gas, heating, centrifuging, or blanketing with an inert gas one or more components of the liquid formulation with an inert gas. In some variations the one or more components of the air to which the one or more components of the stable formulation are sensitive to is oxygen. In some variations the inert gas is a noble gas. In some variations the noble gas is nitrogen. In some variations the method comprises any two or more of sonicating one or more components of the liquid formulation, sparging one or more components of the liquid formulation with an inert gas, or blanketing one or more components of the liquid formulation with an inert gas. In some variations the method comprises sonicating one or more components of the liquid formulation, sparging one or more components of the liquid formulation with an inert gas, and blanketing one or more components of the liquid formulation with an inert gas.

In some variations the stable formulation is a stable pharmaceutical formulation.

Provided herein are methods for treating, preventing, or delaying the onset of a disease or condition of the eye in a subject, including but not limited to a human subject, the method comprising administering to the eye of the subject a stable formulation or pharmaceutical formulation as described herein. In some variations the disease or condition of the eye is a choroidal neovascularization, AMD, uveitis, allergic conjunctivitis, dry eye, glaucoma, retinitis pigmentosa, central retinal vein occlusive disease, retinal vascular disease, macular edema, iris neovascularization, diabetic retinopathy, corneal neovascularization, or corneal graft rejection. In some variations the disease or condition of the eye is age related macular degeneration in a human subject, and the therapeutic agent comprises rapamycin, wherein the liquid formulation is administered to a position in or proximate to an eye of the subject. In some variations the liquid formulation delivers a therapeutically effective amount of rapamycin to the human subject for an extended period of time following administration. In some variations the liquid formulation delivers a therapeutically effective amount of rapamycin to the human subject for a time period of at least 30 days following administration. In some variations the liquid formulation is a solution, suspension or emulsion of rapamycin in a liquid medium. In some variations the stable pharmaceutical formulation is administered to a member from the group consisting of the vitreous, conjunctiva, between the sclera and conjunctiva, in or proximal to the sclera, subtenon, retrobulbar, and posterior juxtascleral. In some variations the liquid formulation is administered to the vitreous of the eye of the human subject. In some variations the liquid formulation is administered between the sclera and the conjunctiva of the eye of the human subject. In some variations the liquid formulation is administered to an eye having visual acuity of at least about 20/40. In some variations the age related macular degeneration is wet age related macular degeneration. In some variations the age related macular degeneration is dry age related macular degeneration. In some variations the subject is a human subject.

TABLE 1 describes variations of results of various process elements on the stability of rapamycin over time.

TABLE 2 describes nonlimiting examples of formulations that may be prepared by the methods described herein.

TABLE 3 summarizes the treatment groups, their average percent oxygen in the head space and dissolved gases, and percent formula strength at 1 week, 2 weeks, 1 month, and 2 months.

TABLE 4 shows the formulation strength, head space to fill volume ratios and amount of oxygen per amount of rapamycin (sirolimus) over time data on which FIGS. 6A, 6B, 7A, 7B, 8A and 8B are based.

Figure 6:
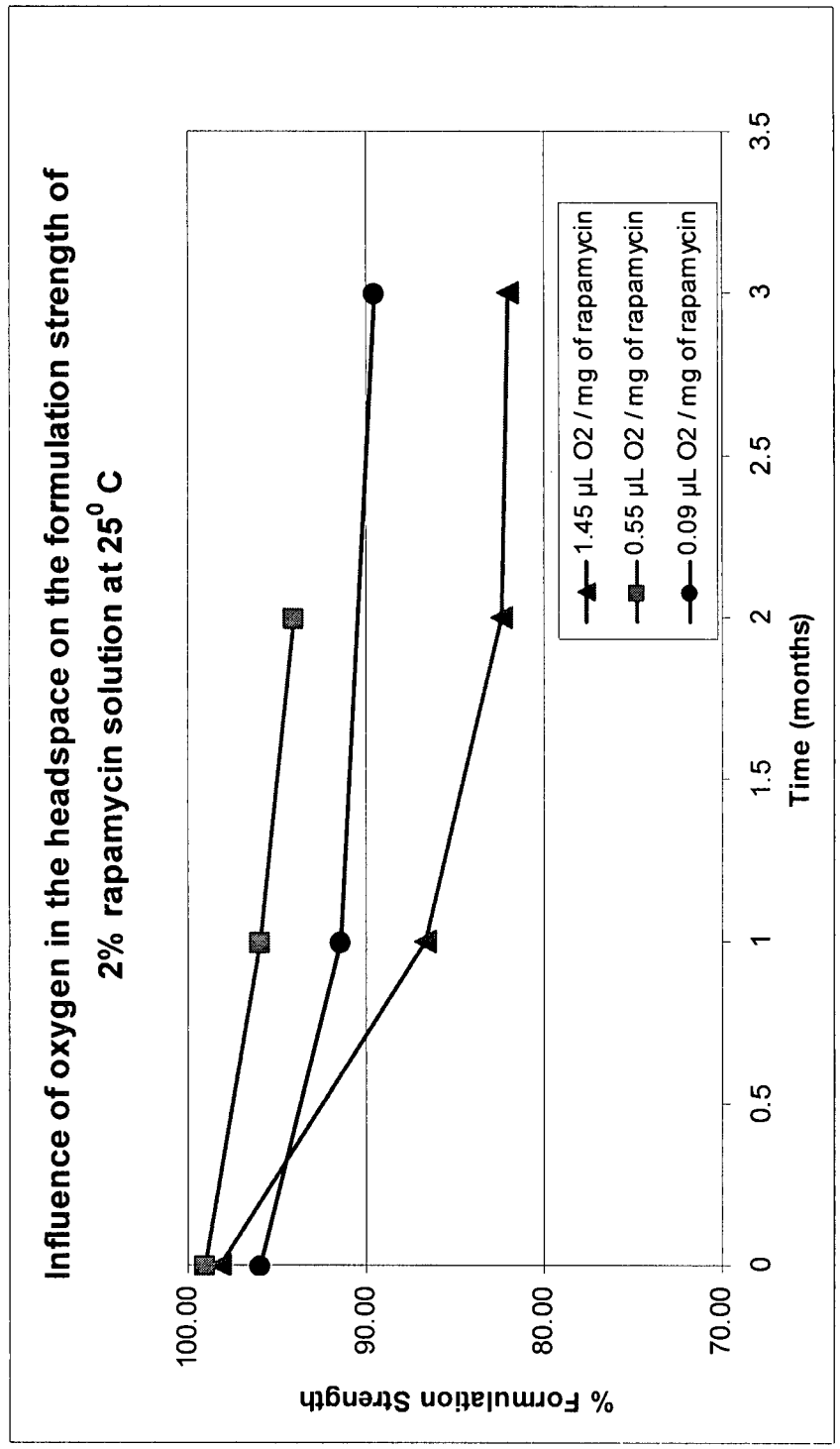
FIG. 6A shows the influence of the amount of oxygen in the head space on the formula strength of a 2% rapamycin solution at 25° C.
FIG. 6B shows the influence of the head space to fill volume ratio (HS/FV) on the formulation strength of a 2% rapamycin solution at 25° C.
FIG. 6C shows the influence of the amount of oxygen in the head space on the formula strength of a 2% rapamycin solution at 25° C.
Figure 6:
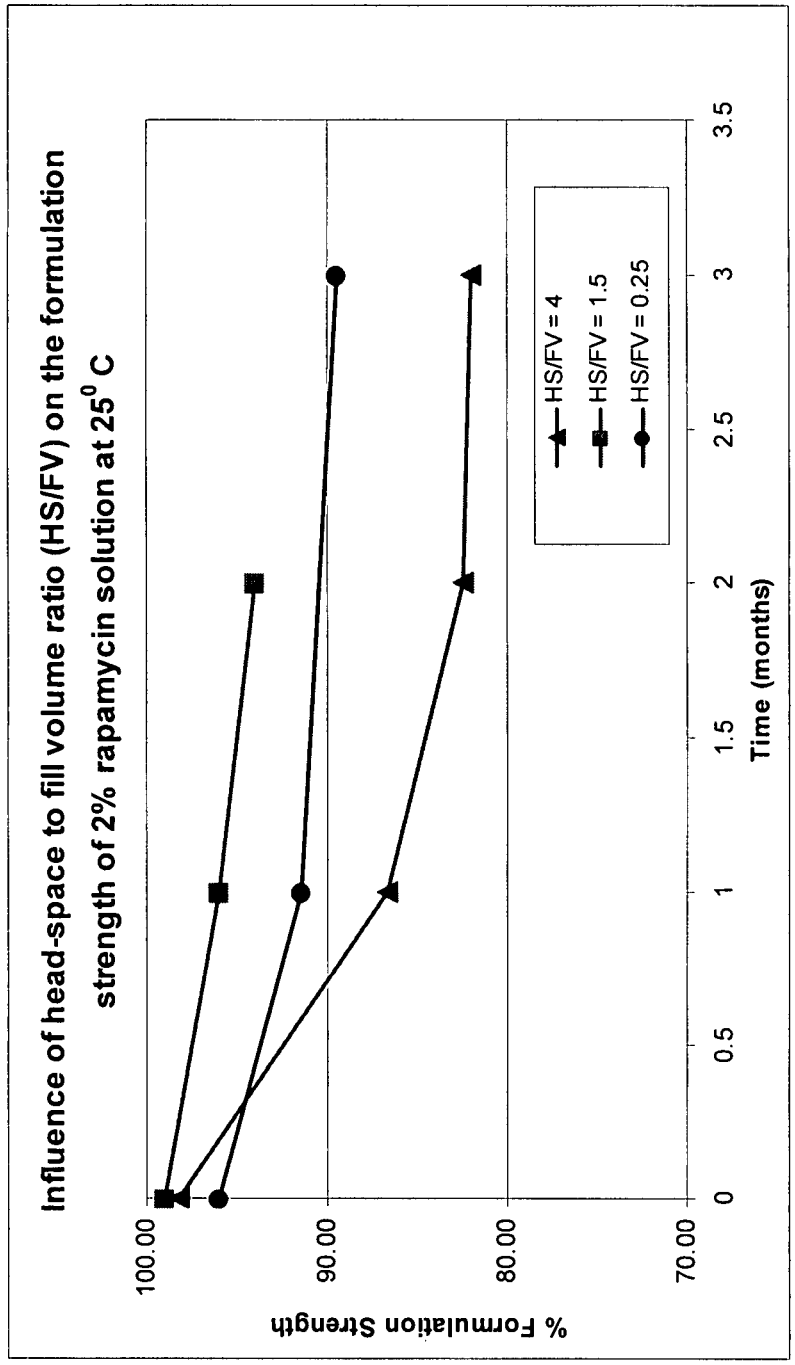
Figure 6:
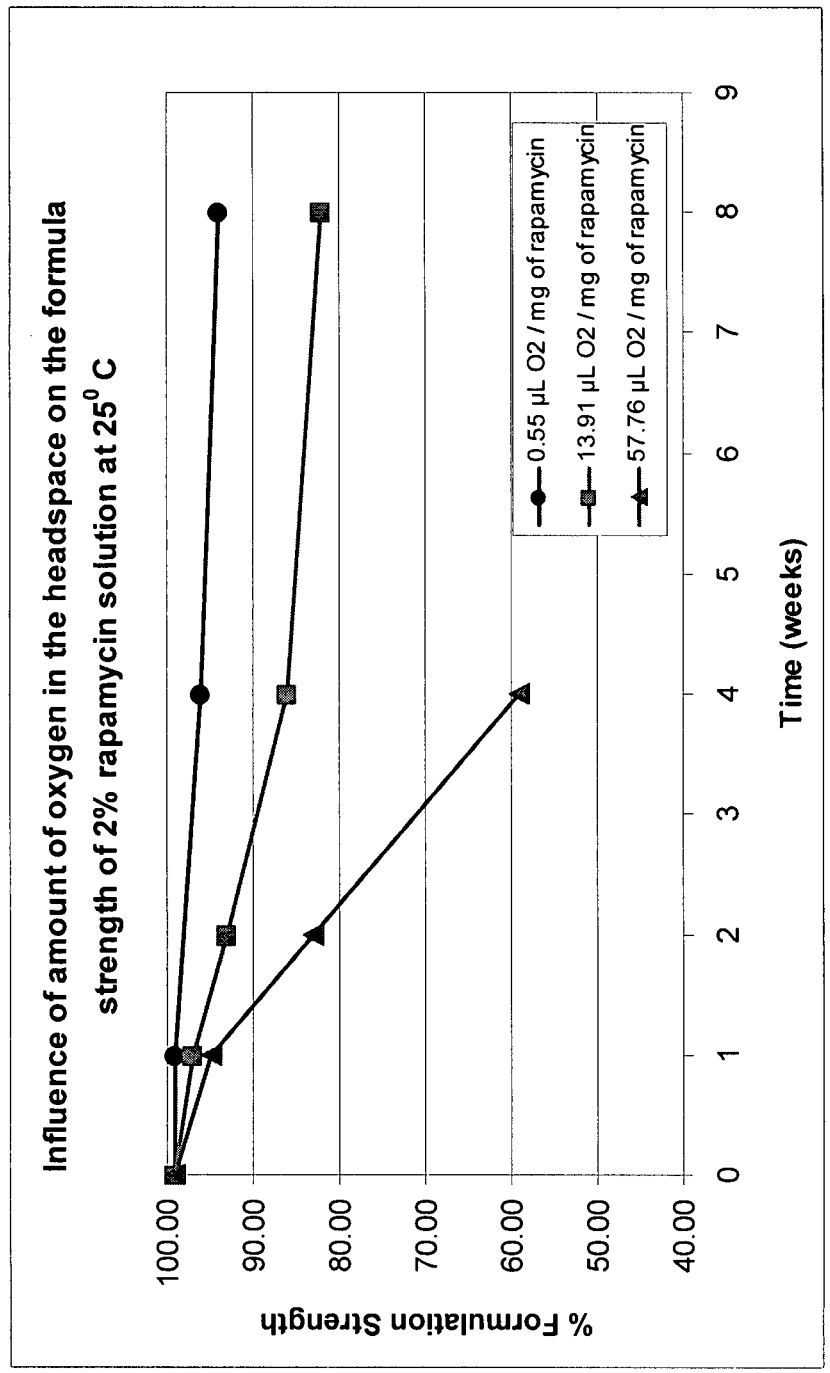

TABLE 5 shows the shows the formulation strength, percent of oxygen in the head space and amount of oxygen per amount of rapamycin (sirolimus) over time data on which FIG. 6C is based.

DETAILED DESCRIPTION

Described herein are formulations, pharmaceutical formulations, unit dose forms, kits, and methods of preparing and using the stable formulations described herein. These stable formulations and pharmaceutical formulations may be prepared by one or more of the processes described herein. In some variations the stable formulations comprise one or more components that are sensitive to one or more components of the air. In some variations the therapeutic agent is sensitive to one or more components of the air, including but not limited to oxygen. In some variations the therapeutic agent is rapamycin.

In some variations the stable formulations and pharmaceutical formulations described herein are used for the treatment, prevention, inhibition, delaying onset of, or causing regression of one or more diseases and conditions described herein, including but not limited to diseases or conditions of the eye, including but not limited to diseases or conditions of the posterior segment. In some variations the diseases or conditions include one or more of choroidal neovascularization; macular degeneration; age-related macular degeneration, including wet age-related macular degeneration ("AMD") and dry AMD; retinal angiogenesis; chronic uveitis; and other retinoproliferative conditions.

Herein are described (I) stable formulations, (2) nonlimiting examples of therapeutic agents for use in stable formulations, (3) components of stable formulations, (4) pharmaceutical formulations, (5) methods for preparing and packaging liquid formulations of therapeutic agents, (6) nonlimiting examples of diseases and conditions that may be treated, prevented, inhibited, onset delayed, or regression caused by delivery of the therapeutic agents, (7) routes of administration for delivery of the liquid formulations, and (8) treatment of CNV and wet AMD by delivery of rapamycin to a subject, including but not limited to a human subject, or to the eye of a subject using the stable formulations and pharmaceutical formulations described herein.

The term "about," as used herein, refers to the level of accuracy that is obtained when the methods described herein, such as the methods in the examples, are used.

Stable Formulations and Pharmaceutical Formulations

Unless the context clearly indicates otherwise, any of the formulations or pharmaceutical formulations described herein are preparable by the methods described herein.

Unless the context clearly indicates otherwise, any formulations or pharmaceutical formulations prepared as described herein are stable as described herein. Nonlimiting examples of the stable formulations and pharmaceutical formulations described herein are stable solutions, emulsion, self-emulsifying formulations, gelling formulations, in situ gelling formulations, suspensions, or nanosuspensions. Nonlimiting examples of stable nonliquid formulations include non-liquid or solid dosage formulations, including but not limited to polymer implants or tablets. Unless the context clearly indicates otherwise, any liquid formulations may be made stable by modifying any one or more of the level of dissolved nitrogen or oxygen to a level as is described herein. Unless the context clearly indicates otherwise, any liquid formulations may be made stable by modifying any one or more of the level of nitrogen or oxygen in the head space gases to a level as is described herein. Unless the context clearly indicates otherwise, any liquid formulations may be made stable by modifying the ratio of the head space to the fill volume as described herein. Unless the context clearly indicates otherwise, any liquid formulations may be made stable by modifying the microliters of an element, including but not limited to the amount of oxygen gas in the head space per milligram of a formulation component, including but not limited to the milligrams of an active agent such as rapamycin, in the liquid formulations described herein. Unless the context clearly indicates otherwise, any of the formulations shown in Table 2 may be made to be a stable formulation as described herein if prepared by one or more steps of the methods described herein, and any of the stable formulations described herein may be used in the methods described herein. Table 2 listed formulations are denoted as one or more of solutions ("S"), suspensions ("SP"), in situ gelling formulations ("ISG"), or self-emulsifying formulations (SEF). Elaboration of these formulations may be found, for example, in copending Ser. No. 11/351,761, filed Feb. 9, 2006, titled LIQUID FORMULATIONS FOR TREATMENT OF DISEASES OR CONDITIONS and U.S. 60/664,040, filed Feb. 9, 2005, titled LIQUID FORMULATIONS FOR TREATMENT OF DISEASES OR CONDITIONS, each of which is incorporated herein by reference in its entirety.

A "stable formulation," as described herein, is a formulation containing a therapeutic agent, wherein the formulation retains at least about 60% formula strength agent after a period of storage relative to when it was just prepared; put another way, a stable formulation is a formulation containing a therapeutic agent, wherein at least about 60% of the formulation strength remains relative to the starting level of the therapeutic agent when it was just prepared. In some variations the stable formulations described herein retain at least about 60%, at least about 65%, at least about 70%, at least about 75%, at least about 80%, at least about 85%, at least about 90%, at least about 92%, at least about 94%, at least about 95%, at least about 96%, at least about 98%, or at least about 99% of the level of the therapeutic agent after a period of storage, relative to the starting level of the therapeutic agent in the formulation. In some variations the formulation is stable for a period of storage of at least about 1 month, at least about 2 months, at least about 3 months, at least about 4 months, at least about 5 months, at least about 6 months, at least about 7 months, at least about 8 months, at least about 9 months, at least about 12 months, at least about 18 months, or at least about 24 months. In some variations the formulation comprises rapamycin, or a prodrug, analog, derivative, salt or ester thereof. In some variations the stable formulation comprises rapamycin.

A "stable pharmaceutical formulation," as described herein, is a formulation containing a therapeutic agent that retains at least about 90% of the level of the therapeutic agent after a period of storage, relative to the starting level of the therapeutic agent in the pharmaceutical formulation. In some variations the pharmaceutical formulation is stable for a period of storage of at least about 1 month, at least about 2 months, at least about 3 months, at least about 4 months, at least about 5 months, at least about 6 months, at least about 7 months, at least about 8 months, at least about 9 months, at least about 12 months, at least about 18 months, or at least about 24 months. In some variations the stable pharmaceutical formulation comprises rapamycin, or a prodrug, analog, derivative, salt or ester thereof. In some variations the stable pharmaceutical formulation comprises rapamycin.

In some variations, the stable formulations and stable pharmaceutical formulations described herein are stable when stored for a period of time at any one or more of 5° C., 25° C., or −20° C.

The stable formulations and stable pharmaceutical formulations described herein may generally be made by any method capable of producing the formulations and pharmaceutical formulations described herein, including without limitation by one or more of the methods described herein. In some variations, the stable formulations and stable pharmaceutical formulations described herein are made stable solely by the process used for their preparation and storage.

As used herein, an "ophthalmically acceptable" formulation is a formulation without a level of one or more components which causes a clinically unacceptable degree of irritation to the eye. Nonlimiting examples of such irritation include burning, irritation, itching, redness, swelling, and discharge. Those of skill in the art are able to determine whether a formulation causes an unacceptable level of irritation to the eye. In some variations, the ophthalmically acceptable formulations described herein cause no detectable irritation to the eye.

In some variations, the stable formulations and stable pharmaceutical formulations described herein do not contain levels of one or more of the antioxidants, preservatives or chemical stabilizers used in previously described stable formulations and stable pharmaceutical formulations that are toxic to the eye. In some variations, the stable formulations and stable pharmaceutical formulations described herein do not contain any of the preservatives, antioxidants or chemical stabilizers used in previously described stable formulations and stable pharmaceutical formulations that are toxic to the eye. Such antioxidants include but are not limited to ascorbic acid, citric acid, sodium sulfite, disodium EDTA, dithiothreitol (DTT), fumaric acid, beta hydroxyanisole (BHA), propyl gallate, alpha and beta tocopherols, toluene solfonic acid, tartaric acid, thioglycerol, thiourea, sodium formaldehyde sulfoxylate, sodium thiosulfate, glutamic acid, butylated hydroxytoluene (BHT), ascorbyl palmitate, benzyl alcohol, benzalkonium chloride, and maleic acid. In some variations, the stable formulations and stable pharmaceutical formulations described herein do not contain levels of either or both of BHT or ascorbyl palmitate that are toxic to the eye. In some variations, the stable formulations and stable pharmaceutical formulations described herein do not contain any preservatives, antioxidants or chemical stabilizers. In some variations, the stable formulations and stable pharmaceutical formulations described herein do not contain any BHT or ascorbyl palmitate. Described herein are preservative-free, stable ocular formulations. Described herein are preservative-free, stable ocular pharmaceutical formulations.

In some variations the stable formulations and pharmaceutical formulations described herein have a level of nitrogen or other inert or noble gas that is obtained or obtainable when a formulation is prepared by one or more of the methods described herein.

In some variations the stable formulations and pharmaceutical formulations described herein have a level of oxygen or other element of the air that is obtained or obtainable when a formulation is prepared by one or more of the methods described herein. In some variations the stable formulations and pharmaceutical formulations described herein have a level of dissolved oxygen that is reduced relative to that found in a formulation that has not been sparged or blanketed with nitrogen. In some variations the stable formulations and pharmaceutical formulations have a level of dissolved oxygen that is obtained or obtainable when the formulation is prepared using one or more of the methods described herein.

In some variations, the level of dissolved oxygen in a formulation that has not been sparged with nitrogen or other noble gas is about 5 to about 9 ppm.

In some variations, the level of dissolved oxygen in a formulation that has been sparged with nitrogen or other noble gas is less than about 95%, about 90%, about 80%, about 70%, about 60%, about 50%, about 40%, about 30%, about 20%, or about 10% of the level of dissolved oxygen in a formulation that has not been sparged with nitrogen or other noble gas.

Described herein are liquid formulations having a In some variations, the liquid formulations described herein have a head space volume to liquid formulation volume ratio of no greater than 4.0, no greater than 3.5, no greater than 3.0, no greater than 2.5, no greater than 2.0, no greater than 1.5, no greater than 1.0, no greater than 0.5, no greater than 0.25, no greater than 0.2, or no greater than 0.1. In some variations the head space volume to liquid formulation volume ratio is no greater than 1.5. In some variations the head space volume to liquid formulation volume ratio is no greater than 1.0. In some variations the ratio of the head space volume to liquid formulation volume is no greater than 0.5. In some variations the head space volume to liquid formulation volume ratio is no greater than 0.25.

Described herein are liquid formulations wherein the amount of an element that decreases the formulation strength over time is kept below a specified level, so as to maintain the formulation strength for a longer period of time. In some variations the elements is kept below a certain amount per milligram of a formulation component. In some variations the formulation component is an active agent. In some variations the element that decreases the formulation strength over time is oxygen.

Described herein are liquid formulations having no greater than 13 µl, no greater than 12 µl, no greater than 11 µl, no greater than 10 µl, no greater than 9 µl, no greater than 8 µl, no greater than 7 µl, no greater than 6 µl, no greater than 5 µl, no greater than 4 µl, no greater than 3 µl, no greater than 2 µl, no greater than 1.45 µl, no greater than 1 µl, no greater than 0.75 µl, no greater than 0.55 µl, no greater than 0.5 µl, no greater than 0.25 µl, no greater than 0.2 µl, no greater than 0.1 µl, no greater than 0.09 µl, no greater than 0.05 µl, no greater than 0.03 µl, no greater than 0.01 µl, or no greater than 0.001 µl of oxygen in the head space per milligram of the active agent in the liquid formulation In some variations, the liquid formulations described herein have no greater than 1.45 µl of oxygen in the head space per milligram of the active agent in the liquid formulation. In some variations, the liquid formulations described herein have no greater than 1 µl of oxygen in the head space per milligram of the active agent in the liquid formulation. In some variations the liquid formulations have no greater than 0.55 µl of oxygen in the head space per milligram of the active agent in the liquid formulation. In some variations the liquid formulations have no greater than 0.5 µl of oxygen in the head space per milligram of the active agent in the liquid formulation. In some variations the liquid formulations have no greater than 0.25 µl of oxygen in the head space per milligram of the active agent in the liquid formulation. In some variations the liquid formulations have no greater than 0.09 µl of oxygen in the head space per milligram of the active agent in the liquid formulation.

Described herein are liquid formulations comprising a therapeutic agent, including but not limited to an immunophilin binding compound or rapamycin, comprising a level of nitrogen in the dissolved gases of greater than 80%, greater than 85%, greater than 90% or greater than 95%.

Described herein are sealed vessels comprising a liquid formulation comprising an immunophilin binding compound, wherein the liquid formulation is in contact with a head space gas having no greater than 20% oxygen gas, no greater than 15% oxygen gas, no greater than 10% oxygen gas, or no greater than 5% oxygen gas.

Described herein are sealed vessels comprising a liquid formulation comprising an immunophilin binding compound, wherein the liquid formulation is in contact with a head space gas having greater than 80% nitrogen gas, greater than 85% nitrogen gas, greater than 90% nitrogen gas, or greater than 95% nitrogen gas.

In some variations the stable formulations and pharmaceutical formulations described herein comprise rapamycin and have a level of oxygen or other element of the air that is obtained or obtainable when a formulation is prepared by one or more of the methods described herein. In some variations the stable formulations and pharmaceutical formulations described herein comprise rapamycin and have a level of dissolved oxygen that is reduced relative to that found in a formulation that has not been sparged or blanketed with nitrogen. In some variations the stable formulations and pharmaceutical formulations comprise rapamycin and have a level of dissolved oxygen that is obtained or obtainable when the formulation is prepared using one or more of the methods described herein. In some variations, the level of dissolved oxygen in a rapamycin-containing formulation that has not been sparged with nitrogen or other noble gas is about 5 to about 9 ppm. In some variations, the level of dissolved oxygen in a rapamycin-containing formulation that has been sparged with nitrogen or other noble gas is less than about 95%, about 90%, about 80%, about 70%, about 60%, about 50%, about 40%, about 30%, about 20%, or about 10% of the level of dissolved oxygen in a rapamycin-containing formulation that has not been sparged with nitrogen or other noble gas.

In some variations the stable formulations and pharmaceutical formulations described herein have a level of dissolved nitrogen that is greater than that found in a formulation that has not been sparged or blanketed with nitrogen. In some variations the stable formulations and pharmaceutical formulations have a level of dissolved nitrogen that is obtained or obtainable when the formulation is prepared using one or more of the methods described herein.

Described herein are liquid formulations comprising a therapeutic agent, including but not limited to an immunophilin binding compound such as rapamycin, the liquid formulation having a percent of oxygen in the dissolved gases of no greater than 20%. In some variations, the liquid formulations described herein have a percent of oxygen in the dissolved gases of no greater than 19.5%, no greater than 19%, no greater than 18.5%, no greater than 18%, no greater than 17.5%, no greater than 17%, no greater than 16.5%, no greater than 16%, no greater than 15%, no greater than 13%, no greater than 11%, no greater than 9%, no greater than 7%, no greater than 5%, no greater than 3%, or no greater than 1%.

In some variations the liquid formulations described herein comprise an immunophilin binding compound and have a percent of oxygen in the dissolved gases of no greater than 18%. In some variations the liquid formulations described herein comprise rapamycin and have a percent of oxygen in the dissolved gases of no greater than 18%.

In some variations the liquid formulations described herein comprise an immunophilin binding compound and have a percent of oxygen in the dissolved gases of no greater than 16.5%. In some variations the liquid formulations described herein comprise rapamycin and have a percent of oxygen in the dissolved gases of no greater than 16.5%.

In some variations the liquid formulations described herein comprise an immunophilin binding compound and have a percent of oxygen in the dissolved gases of no greater than 15%. In some variations the liquid formulations described herein comprise rapamycin and have a percent of oxygen in the dissolved gases of no greater than 15%.

In some variations the liquid formulations described herein comprise an immunophilin binding compound and have a percent of oxygen in the dissolved gases of no greater than 10%. In some variations the liquid formulations described herein comprise rapamycin and have a percent of oxygen in the dissolved gases of no greater than 10%.

Described herein are sealed vessels comprising a liquid formulation comprising a therapeutic agent, including but not limited to an immunophilin binding compound or rapamycin, wherein the liquid formulation is in contact with a head space gas having no greater than 20% oxygen gas. In some variations the liquid formulation is in contact with a head space gas having no greater than 15% oxygen gas. In some variations the liquid formulation is in contact with a head space gas having no greater than 10% oxygen gas. In some variations the liquid formulation is in contact with a head space gas having no greater than 5% oxygen gas. In some variations the therapeutic agent is an immunophilin binding compound. In some variations the therapeutic agent is rapamycin.

As used herein, "formula strength" refers to the weight percent of a therapeutic agent present in the formulation at a given time, relative to the weight of the therapeutic agent present in the formulation when it has just been prepared.

Described herein are ophthalmically acceptable liquid formulation comprising a therapeutic agent, wherein the formula strength is at least 60% after 1 week of storage at one or more of −20° C., 5° C., or 25° C. In some variations the formula strength is at least 65%, at least 70%, at least 75%, at least 80%, at least 85%, at least 95%, at least 96%, at least 97%, at least 98%, or at least 99%. In some variations the therapeutic agent is an immunophilin binding compound, or a prodrug, analog, derivative, salt or ester thereof. In some variations the therapeutic agent is rapamycin. Described herein are ophthalmically acceptable liquid formulations comprising rapamycin, wherein the formula strength is at least 70% after 1 week of storage at one or more of −20° C., 5° C., or 25° C. Described herein are ophthalmically acceptable liquid formulations comprising rapamycin, wherein the formula strength is at least 80% after 1 week of storage at one or more of −20° C., 5° C., or 25° C. Described herein are ophthalmically acceptable liquid formulations comprising rapamycin, wherein the formula strength is at least 90% after 1 week of storage at one or more of −20° C., 5° C., or 25° C. Described herein are ophthalmically acceptable liquid formulations comprising rapamycin, wherein the formula strength is at least 95% after 1 week of storage at one or more of −20° C., 5° C., or 25° C.

Described herein are ophthalmically acceptable liquid formulations wherein the formula strength is at least 65%, at least 70%, at least 75%, at least 80%, at least 85%, at least 95%, at least 96%, at least 97%, at least 98%, or at least 99% after 2 weeks of storage at one or more of −20° C., 5° C., or 25° C. In some variations the therapeutic agent is an immunophilin binding compound, or a prodrug, analog, derivative, salt or ester thereof. In some variations the therapeutic agent is rapamycin.

Described herein are ophthalmically acceptable liquid formulations wherein the formula strength is at least 65%, at least 70%, at least 75%, at least 80%, at least 85%, at least 95%, at least 96%, at least 97%, at least 98%, or at least 99% after 1 month of storage at one or more of −20° C., 5° C., or 25° C. In some variations the therapeutic agent is an immunophilin binding compound, or a prodrug, analog, derivative, salt or ester thereof. In some variations the therapeutic agent is rapamycin.

Described herein are ophthalmically acceptable liquid formulations comprising a therapeutic agent, wherein the formula strength is at least 80% after 2 months of storage at one or more of −20° C., 5° C., or 25° C. Described herein are ophthalmically acceptable liquid formulations comprising an immunophilin binding compound, or a prodrug, analog, derivative, salt or ester thereof, wherein the formula strength is at least 80% after 2 months of storage at one or more of −20° C., 5° C., or 25° C. Described herein are ophthalmically acceptable liquid formulations comprising rapamycin, wherein the formula strength is at least 80% after 2 months of storage at one or more of −20° C., 5° C., or 25° C.

Described herein are ophthalmically acceptable liquid formulations comprising a therapeutic agent, wherein the formula strength is at least 90% after 2 months of storage at one or more of −20° C., 5° C., or 25° C. Described herein are ophthalmically acceptable liquid formulations comprising an immunophilin binding compound, or a prodrug, analog, derivative, salt or ester thereof, wherein the formula strength is at least 90% after 2 months of storage at one or more of −20° C., 5° C., or 25° C. Described herein are ophthalmically acceptable liquid formulations comprising rapamycin, wherein the formula strength is at least 90% after 2 months of storage at one or more of −20° C., 5° C., or 25° C.

Described herein are ophthalmically acceptable liquid formulations comprising a therapeutic agent, wherein the formula strength is at least 80% after 8 months of storage at one or more of −20° C. or 5° C. Described herein are ophthalmically acceptable liquid formulations comprising an immunophilin binding compound, or a prodrug, analog, derivative, salt or ester thereof, wherein the formula strength is at least 80% after 8 months of storage at one or more of −20° C. or 5° C. Described herein are ophthalmically acceptable liquid formulations comprising rapamycin, wherein the formula strength is at least 80% after 8 months of storage at one or more of −20° C. or 5° C., or 25° C.

Described herein are ophthalmically acceptable liquid formulations comprising a therapeutic agent, wherein the formula strength is at least 90% after 8 months of storage at one or more of −20° C. or 5° C. Described herein are ophthalmically acceptable liquid formulations comprising an immunophilin binding compound, or a prodrug, analog, derivative, salt or ester thereof, wherein the formula strength is at least 90% after 8 months of storage at one or more of −20° C. or 5° C. Described herein are ophthalmically acceptable liquid formulations comprising rapamycin, wherein the formula strength is at least 90% after 8 months of storage at one or more of −20° C. or 5° C., or 25° C.

Described herein are liquid formulations comprising a therapeutic agent sensitive to one or more components of the air, wherein the formula strength is at least 70% for a period of at least about 1 week, 2 weeks, 1 month, or 2 months at 25° C. and 60% relative humidity, and wherein the formulation does not contain an amount of a preservative that is toxic to one or more tissues of the eye. In some variations the formula strength is at least 75%, at least 80%, at least 85%, at least 90%, or at least 95% for at least 2 weeks at 25° C. and 60% relative humidity. Described herein are liquid formulations comprising a therapeutic agent sensitive to one or more components of the air, wherein the formula strength of the therapeutic agent is at least 70%, at least 75%, at least 80%, at least 85%, at least 90%, or at least 95%, for at least 1 month. Described herein are liquid formulations comprising a therapeutic agent sensitive to one or more components of the air, wherein the formula strength of the therapeutic agent is at least 70%, at least 75%, at least 80%, at least 85%, at least 90%, or at least 95% at 25° C. and 60% relative humidity, for at least 2 months.

In some variations the liquid formulations described herein have a formula strength of at least 80% for a period of at least about 2, 3 months, 4 months, 5 months, 6 months, 7 months, 8 months, 9 months, 10 months, 11 months, 12 months, 14 months, 16 months, 18 months, 20 months, 22 months, or 24 months at 5° C. In some variations the liquid formulations described herein have a formula strength of at least 90% for a period of at least about 2, 3 months, 4 months, 5 months, 6 months, 7 months, 8 months, 9 months, 10 months, 11 months, 12 months, 14 months, 16 months, 18 months, 20 months, 22 months, or 24 months at 5° C. In some variations the liquid formulations described herein have a formula strength of at least 95% for a period of at least about 2 months, 3 months, 4 months, 5 months, 6 months, 7 months, 8 months, 9 months, 10 months, 11 months, 12 months, 14 months, 16 months, 18 months, 20 months, 22 months, or 24 months at 5° C.

In some variations the liquid formulations described herein have a formula strength of at least 80% for a period of at least about 2, 3 months, 4 months, 5 months, 6 months, 7 months, 8 months, 9 months, 10 months, 11 months, 12 months, 14 months, 16 months, 18 months, 20 months, 22 months, or 24 months at −20° C. In some variations the liquid formulations described herein have a formula strength of at least 90% for a period of at least about 2, 3 months, 4 months, 5 months, 6 months, 7 months, 8 months, 9 months, 10 months, 11 months, 12 months, 14 months, 16 months, 18 months, 20 months, 22 months, or 24 months at −20° C. In some variations the liquid formulations described herein have a formula strength of at least 95% for a period of at least about 2, 3 months, 4 months, 5 months, 6 months, 7 months, 8 months, 9 months, 10 months, 11 months, 12 months, 14 months, 16 months, 18 months, 20 months, 22 months, or 24 months at −20° C.

Therapeutic Agents

Most generally, any compound that is sensitive to one or more components of the air, heat, or light may be used in the stable formulations described herein. Unless the context indicates otherwise, any of the therapeutic agents may be used in any one or more of the formulations, pharmaceutical formulations, unit dose forms, kits, methods of preparation, and methods of use described herein. In some variations the therapeutic agent is sensitive to one or more of oxygen, heat, or light.

In some variations the stable formulations described herein comprise therapeutic agents that are useful in treating, preventing, inhibiting, delaying the onset of, or causing the regression of the diseases and conditions described herein. The following references, each of which is incorporated herein by reference in its entirety, show one or more formulations, including but not limited to rapamycin formulations, which may be made stable by the methods described herein, and which describe use of rapamycin at various doses and other therapeutic agents for treating various diseases or conditions: U.S. 60/651,790, filed Feb. 9, 2005, titled FORMULATIONS FOR OCULAR TREATMENT; U.S. 60/664,040, filed Feb. 9, 2005, titled LIQUID FORMULATIONS FOR TREATMENT OF DISEASES OR CONDITIONS; U.S. 60/664,119, filed Mar. 21, 2005, titled DRUG DELIVERY SYSTEMS FOR TREATMENT OF DISEASES OR CONDITIONS; U.S. 60/664,306, filed Mar. 21, 2005, titled IN SITU GELLING FORMULATIONS AND LIQUID FORMULATIONS FOR TREATMENT OF DISEASES OR CONDITIONS; U.S. Ser. No. 11/351,844, filed Feb. 9, 2006, titled FORMULATIONS FOR OCULAR TREATMENT; U.S. Ser. No. 11/351,761, filed Feb. 9, 2006, titled LIQUID FORMULATIONS FOR TREATMENT OF DISEASES OR CONDITIONS; U.S. Ser. No. 11/386,290, filed Mar. 21, 2006, titled DRUG DELIVERY SYSTEMS FOR TREATMENT OF DISEASES OR CONDITIONS; U.S. Ser. No. 11/352,092, filed Feb. 9, 2006, entitled RAPAMYCIN FORMULATIONS AND METHODS OF THEIR USE; U.S. 60/772,018, filed Feb. 9, 2006, titled STABLE FORMULATIONS, AND METHODS OF THEIR PREPARATION AND USE; US 2005/0187241, and US 2005/0064010.

Therapeutic agents that may be used include compounds that act by binding members of the immunophilin family of cellular proteins. Such compounds are known as "immunophilin binding compounds." Immunophilin binding compounds include but are not limited to the "limus" family of compounds. Examples of limus compounds that may be used include but are not limited to cyclophilins and FK506-binding proteins (FKBPs), including sirolimus (rapamycin) and its water soluble analog SDZ-RAD (Novartis), TAFA-93 (Isotechnika), tacrolimus, everolimus, RAD-001 (Novartis), pimecrolimus, temsirolimus, CCI-779 (Wyeth), AP23841 (Ariad), AP23573 (Ariad), and ABT-578 (Abbott Laboratories). Limus compound analogs and derivatives that may be used include but are not limited to the compounds described in U.S. Pat. Nos. 5,527,907; 6,376,517; and 6,329,386 and U.S. patent application Ser. No. 09/950,307, each of which is incorporated herein by reference in their entirety. Therapeutic agents also include analogs, prodrugs, derivatives, salts and esters of limus compounds.

The terms rapamycin, sirolimus and rapa are used interchangeably herein.

Other rapamycin derivatives that may be used include, without limitation, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy-rapamycin, 2-desmethyl-rapamycin, mono- and di-ester derivatives of rapamycin, 27-oximes of rapamycin; 42-oxo analog of rapamycin; bicyclic rapamycins; rapamycin dimers; silyl ethers of rapamycin; rapamycin arylsulfonates and sulfamates, mono-esters and di-esters at positions 31 and 42, 30-demethoxy rapamycin, and other derivatives described in Vezina et al., "Rapamycin (AY-22,989), A New Antifungal Antibiotic. I. Taxonomy Of The Producing Streptomycete And Isolation Of The Active Principle" J. Antibiot. (Tokyo) 28:721-726 (1975); Sehgal et al., "Rapamycin (AY-22,989), A New Antifungal Antibiotic. II. Fermentation, Isolation And Characterization" J. Antibiot. (Tokyo) 28:727-732 (1975); Sehgal et al., "Demethoxyrapamycin (AY-24,668), A New Antifungal Antibiotic" J. Antibiot. (Tokyo) 36:351-354 (1983); and Paiva et al., "Incorporation Of Acetate, Propionate, And Methionine Into Rapamycin By *Streptomyces hygroscopicus*" J Nat Prod 54:167-177 (1991), WO 92/05179, EP 467606, Caufield et al., "Hydrogenated Rapamycin Derivatives" U.S. Pat. No. 5,023,262; Kao et al., "Bicyclic Rapamycins" U.S. Pat. No. 5,120,725; Kao et al., "Rapamycin Dimers" U.S. Pat. No. 5,120,727; Failli et al., "Silyl Ethers Of Rapamycin" U.S. Pat. No. 5,120,842; Failli et al., "Rapamycin 42-Sulfonates And 42-(N-carboalkoxy) Sulfamates Useful As Immunosuppressive Agents" U.S. Pat. No. 5,177,203; Nicolaou et al., "Total Synthesis Of Rapamycin" J. Am. Chem. Soc. 115: 4419-4420 (1993); Romo et al., "Total Synthesis Of (−) Rapamycin Using An Evans-Tishchenko Fragment Coupling" J. Am. Chem. Soc. 115:7906-7907 (1993); and Hayward et al., "Total Synthesis Of Rapamycin Via A Novel Titanium-Mediated Aldol Macrocyclization Reaction" J. Am. Chem. Soc., 115:9345-9346 (1993), each of which is incorporated herein by reference in its entirety.

The limus family of compounds may be used in the formulations, liquid formulations and methods for the treatment, prevention, inhibition, delaying the onset of, or causing the regression of angiogenesis-mediated diseases and conditions of the eye, including choroidal neovascularization. The limus family of compounds may be used to prevent, treat, inhibit, delay the onset of, or cause regression of AMD, including wet AMD. Rapamycin may be used to prevent, treat, inhibit, delay the onset of, or cause regression of angiogenesis-mediated diseases and conditions of the eye, including choroidal neovascularization. Rapamycin and derivatives and analogs thereof may be used to prevent, treat, inhibit, delay the onset of, or cause regression of AMD, including wet AMD. In some variations, a member of the limus family of compounds or rapamycin is used to treat wet AMD or angiogenesis-mediated diseases and conditions of the eye including choroidal neovascularization.

Other therapeutic agents that may be used include those disclosed in the following patents and publications, the contents of each of which is incorporated herein in its entirety: PCT publication WO 2004/027027, published Apr. 1, 2004, titled Method of inhibiting choroidal neovascularization, assigned to Trustees of the University of Pennsylvania; U.S. Pat. No. 5,387,589, issued Feb. 7, 1995, titled Method of Treating Ocular Inflammation, with inventor Prassad Kulkarni, assigned to University of Louisville Research Foundation; U.S. Pat. No. 6,376,517, issued Apr. 23, 2003, titled Pipecolic acid derivatives for vision and memory disorders, assigned to GPI NIL Holdings, Inc; PCT publication WO 2004/028477, published Apr. 8, 2004, titled Method subretinal administration of therapeutics including steroids: method for localizing pharmadynamic action at the choroid and retina; and related methods for treatment and or prevention of retinal diseases, assigned to Innorx, Inc; U.S. Pat. No. 6,416,777, issued Jul. 9, 2002, titled Ophthalmic drug delivery device, assigned to Alcon Universal Ltd; U.S. Pat. No. 6,713,081, issued Mar. 30, 2004, titled Ocular therapeutic agent delivery device and methods for making and using such devices, assigned to Department of Health and Human Services; U.S. Pat. No. 5,100,899, issued Mar. 31, 1992, titled Methods of inhibiting transplant rejection in mammals using rapamycin and derivatives and prodrugs thereof.

Other therapeutic agents that may be used include pyrrolidine, dithiocarbamate (NFκB inhibitor); squalamine; TPN 470 analogue and fumagillin; PKC (protein kinase C) inhibitors; Tie-1 and Tie-2 kinase inhibitors; inhibitors of VEGF receptor kinase; proteosome inhibitors such as Velcade™ (bortezomib, for injection; ranibuzumab (Lucentis™) and other antibodies directed to the same target; pegaptanib (Macugen™); vitronectin receptor antagonists, such as cyclic peptide antagonists of vitronectin receptor-type integrins; α-v/β-3 integrin antagonists; α-v/β-1 integrin antagonists; thiazolidinediones such as rosiglitazone or troglitazone; interferon, including γ-interferon or interferon targeted to CNV by use of dextran and metal coordination; pigment epithelium derived factor (PEDF); endostatin; angiostatin; tumistatin; canstatin; anecortave acetate; acetonide; triamcinolone; tetrathiomolybdate; RNA silencing or RNA interference (RNAi) of angiogenic factors, including ribozymes that target VEGF expression; Accutane™ (13-cis retinoic acid); ACE inhibitors, including but not limited to quinopril, captopril, and perindozril; inhibitors of mTOR (mammalian target of rapamycin); 3-aminothalidomide; pentoxifylline; 2-methoxyestradiol; colchicines; AMG-1470; cyclooxygenase inhibitors such as nepafenac, rofecoxib, diclofenac, rofecoxib, NS398, celecoxib, vioxx, and (E)-2-alkyl-2(4-methanesulfonylphenyl)-1-phenylethene; t-RNA synthase modulator; metalloprotease 13 inhibitor; acetylcholinesterase inhibitor; potassium channel blockers; endorepellin; purine analog of 6-thioguanine; cyclic peroxide ANO-2; (recombinant) arginine deiminase; epigallocatechin-3-gallate; cerivastatin; analogues of suramin; VEGF trap molecules; apoptosis inhibiting agents; Visudyne™, snET2 and other photo sensitizers, which may be used with photodynamic therapy (PDT); inhibitors of hepatocyte growth factor (antibodies to the growth factor or its receptors, small molecular inhibitors of the c-met tytosine kinase, truncated versions of HGF e.g. NK4).

Other therapeutic agents that may be used include anti-inflammatory agents, including, but not limited to nonsteroidal anti-inflammatory agents and steroidal anti-inflammatory agents. In some variations, active agents that may be used in the liquid formulations are ace-inhibitors, endogenous cytokines, agents that influence basement membrane, agents that influence the growth of endothelial cells, adrenergic agonists or blockers, cholinergic agonists or blockers, aldose reductase inhibitors, analgesics, anesthetics, antiallergics, antibacterials, antihypertensives, pressors, antiprotozoal agents, antiviral agents, antifungal agents, anti-infective agents, antitumor agents, antimetabolites, and antiangiogenic agents.

Steroidal therapeutic agents that may be used include but are not limited to 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, and any of their derivatives.

In some variations, cortisone, dexamethasone, fluocinolone, hydrocortisone, methylprednisolone, prednisolone, prednisone, and triamcinolone, or their derivatives, may be used. The liquid formulation may include a combination of two or more steroidal therapeutic agents.

In one nonlimiting example, the steroidal therapeutic agents may constitute from about 0.05% to about 50% by weight of the liquid formulation. In another nonlimiting example, the steroid constitutes from about 0.05% to about 10%, between about 10% to about 20%; between about 30% to about 40%; or between about 40% to about 50% by weight of the liquid formulation.

Other nonlimiting examples of therapeutic agents that may be used include but are not limited to anaesthetics, analgesics, cell transport/mobility impending agents such as colchicines, vincristine, cytochalasin B and related compounds; carbonic anhydrase inhibitors such as acetazolamide, methazolamide, dichlorphenamide, diamox and neuroprotectants such as nimodipine and related compounds; antibiotics such as tetracycline, chlortetracycline, bacitracin, neomycin, polymyxin, gramicidin, cephalexin, oxytetracycline, chloramphenicol, rifampicin, ciprofloxacin, aminosides, gentamycin, erythromycin and penicillin, quinolone, ceftazidime, vancomycine imipeneme; antifungals such as amphotericin B, fluconazole, ketoconazole and miconazole; antibacterials such as sulfonamides, sulfadiazine, sulfacetamide, sulfamethizole and sulfisoxazole, nitrofurazone and sodium propionate; antivirals, such as idoxuridine, trifluorothymidine, trifluorouridine, acyclovir, ganciclovir, cidofovir, interferon, DDI, AZT, foscamet, vidarabine, irbavirin, protease inhibitors and anti-cytomegalovirus agents; antiallergenics such as sodium cromoglycate, antazoline, methapyriline, chlorpheniramine, cetirizine, pyrilamine and prophenpyridamine; synthetic gluocorticoids and mineralocorticoids and more generally hormones forms derivating from the cholesterol metabolism (DHEA, progesterone, estrogens); non-steroidal anti-inflammatories such as salicylate, indomethacin, ibuprofen, diclofenac, flurbiprofen, piroxicam and COX2 inhibitors; antineoplastics such as carmustine, cisplatin, fluorouracil; adriamycin, asparaginase, azacitidine, azathioprine, bleomycin, busulfan, carboplatin, carmustine, chlorambucil, cyclophosphamide, cyclosporine, cytarabine, dacarbazine, dactinomycin, daunorubicin, doxorubicin, estramustine, etoposide, etretinate, filgrastin, floxuridine, fludarabine, fluorouracil, florxymesterone, flutamide, goserelin, hydroxyurea, ifosfamide, leuprolide, levamisole, limustine, nitrogen mustard, melphalan, mercaptopurine, methotrexate, mitomycin, mitotane, pentostatin, pipobroman, plicamycin, procarbazine, sargramostin, streptozocin, tamoxifen, taxol, teniposide, thioguanine, uracil mustard, vinblastine, vincristine and vindesine; immunological drugs such as vaccines and immune stimulants; insulin, calcitonin, parathyroid hormone and peptide and vasopressin hypothalamus releasing factor; beta adrenergic blockers such as timolol, levobunolol and betaxolol; cytokines, interleukines and growth factors epidermal growth factor, fibroblast growth factor, platelet derived growth factor, transforming growth factor beta, ciliary neurotrophic growth factor, glial derived neurotrophic factor, NGF, EPO, PLGF, brain nerve growth factor (BNGF), vascular endothelial growth factor (VEGF) and monoclonal antibodies or fragments thereof directed against such growth factors; anti-inflammatories such as hydrocortisone, dexamethasone, fluocinolone, prednisone, prednisolone, methylprednisolone, fluorometholone, betamethasone and triamcinolone; decongestants such as phenylephrine, naphazoline and tetrahydrazoline; miotics and anti-cholinesterases such as pilocarpine, carbachol, di-isopropyl fluorophosphate, phospholine iodine and demecarium bromide; mydriatics such as atropine sulphate, cyclopentolate, homatropine, scopolamine, tropicamide, eucatropine; sympathomimetics such as epinephrine and vasoconstrictors and vasodilators, anticlotting agents such as heparin, antifibrinogen, fibrinolysin, anticlotting activase, antidiabetic agents include acetohexamide, chlorpropamide, glipizide, glyburide, tolazamide, tolbutamide, insulin and aldose reductase inhibitors, hormones, peptides, nucleic acids, saccharides, lipids, glycolipids, glycoproteins and other macromolecules include endocrine hormones such as pituitary, insulin, insulin-related growth factor, thyroid, growth hormones; heat shock proteins; immunological response modifiers such as muramyl dipeptide, cyclosporins, interferons (including alpha-, beta- and gamma-interferons), interleukin-2, cytokines, FK506 (an epoxy-pyrido-oxaazcyclotricosine-tetrone, also known as Tacrolimus), tumor necrosis factor, pentostatin, thymopentin, transforming factor beta2, erythropoetin; antineogenesis proteins (e.g. anti VEGF, interferons), antibodies (monoclonal, polyclonal, humanized, etc.) or antibodies fragments, oligoaptamers, aptamers and gene fragments (oligonucleotides, plasmids, ribozymes, small interference RNA (SiRNA), nucleic acid fragments, peptides), immunomodulators such as endoxan, thalidomide, tamoxifene; antithrombolytic and vasodilator agents such as rtPA, urokinase, plasmin; nitric oxide donors, nucleic acids, dexamethasone, cyclosporin A, azathioprine, brequinar, gusperimus, 6-mercaptopurine, mizoribine, rapamycin, tacrolimus (FK-506), folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thiaguanine), pyrimidine analogs (e.g., ancitabine, azacitidine, 6-azauridine, carmofur, cytarabine, doxifluridine, emitefur, enocitabine, floxuridine, fluorouracil, gemcitabine, tegafur) fluocinolone, triaminolone, anecortave acetate, fluorometholone, medrysone, and prednislone. In some variations the immunosuppressive agent is dexamethasone. In other variations the immunosuppressive agent is cyclosporin A.

In other variations the formulation comprises a combination of one or more therapeutic agents.

Other nonlimiting examples of therapeutic agents that may be used in the formulations described herein include antibacterial antibiotics, aminoglycosides (e.g., amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (e.g., azidamfenicol, chloramphenicol, florfenicol, thiamphenicol), ansamycins (e.g., rifamide, rifampin, rifamycin sv, rifapentine, rifaximin), P-lactams (e.g., carbacephems (e.g., loracarbef), carbapenems (e.g., biapenem, imipenem, meropenem, panipenem), cephalosporins (e.g., cefaclor, cefadroxil, cefamandole, cefatrizine, cefazedone, cefazolin, cefcapene pivoxil, cefclidin, cefdinir, cefditoren, cefepime, cefetamet, cefixime, cefinenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (e.g., cefbuperazone, cefinetazole, cefminox, cefotetan, cefoxitin), monobactams (e.g., aztreonam, carumonam, tigemonam), oxacephems, flomoxef, moxalactam), penicillins (e.g., amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin g benethamine, penicillin g benzathine, penicillin g benzhydrylamine, penicillin g calcium, penicillin g hydrabamine, penicillin g potassium, penicillin g procaine, penicillin n, penicillin o, penicillin v, penicillin v benzathine, penicillin v hydrabamine, penimepicycline, phenethicillin potassium, piperacillin, pivampicillin, propicillin, quinacillin, sulbenicillin, sultamicillin, talampicillin, temocillin, ticarcillin), other (e.g., ritipenem), lincosamides (e.g., clindamycin, lincomycin), macrolides (e.g., azithromycin, carbomycin, clarithromycin, dirithromycin, erythromycin, erythromycin acistrate, erythromycin estolate, erythromycin glucoheptonate, erythromycin lactobonate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (e.g., amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (e.g., apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin); synthetic antibacterials, 2,4-Diaminopyrimidines (e.g., brodimoprim, tetroxoprim, trimethoprim), nitrofurans (e.g., furaltadone, furazolium chloride, nifuradene, nifuratel, nifurfoline, nifurpirinol, nifurprazine, nifurtoinol, nitrofurantoin), quinolones and analogs (e.g., cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (e.g., acetyl sulfamethoxypyrazine, benzylsulfamide, chloramine-b, chloramine-t, dichloramine t, n2-formylsulfisomidine, n4-β-d-glucosylsulfanilamide, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, 4-sulfanilamidosalicylic acid, n4-sulfanilylsulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (e.g., acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (e.g., clofoctol, hexedine, methenamine, methenamine anhydromethylene-citrate, methenamine hippurate, methenamine mandelate, methenamine sulfosalicylate, nitroxoline, taurolidine, xibomol), antifungal antibiotics, polyenes (e.g., amphotericin b, candicidin, dermostatin, filipin, fungichromin, hachimycin, hamycin, lucensomycin, mepartricin, natamycin, nystatin, pecilocin, perimycin), others (e.g., azaserine, griseofulvin, oligomycins, neomycin undecylenate, pyrrolnitrin, siccanin, tubercidin, viridin), synthetic antifungals, allylamines (e.g., butenafine, naftifine, terbinafine), imidazoles (e.g., bifonazole, butoconazole, chlordantoin, chlormidazole, cloconazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (e.g., tolciclate, tolindate, tolnaftate), triazoles (e.g., fluconazole, itraconazole, saperconazole, terconazole) others (e.g., acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, zinc propionate), antineoplastics, antibiotics and analogs (e.g., aclacinomycins, actinomycin fl, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, zorubicin), antimetabolites (e.g. folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thioguanine), pyrimidine analogs (e.g., ancitabine, azacitidine, 6-azauridine, carmofur, cytarabine, doxifluridine, emitefur, enocitabine, floxuridine, fluorouracil, gemcitabine, tagafur), antiinflammatory agents, steroidal antiinflammatory agents, acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide, non-steroidal antiinflammatory agents, aminoarylcarboxylic acid derivatives (e.g., enfenamic acid, etofenamate, flufenamic acid, isonixin, meclofenamic acid, mefenamic acid, niflumic acid, talniflumate, terofenamate, tolfenamic acid), arylactic acid derivatives (e.g., aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (e.g., bumadizon, butibufen, fenbufen, xenbucin), arylcarboxylic acids (e.g., clidanac, ketorolac, tinoridine), arylpropionic acid derivatives (e.g., alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (e.g., difenamizole, epirizole), pyrazolones (e.g., apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (e.g., acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (e.g., ampiroxicam, droxicam, isoxicam, lomoxicam, piroxicam, tenoxicam), ε-acetamidocaproic acid, s-adenosylmethionine, 3-amino-4-hydroxybutyric acid, amixetrine, bendazac, benzydamine, a-bisabolol, bucolome, difenpiramide, ditazol, emorfazone, fepradinol, guaiazulene, nabumetone, nimesulide, oxaceprol, paranyline, perisoxal, proquazone, superoxide dismutase, tenidap, and zileuton.

The therapeutic agents may also be used in combination with other therapeutic agents and therapies, including but not limited to agents and therapies useful for the treatment, prevention, inhibition, delaying onset of, or causing regression of angiogenesis or neovascularization, particularly CNV. In some variations the additional agent or therapy is used to treat regression of angiogenesis or neovascularization, particularly CNV. Non-limiting examples of such additional agents and therapies include pyrrolidine, dithiocarbamate (NFκB inhibitor); squalamine; TPN 470 analogue and fumagillin; PKC (protein kinase C) inhibitors; Tie-1 and Tie-2 kinase inhibitors; inhibitors of VEGF receptor kinase; proteosome inhibitors such as Velcade™ (bortezomib, for injection; ranibuzumab (Lucentis™) and other antibodies directed to the same target; pegaptanib (Macugen™); vitronectin receptor antagonists, such as cyclic peptide antagonists of vitronectin receptor-type integrins; α-v/β-3 integrin antagonists; α-v/β-1 integrin antagonists; thiazolidinediones such as rosiglitazone or troglitazone; interferon, including γ-interferon or interferon targeted to CNV by use of dextran and metal coordination; pigment epithelium derived factor (PEDF); endostatin; angiostatin; tumistatin; canstatin; anecortave acetate; acetonide; triamcinolone; tetrathiomolybdate; RNA silencing or RNA interference (RNAi) of angiogenic factors, including ribozymes that target VEGF expression; Accutane™ (13-cis retinoic acid); ACE inhibitors, including but not limited to quinopril, captopril, and perindozril; inhibitors of mTOR (mammalian target of rapamycin); 3-aminothalidomide; pentoxifylline; 2-methoxyestradiol; colchicines; AMG-1470; cyclooxygenase inhibitors such as nepafenac, rofecoxib, diclofenac, rofecoxib, NS398, celecoxib, vioxx, and (E)-2-alkyl-2(4-methanesulfonylphenyl)-1-phenylethene; t-RNA synthase modulator; metalloprotease 13 inhibitor; acetylcholinesterase inhibitor; potassium channel blockers; endorepellin; purine analog of 6-thioguanine; cyclic peroxide ANO-2; (recombinant) arginine deiminase; epigallocatechin-3-gallate; cerivastatin; analogues of suramin; VEGF trap molecules; inhibitors of hepatocyte growth factor (antibodies to the growth factor or its receptors, small molecular inhibitors of the c-met tyrosine kinase, truncated versions of HGF e.g. NK4); apoptosis inhibiting agents; Visudyne™, snET2 and other photo sensitizers with photodynamic therapy (PDT); and laser photocoagulation.

Formulations

Unless the context clearly indicates otherwise, it is intended that any one or more of the therapeutic agents described herein may be used in the stable formulations described herein. Unless the context clearly indicates otherwise, it is intended that any one or more of the stable formulations described herein may be used to treat, prevent, inhibit, or delay onset of any one or more of the diseases or conditions described herein. Unless the context clearly indicates otherwise, it is intended that the stable formulations may, but need not be, formed by any one or more of the methods described herein.

The formulations described herein contain a therapeutic agent, and may generally be any liquid formulation, including but not limited to solutions, suspensions, and emulsions. In some variations the liquid formulations are in situ gelling formulations. In some variations after placement in an aqueous medium the liquid formulations form a non-dispersed mass relative to a surrounding medium. In some variations, the stable formulations described herein comprise the formulations described in the following copending patent applications, but prepared by the methods described herein: U.S. 60/651,790, filed Feb. 9, 2005, titled FORMULATIONS FOR OCULAR TREATMENT; U.S. 60/664,040, filed Feb. 9, 2005, titled LIQUID FORMULATIONS FOR TREATMENT OF DISEASES OR CONDITIONS; U.S. 60/664,119, filed Mar. 21, 2005, titled DRUG DELIVERY SYSTEMS FOR TREATMENT OF DISEASES OR CONDITIONS; U.S. 60/664,306, filed Mar. 21, 2005, titled IN SITU GELLING FORMULATIONS AND LIQUID FORMULATIONS FOR TREATMENT OF DISEASES OR CONDITIONS; U.S. Ser. No. 11/351,844, filed Feb. 9, 2006, titled FORMULATIONS FOR OCULAR TREATMENT; U.S. Ser. No. 11/351,761, filed Feb. 9, 2006, titled LIQUID FORMULATIONS FOR TREATMENT OF DISEASES OR CONDITIONS; U.S. Ser. No. 11/386,290, filed Mar. 21, 2006, titled DRUG DELIVERY SYSTEMS FOR TREATMENT OF DISEASES OR CONDITIONS; U.S. Ser. No. 11/352,092, filed Feb. 9, 2006, entitled RAPAMYCIN FORMULATIONS AND METHODS OF THEIR USE; U.S. 60/772,018, filed Feb. 9, 2006, titled STABLE FORMULATIONS, AND METHODS OF THEIR PREPARATION AND USE; US 2005/0187241, and US 2005/0064010.; each of which is incorporated herein by reference in its entirety.

In some variations the therapeutic agent in the liquid formulation is between about 0.01 to about 30% of the total weight of the formulation; between about 0.05 to about 15%; between about 0.1 to about 10%; between about 1 to about 5%; or between about 5 to about 15%; between about 8 to about 10%; between about 0.01 to about 1%; between about 0.05 to about 5%; between about 0.1 to about 0.2%; between about 0.2 to about 0.3%; between about 0.3 to about 0.4%; between about 0.4 to about 0.5%; between about 0.5 to about 0.6%; between about 0.6 to about 0.7%; between about 0.7 to about 1%; between about 1 to about 5%; between about 5 to about 10%; between about 15 to about 30%, between about 20 to about 30%; or between about 25 to about 30%.

By "about" a certain amount of a component of a formulation is meant 90-110% of the amount stated.

Those of skill in the art, given the teachings herein, can determine what amount or concentration of a given therapeutic agent is equivalent to an amount or concentration of rapamycin by, for example, administering the therapeutic agent at various amounts or concentrations to a disease model system, such as an in vivo or in vivo model system, and comparing the results in the model system relative to the results of various amounts or concentrations of rapamycin. Those of skill in the art, given the teachings herein, can also determine what amount or concentration of a given therapeutic agent is equivalent to an amount or concentration of rapamycin by reviewing the scientific literature for experiments performed comparing rapamycin to other therapeutic agents. It is understood that even the same therapeutic agent may have a different equivalent level of rapamycin when, for example, a different disease or disorder is being evaluated, or a different type of formulation is used. Nonlimiting examples of scientific references with comparative studies of rapamycin and other therapeutic agents on ocular disease are Ohia et al., *Effects of steroids and immunosuppressive drugs on endotoxin-uveitis in rabbits*, J. Ocul. Pharmacol. 8(4):295-307 (1992); Kulkarni, *Steroidal and nonsteroidal drugs in endotoxin-induced uveitis*, J. Ocul. Pharmacol. 10(1):329-34 (1994); Hafizi et al., *Differential effects of rapamycin, cyclosporine A, and FK506 on human coronary artery smooth muscle cell proliferation and signaling*, Vascul Pharmacol. 41(4-5):167-76 (2004); and US 2005/0187241.

For example, in a model for wet AMD, if a therapeutic agent is found to be approximately 10-fold less potent or efficacious than rapamycin in the treatment of wet AMD, a concentration of 10 ng/ml of the therapeutic agent would be equivalent to a 1 ng/ml concentration of rapamycin. Or if a therapeutic agent is found to be approximately 10-fold less potent or efficacious than rapamycin in the treatment of wet AMD, a 10-fold amount of the therapeutic agent would be administered relative to the amount of rapamycin.

In some variations the formulation comprises a therapeutic agent and a solvent component. The solvent component may be, for instance, between about 0.01 to about 99.9% of the total weight of the formulation; between about 0.1 to about 99%; between about 25 to about 55%; between about 30 to about 50%; or between about 35 to about 45%; between about 0.1 to about 10%; between about 10 to about 20%; between about 20 to about 30%; between about 30 to about 40%; between about 40 to about 45%; between about 40 to about 45%; between about 45 to about 50%; between about 50 to about 60%; between about 50 to about 70%; between about 70 to about 80%; between about 80 to about 90%; or between about 90 to about 100%. In some variations the solvent component comprises between about 0.1% to about 10% of the final weight of the formulation.

The formulations described herein may comprise a diluent component. The diluent component may be, for example, between about 1 to about 99% of the total weight of the formulation; between about 20 and about 99%; between about 50 and about 99%; between about 60 to about 99%; or between about 70 to about 99%; between about 80 to about 99%; between about 90 to about 99%; or between about 92 to about 96% of the final weight of the formulation. In some variations the diluent component comprises greater than about 50%, greater than about 60%, greater than about 70%, greater than about 80%, or greater than about 90%, of the formulation.

Some variations of liquid formulations includes a therapeutic agent or agents such as but not limited to rapamycin between about 0.01 and about 20% by weight of the total, a solvent between about 0.5% and about 15% by weight of the total, and a diluent component between about 70% and about 96% by weight of the total. In some variations the formulations further comprise stabilizing agents, excipients, adjuvants, or antioxidants, between about 0 and about 40% by weight of the total.

In some variations, a liquid formulation may comprise about 2% therapeutic agent, including but not limited to rapamycin, per weight of the total; about 4% solvent by weight of the total; and a diluent component, at about 94% by weight of the total.

In some variations, the liquid formulations described herein have a viscosity of between 40% and 120% centipoise. In some variations the liquid formulations described herein have a viscosity of between 60% and 80% centipoise.

Formulations and Liquid Formulations for Delivery of Therapeutic Agents

An "effective amount," which is also referred to herein as a "therapeutically effective amount," of a therapeutic agent for administration as described herein is that amount of the therapeutic agent that provides the therapeutic effect sought when administered to the subject. The achieving of different therapeutic effects may require different effective amounts of therapeutic agent. For example, the therapeutically effective amount of a therapeutic agent used for preventing a disease or condition may be different from the therapeutically effective amount used for treating, inhibiting, delaying the onset of, or causing the regression of the disease or condition. In addition, the therapeutically effective amount may depend on the age, weight, and other health conditions of the subject as is well know to those versed in the disease or condition being addressed. Thus, the therapeutically effective amount may not be the same in every subject to which the therapeutic agent is administered.

An effective amount of a therapeutic agent for treating, preventing, inhibiting, delaying the onset of, or causing the regression of a specific disease or condition is also referred to herein as the amount of therapeutic agent effective to treat, prevent, inhibit, delay the onset of, or cause the regression of the disease or condition.

To determine whether a level of therapeutic agent is a "therapeutically effective amount" to treat, prevent, inhibit, delay on set of, or cause the regression of the diseases and conditions described in the Diseases and Conditions section, liquid formulations may be administered in animal models for the diseases or conditions of interest, and the effects may be observed.

Delivery of a therapeutically effective amount of the therapeutic agent for an extended period may be achieved via a single administration of a liquid formulation or may be achieved by administration of two or more doses of a liquid formulations. As a non-limiting example of such multiple applications, maintenance of the therapeutic amount of rapamycin for 3 months for treatment, prevention, inhibition, delay of onset, or cause of regression of wet AMD may be achieved by administration of one dose of liquid formulation delivering a therapeutic amount for 3 months or by sequential application of a plurality of doses of a liquid formulation. The optimal dosage regime will depend on the therapeutic amount of the therapeutic agent needing to be delivered, the period over which it need be delivered, and the delivery kinetics of the liquid formulation. Those versed in such extended therapeutic agent delivery dosing will understand how to identify dosing regimes that may be used based on the teachings described herein.

When using certain therapeutic agents for the treatment, prevention, inhibition, delaying the onset of, or causing the regression of certain diseases, it may be desirable for delivery of the therapeutic agent not to commence immediately upon placement of the formulation into the eye region, but for delivery to commence after some delay. For example, but in no way limiting, such delayed release may be useful where the therapeutic agent inhibits or delays wound healing and delayed release is desirable to allow healing of any wounds occurring upon placement of the formulation. Depending on the therapeutic agent being delivered and/or the diseases and conditions being treated, prevented, inhibited, onset delayed, and regression caused this period of delay before delivery of the therapeutic agent commences may be about 1 hour, about 6 hours, about 12 hours, about 18 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 21 days, about 28 days, about 35 days, or about 42 days. Other delay periods may be possible. Delayed release formulations that may be used will be clear to people versed in the technology given the teachings herein.

Generally, the therapeutic agent may be formulated in any formulation or liquid formulation capable of delivery of a therapeutically effective amount of the therapeutic agent to a subject or to the eye of a subject for the required delivery period. Formulations include liquid formulations.

Solubilization of Therapeutic Agents

One formulation or liquid formulation that may be used is a formulation or liquid formulation in which the therapeutic agent is dissolved in a solvent component. Generally, any solvent which has the desired effect may be used in which the therapeutic agent dissolves. In some variations the solvent is aqueous. In some variations the solvent is non-aqueous. An "aqueous solvent" is a solvent that contains at least about 50% water.

Generally, any concentration of solubilized therapeutic agent that has the desired effect can be used. The solvent component may be a single solvent or may be a mixture of solvents. The solvent component may be a single solvent or may be a mixture of solvents. Solvents and types of solutions are well known to those versed in such drug delivery technologies. See for example, Remington: The Science and Practice of Pharmacy, Twentieth Edition, Lippincott Williams & Wilkins; 20th edition (Dec. 15, 2000); Ansel's Pharmaceutical Dosage Forms and Drug Delivery Systems, Eighth Edition, Lippincott Williams & Wilkins (August 2004); Handbook Of Pharmaceutical Excipients 2003, American Pharmaceutical Association, Washington, D.C., USA and Pharmaceutical Press, London, UK; and Strickley, solubilizing Excipients in Oral and Injectable Formulations, Pharmaceutical Research, Vol. 21, No. 2, February 2004.

As noted previously, some solvents may also serve as solubilizing agents.

Solvents that may be used include but are not limited to any one or more of DMSO, ethanol, methanol, isopropyl alcohol; castor oil, propylene glycol, glycerin, polysorbate 80, benzyl alcohol, dimethyl acetamide (DMA), dimethyl formamide (DMF), glycerol formal, ethoxy diglycol (Transcutol, Gattefosse), triethylene glycol dimethyl ether (Triglyme), triacetin, diacetin, corn oil, acetyl triethyl citrate (ATC), ethyl lactate, dimethyl isosorbide (DMI), γ-butyrolactone, N-Methyl-2-pyrrolidinone (NMP), polyethylene glycol of various molecular weights, including but not limited to PEG 300 and PEG 400, and polyglycolated capryl glyceride (Labrasol, Gattefosse).

In some variations, the solvent is polyethylene glycol. Polyethylene glycol is known by various names and is available in various preparations, including but not limited to macrogels, macrogel 400, macrogel 1500, macrogel 4000, macrogel 6000, macrogel 20000, macrogola, breox PEG; carbowax; carbowax sentry; Hodag PEG; Lipo; Lipoxol; Lutrol E; PEG; Pluriol E; polyoxyethylene glycol, and α-Hydro-ω-hydroxy-poly(oxy-1,2-ethanediyl).

Other solvents include an amount of a $C_6$-$C_{24}$ fatty acid sufficient to solubilize a therapeutic agent.

Phospholipid solutions may also be used, such as lecithin, phosphatidylcholine, or a mixture of various diglycerides of stearic, palmitic, and oleic acids, linked to the choline ester of phosphoric acid; hydrogenated soy phosphatidylcholine (HSPC), distearoylphosphatidylglycerol (DSPG), L-α-dimyristoylphosphatidylcholine (DMPC), L-α-dimyristoylphosphatidylglycerol (DMPG).

Further examples of components to dissolve therapeutic agents include, for example, components such as alcohols, propylene glycol, polyethylene glycol of various molecular weights, propylene glycol esters, propylene glycol esterified with fatty acids such as oleic, stearic, palmic, capric, linoleic, etc; medium chain mono-, di-, or triglycerides, long chain fatty acids, naturally occurring oils, and a mixture thereof. The oily components for the solvent system include commercially available oils as well as naturally occurring oils. The oils may further be vegetable oils or mineral oils. The oils can be characterized as non-surface active oils, which typically have no hydrophile lipophile balance value. Commercially available substances comprising medium chain triglycerides include, but are not limited to, Captex 100, Captex 300, Captex 355, Miglyol 810, Miglyol 812, Miglyol 818, Miglyol 829, and Dynacerin 660. Propylene glycol ester formulations that are commercially available encompass Captex 200 and Miglyol 840, and the like. The commercial product, Capmul MCM, comprises one of many possible medium chain mixtures comprising monoglycerides and diglycerides.

Other solvents include naturally occurring oils such as peppermint oil, and seed oils. Exemplary natural oils include oleic acid, castor oil, safflower seed oil, soybean oil, olive oil, sunflower seed oil, sesame oil, and peanut oil. Soy fatty acids may also be used. Examples of fully saturated non-aqueous solvents include, but are not limited to, esters of medium to long chain fatty acids (such as fatty acid triglycerides with a chain length of about $C_6$ to about $C_{24}$). Hydrogenated soybean oil and other vegetable oils may also be used. Mixtures of fatty acids may be split from the natural oil (for example coconut oil, palm kernel oil, babassu oil, or the like) and refined. In some embodiments, medium chain (about $C_8$ to about $C_{12}$) triglycerides, such as caprilyic/capric triglycerides derived from coconut oil or palm seed oil, may be used. Medium chain mono- and diglycerides may also be used. Other fully saturated non-aqueous solvents include, but are not limited to, saturated coconut oil (which typically includes a mixture of lauric, myristic, palmitic, capric and caproic acids), including those sold under the Miglyol™ trademark from Huls and bearing trade designations 810, 812, 829 and 840). Also noted are the NeoBee™ products sold by Drew Chemicals. Non-aqueous solvents include isopropyl myristate. Examples of synthetic oils include triglycerides and propylene glycol diesters of saturated or unsaturated fatty acids having 6 to 24 carbon atoms such as, for example hexanoic acid, octanoic (caprylic), nonanoic (pelargonic), decanoic (capric), undecanoic, lauric, tridecanoic, tetradecanoic (myristic), pentadecanoic, hexadecanoic (palmitic), heptadecanoic, octadecanoic (stearic), nonadecanoic, heptadecanoic, eicosanoic, heneicosanoic, docosanoic and lignoceric acids, and the like. Examples of unsaturated carboxylic acids include oleic, linoleic and linolenic acids, and the like. The non-aqueous solvent can comprise the mono-, di- and triglyceryl esters of fatty acids or mixed glycerides and/or propylene glycol mono- or diesters wherein at least one molecule of glycerol has been esterified with fatty acids of varying carbon atom length. A non-limiting example of a "non-oil" useful as a solvent is polyethylene glycol.

Exemplary vegetable oils include cottonseed oil, corn oil, sesame oil, soybean oil, olive oil, fractionated coconut oil, peanut oil, sunflower oil, safflower oil, almond oil, avocado oil, palm oil, palm kernel oil, babassu oil, beechnut oil, linseed oil, rape oil and the like. Mono-, di-, and triglycerides of vegetable oils, including but not limited to corn, may also be used.

Polyvinyl pyrrolidone (PVP), cross-linked or not, may also be used as a solvent. Further solvents include but are not limited to $C_6$-$C_{24}$ fatty acids, oleic acid, Imwitor 742, Capmul, F68, F68 (Lutrol), PLURONICS including but not limited to PLURONICS F108, F127, and F68, Poloxamers, Jeffamines), Tetronics, F127; cyclodextrins such as α-cyclodextrin, β-cyclodextrin, hydroxypropyl-β-cyclodextrin, sulfobutylether-β-cyclodextrin (Captisol); CMC, polysorbitan 20, Cavitron, polyethylene glycol of various molecular weights including but not limited to PEG 300 and PEG 400.

Beeswax and d-α-tocopherol (Vitamin E) may also be used as solvents.

Solvents for use in the liquid formulations can be determined by a variety of methods known in the art, including but not limited to (1) theoretically estimating their solubility parameter values and choosing the ones that match with the therapeutic agent, using standard equations in the field; and (2) experimentally determining the saturation solubility of therapeutic agent in the solvents, and choosing the ones that exhibit the desired solubility.

Solubilization of Rapamycin

Where the therapeutic agent is rapamycin, solvents include but are not limited to any solvent as above, including but not limited to any one or more of DMSO, glycerin, ethanol, methanol, isopropyl alcohol; castor oil, propylene glycol, triethylene glycol, triacetin, diacetin, corn oil, acetyl triethyl citrate (ATC), ethyl lactate, polyvinylpropylene, polysorbate 80, benzyl alcohol, Dimethyl acetamide (DMA), dimethyl formamide (DMF), glycerol formal, ethoxy diglycol (Transcutol, Gattefosse), tryethylene glycol dimethyl ether (Triglyme), dimethyl isosorbide (DMI), γ-butyrolactone, N-Methyl-2-pyrrolidinone (NMP), polyethylene glycol of various molecular weights, including but not limited to PEG 300 and PEG 400, and polyglycolated capryl glyceride (Labrasol, Gattefosse).

Further solvents include but are not limited to $C_6$-$C_{24}$ fatty acids, oleic acid, Imwitor 742, Capmul, F68, F68 (Lutrol), PLURONICS including but not limited to PLURONICS F108, F127, and F68, Poloxamers, Jeffamines), Tetronics, F127, beta-cyclodextrin, CMC, polysorbitan 20, Cavitron, softigen 767, captisol, and sesame oil.

Other methods that may be used to dissolve rapamycin are described in Solubilization of Rapamycin, P. Simamora et al. *Int'l J. Pharma* 213 (2001) 25-29, the contents of which is incorporated herein in its entirety.

As a nonlimiting example, rapamycin can be dissolved in 5% DMSO or methanol in a balanced salt solution. The rapamycin solution can be unsaturated, a saturated or a supersaturated solution of rapamycin. The rapamycin solution can be in contact with solid rapamycin. In one nonlimiting example, rapamycin can be dissolved in a concentration of up to about 400 mg/ml. Rapamycin can also, for example, be dissolved in propylene glycol esterified with fatty acids such as oleic, stearic, palmic, capric, linoleic, etc.

Many other solvents are possible. Those of ordinary skill in the art, given the teachings herein, will find it routine to identify solvents for rapamycin.

Solubilizing Agents

Generally, any solubilizing agent or combination of solubilizing agents may be used in the liquid formulations described herein.

In some variations, the solubilizing agent is a surfactant or combination of surfactants. Many surfactants are possible. Combinations of surfactants, including combinations of various types of surfactants, may also be used. For instance, surfactants which are nonionic, anionic (i.e. soaps, sulfonates), cationic (i.e. CTAB), zwitterionic, polymeric or amphoteric may be used.

Surfactants that can be used may be determined by mixing a therapeutic agent of interest with a putative solvent and a putative surfactant, and observing the characteristics of the formulation after exposure to a medium.

Examples of surfactants include but are not limited to fatty acid esters or amides or either analogues, or hydrophilic derivatives thereof; monoesters or diesters, or hydrophilic derivatives thereof; or mixtures thereof; monoglycerides or diglycerides, or hydrophilic derivatives thereof; or mixtures thereof; mixtures having enriched mono- or/and diglycerides, or hydrophilic derivatives thereof; surfactants with a partially derivatized with a hydrophilic moiety; monoesters or diesters or multiple-esters of other alcohols, polyols, saccharides or oligosaccharides or polysaccharides, oxyalkylene oligomers or polymers or block polymers or hydrophilic derivatives thereof, or the amide analogues thereof; fatty acid derivatives of amines, polyamines, polyimines, aminoalcohols, aminosugars, hydroxyalkylamines, hydroxypolyimines, peptides, polypeptides, or the ether analogues thereof.

Hydrophilic Lipophilic Balance ("HLB") is an expression of the relative simultaneous attraction of a surfactant for water and oil (or for the two phases of the emulsion system being considered).

Surfactants are characterized according to the balance between the hydrophilic and lipophilic portions of their molecules. The hydrophilic-lipophilic balance (HLB) number indicates the polarity of the molecule in an arbitrary range of 1-40, with the most commonly used emulsifiers having a value between 1-20. The HLB increases with increasing hydrophilicity.

Surfactants that may be used include but are not limited to those with an HLB greater than 10, 11, 12, 13 or 14. Examples of surfactants include polyoxyethylene products of hydrogenated vegetable oils, polyethoxylated castor oils or polyethoxylated hydrogenated castor oil, polyoxyethylene-sorbitan-fatty acid esters, polyoxyethylene castor oil derivatives and the like, for example, Nikkol HCO-50, Nikkol HCO-35, Nikkol HCO-40, Nikkol HCO-60 (from Nikko Chemicals Co. Ltd.); Cremophor (from BASF) such as Cremophor RH40, Cremophor RH60, Cremophor EL, TWEENs (from ICI Chemicals) e.g., TWEEN 20, TWEEN 21, TWEEN 40, TWEEN 60, TWEEN 80, TWEEN 81, Cremophor RH410, Cremophor RH455 and the like.

The surfactant component may be selected from compounds having at least one ether formed from at least about 1 to 100 ethylene oxide units and at least one fatty alcohol chain having from at least about 12 to 22 carbon atoms; compounds having at least one ester formed from at least about 1 to 100 ethylene oxide units and at least one fatty acid chain having from at least about 12 to 22 carbon atoms; compounds having at least one ether, ester or amide formed from at least about 1 to 100 ethylene oxide units and at least one vitamin or vitamin derivative; and combinations thereof consisting of no more than two surfactants.

Other examples of surfactants include Lumulse GRH-40, TGPS, Polysorbate-80 (TWEEN-80), Polysorbate-20

(TWEEN-20), polyoxyethylene (20) sorbitan mono-oleate), glyceryl glycol esters, polyethylene glycol esters, polyglycolyzed glycerides, and the like, or mixtures thereof; polyethylene sorbitan fatty acid esters, polyoxyethylene glycerolesters, such as Tagat TO, Tagat L, Tagat I, tagat I2 and Tagat 0 (commercially available from Goldschmidt Chemical Co., Essen, Germany); ethylene glycol esters, such as glycol stearate and distearate; propylene glycol esters, such as propylene glycol myristate; glyceryl esters of fatty acids, such as glyceryl stearates and monostearates; sorbitan esters, such as spans and TWEENs; polyglyceryl esters, such as polyglyceryl 4-oleate; fatty alcohol ethoxylates, such as Brij type emulsifiers; ethoxylated propoxylated block copolymers, such as poloxamers; polyethylene glycol esters of fatty acids, such as PEG 300 linoleic glycerides or Labrafil 2125 CS, PEG 300 oleic glycerides or Labrafil M 1944 CS, PEG 400 caprylic/capric glycerides or Labrasol, and PEG 300 caprylic/capric glycerides or Softigen 767; cremophors, such as Cremophor E, polyoxyl 35 castor oil or Cremophor EL, Cremophor EL-P, Cremophor RH 4OP, polyoxyl 40 hydrogenated castor oil, Cremophor RH40; polyoxyl 60 hydrogenated castor oil or Cremophor RH 60, glycerol monocaprylate/caprate, such as Campmul CM 10; polyoxyethylated fatty acids (PEG-stearates, PED-laurates, Brij®), polyoxylated glycerides of fatty acid, polyoxylated glycerol fatty acid esters i.e. Solutol HS-15; PEG-ethers (Mirj®), sorbitan derivatives (TWEENs), sorbitan monooleate or Span 20, aromatic compounds (Tritons®), PEG-glycerides (PECEOL™), PEG-PPG (polypropylene glycol) copolymers (PLURONICS including but not limited to PLURONICS F108, F127, and F68, Poloxamers, Jeffamines), Tetronics, Polyglycerines, PEG-tocopherols, PEG-LICOL 6-oleate; propylene glycol derivatives, sugar and polysaccharide alkyl and acyl derivatives (octylsucrose, sucrose stearate, laurolydextran etc.) and/or a mixture thereof; surfactants based on an oleate or laureate ester of a polyalcohol copolymerized with ethylene oxide; Labrasol Gelucire 44/14; polyoxytheylene stearates; saturated polyglycolyzed glycerides; or poloxamers; all of which are commercially available. Polyoxyethylene sorbitan fatty acid esters can include polysorbates, for example, polysorbate 20, polysorbate 40, polysorbate 60, and polysorbate 80. Polyoxyethylene stearates can include polyoxyl 6 stearate, polyoxyl 8 stearate, polyoxyl 12 stearate and polyoxyl 20 stearate. Saturated polyglycolyzed glycerides are, for example, GELUCIRE 44/14 or GELUCIRE™ 50/13 (Gattefosse, Westwood, N.J., U.S.A.). Poloxamers used herein include poloxamer 124 and poloxamer 188.

Surfactants include d-α-tocopheryl polyethylene glycol 1000 succinate (TPGS), polyoxyl 8 stearate (PEG 400 monostearate), polyoxyl 40 stearate (PEG 1750 monostearate) and peppermint oil.

In some variations, surfactants having an HLB lower than 10 are used. Such surfactants may optionally be used in combination with other surfactants as co-surfactants. Examples of some surfactants, mixtures, and other equivalent formulations having an HLB less than or equal to 10 are propylene glycols, glyceryl fatty acids, glyceryl fatty acid esters, polyethylene glycol esters, glyceryl glycol esters, polyglycolyzed glycerides and polyoxyethyl steryl ethers. Propylene glycol esters or partial esters form the formulation of commercial products, such as Lauroglycol FCC, which contains propylene glycol laureate. The commercially available excipient Maisine 35-1 comprises long chain fatty acids, for example glyceryl linoleate. Products, such as Acconon E, which comprise polyoxyethylene stearyl ethers, may also be used. Labrafil M 1944 CS is one example of a surfactant wherein the formulation contains a mixture of glyceryl glycol esters and polyethylene glycol esters.

Solubilizing Agents for Rapamycin

Many solubilizing agents may be used for rapamycin, including but not limited to those described herein.

In some variations the solubilizing agent is a surfactant. Nonlimiting examples of surfactants that may be used for rapamycin include but are not limited to surfactants with an HLB greater than 10, 11, 12, 13 or 14. One nonlimiting example is Cremophor EL. In some variations, the surfactant may be a polymeric surfactant including but not limited to PLURONICS F108, F127, and F68, and Tetronics. As noted above, some solvents may also serve as surfactants. Those of ordinary skill in the art, given the teachings herein, will find it routine to identify which solubilizing agents and surfactants may be used for rapamycin.

Viscosity Modifying Agents

The liquid formulations described herein may be administered with or further comprise a viscosity modifying agent.

One exemplary viscosity modifying agent that may be used ishyaluronic acid. Hyaluronic acid is a glycosaminoglycan. It is made of a repetitive sequence of glucuronic acid and glucosamine. Hyaluronic acid is present in many tissues and organs of the body, and contributes to the viscosity and consistency of such tissues and organs. Hyaluronic acid is present in the eye, including the vitreous of the eye, and along with collagen contributes to the viscosity thereof. The liquid formulations described herein may further comprise or be administered with hyaluronic acid.

Other nonlimiting examples of viscosity modifying agents include polyalkylene oxides, glycerol, carboxymethyl cellulose, sodium alginate, chitosan, dextran, dextran sulfate and collagen. These viscosity modifying agents can be chemically modified.

Other viscosity modifying agents that may be used include but are not limited to carrageenan, cellulose gel, colloidal silicon dioxide, gelatin, propylene carbonate, carbonic acid, alginic acid, agar, carboxyvinyl polymers or carbomers and polyacrylamides, acacia, ester gum, guar gum, gum arabic, ghatti, gum karaya, tragacanth, terra, pectin, tamarind seed, larch arabinogalactan, alginates, locust bean, xanthan gum, starch, veegum, tragacanth, polyvinyl alcohol, gellan gum, hydrocolloid blends, and povidone. Other viscosity modifying agents known in the art can also be used, including but not limited to sodium carboxymethyl cellulose, algin, carageenans, galactomannans, hydropropyl methyl cellulose, hydroxypropyl cellulose, polyethylene glycol, polyvinylpyrrolidone, sodium carboxymethyl chitin, sodium carboxymethyl dextran, sodium carboxymethyl starch, xanthan gum, and zein.

Pharmaceutical Formulations

Unless the context clearly indicates otherwise, any of the formulations described herein may be used in any of the pharmaceutical formulations described herein.

The formulations described herein may further comprise various other components such as stabilizers, for example.

Stabilizers are not required in the formulations described herein. However, in some variations it may be desirable to add a stabilizer. Non-limiting examples of stabilizers that may be used in the formulations described herein include but are not limited to agents that will (1) improve the compatibility of excipients with the encapsulating materials such as gelatin, (2) improve the stability (e.g. prevent crystal growth of a therapeutic agent such as rapamycin) of a therapeutic agent such as rapamycin and/or rapamycin derivatives, and/or (3) improve formulation stability. Note that there is overlap between components that are stabilizers and those that are solvents, solubilizing agents or surfactants, and the same component can carry out more than one role.

Stabilizers may be selected from fatty acids, fatty alcohols, alcohols, long chain fatty acid esters, long chain ethers, hydrophilic derivatives of fatty acids, polyvinylpyrrolidones, polyvinylethers, polyvinyl alcohols, hydrocarbons, hydrophobic polymers, moisture-absorbing polymers, and combinations thereof. Amide analogues of the above stabilizers can also be used. The chosen stabilizer may change the hydrophobicity of the formulation (e.g. oleic acid, waxes), or improve the mixing of various components in the formulation (e.g. ethanol), control the moisture level in the formula (e.g. PVP), control the mobility of the phase (substances with melting points higher than room temperature such as long chain fatty acids, alcohols, esters, ethers, amides etc. or mixtures thereof; waxes), and/or improve the compatibility of the formula with encapsulating materials (e.g. oleic acid or wax). Some of these stabilizers may be used as solvents/co-solvents (e.g. ethanol). Stabilizers may be present in sufficient amount to inhibit the therapeutic agent's (such as rapamycin's) crystallization.

Examples of stabilizers include, but are not limited to, saturated, monoenoic, polyenoic, branched, ring-containing, acetylenic, dicarboxylic and functional-group-containing fatty acids such as oleic acid, caprylic acid, capric acid, caproic acid, lauric acid, myristic acid, palmitic acid, stearic acid, behenic acid, linoleic acid, linolenic acid, eicosapentaenoic acid (EPA), DHA; fatty alcohols such as stearyl alcohol, cetyl alcohol, ceteryl alcohol; other alcohols such as ethanol, isopropyl alcohol, butanol; long chain fatty acid esters, ethers or amides such as glyceryl stearate, cetyl stearate, oleyl ethers, stearyl ethers, cetyl ethers, oleyl amides, stearyl amides; hydrophilic derivatives of fatty acids such as polyglyceryl fatty acids, polyethylene glycol fatty acid esters; polyvinylpyrrolidones, polyvinylalcohols (PVAs), waxes, docosahexaenoic acid and de-hydroabietic acid etc.

The formulations described may further contain a gelling agent that alters the texture of the final formulation through formation of a gel.

The therapeutic agents for use as described herein, such as rapamycin, may be subjected to conventional pharmaceutical operations, such as sterilization and formulations containing the therapeutic agent may also contain conventional adjuvants, such as preservatives, stabilizers, wetting agents, emulsifiers, buffers etc. The therapeutic agents may also be formulated with pharmaceutically acceptable excipients for clinical use to produce a pharmaceutical formulation. Formulations for ocular administration may be presented as a solution, suspension, particles of solid material, a discrete mass of solid material, incorporated within a polymer matrix, liquid formulations or in any other form for ocular administration. The therapeutic agents may be used to prepare a medicament to treat, prevent, inhibit, delay onset, or cause regression of any of the conditions described herein. In some variations, the therapeutic agents may be used to prepare a medicament to treat any of the conditions described herein.

A formulation containing a therapeutic agent such as rapamycin may contain one or more adjuvants appropriate for the indicated route of administration. Adjuvants with which the therapeutic agent may be admixed with include but are not limited to lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol. When a solubilized formulation is required the therapeutic agent may be in a solvent including but not limited to polyethylene glycol of various molecular weights, propylene glycol, carboxymethyl cellulose colloidal solutions, methanol, ethanol, DMSO, corn oil, peanut oil, cottonseed oil, sesame oil, tragacanth gum, and/or various buffers. Other adjuvants and modes of administration are well known in the pharmaceutical art and may be used in the practice of the methods, formulations and liquid formulations described herein. The carrier or diluent may include time delay material, such as glyceryl monostearate or glyceryl distearate alone or with a wax, or other materials well known in the art. The formulations for use as described herein may also include gel formulations, erodible and non-erodible polymers, microspheres, and liposomes.

Other adjuvants and excipients that may be used include but are not limited to $C_8$-$C_{10}$ fatty acid esters such as softigen 767, polysorbate 80, PLURONICS, Tetronics, Miglyol, and Transcutol.

Additives and diluents normally utilized in the pharmaceutical arts can optionally be added to the pharmaceutical formulation and the liquid formulation. These include thickening, granulating, dispersing, flavoring, sweetening, coloring, and stabilizing agents, including pH stabilizers, other excipients, anti-oxidants (e.g., tocopherol, BHA, BHT, TBHQ, tocopherol acetate, ascorbyl palmitate, ascorbic acid propyl gallate, and the like), preservatives (e.g., parabens), and the like. Exemplary preservatives include, but are not limited to, benzylalcohol, ethylalcohol, benzalkonium chloride, phenol, chlorobutanol, and the like. Some useful antioxidants provide oxygen or peroxide inhibiting agents for the formulation and include, but are not limited to, butylated hydroxytoluene, butylhydroxyanisole, propyl gallate, ascorbic acid palmitate, α-tocopherol, and the like. Thickening agents, such as lecithin, hydroxypropylcellulose, aluminum stearate, and the like, may improve the texture of the formulation.

In addition, a viscous polymer may be added to the suspension, assisting the localization and ease of placement and handling. In some uses of the liquid formulation, a pocket in the sclera may be surgically formed to receive an injection of the liquid formulations. The hydrogel structure of the sclera can act as a rate-controlling membrane. Particles of therapeutic agent substance for forming a suspension can be produced by known methods including but not limited to via ball milling, for example by using ceramic beads. For example, a Cole Parmer ball mill such as Labmill 8000 may be used with 0.8 mm YTZ ceramic beads available from Tosoh or Norstone Inc.

In a further aspect are provided use of the formulations or pharmaceutical formulations of therapeutic agents, including but not limited to rapamycin, as described herein in the manufacture of a medicament. Particularly, the manufacture of a medicament for use in the treatment of conditions as described herein. Further, the pharmaceutical formulations thereof, variously described herein, are also intended for use in the manufacture of a medicament for use in treatment of the conditions and, in accordance with the methods, described herein, unless otherwise noted.

Methods for Preparing and Packaging Liquid Formulations of Therapeutic Agents

One nonlimiting method that may be used for preparing the liquid formulations described herein, including but not limited to liquid formulations comprising rapamycin, is by mixing a solvent and a therapeutic agent together at room temperature or at slightly elevated temperature until a solution or suspension is obtained, with optional use of a sonicator, and then cooling the formulation. Other components including but not limited to those described above may then be mixed with the formulation. Other preparation methods may be used, and will be identifiable to those of skill in the art given the teachings herein.

Examples and variations of methods for preparing and packaging liquid formulations of therapeutic agents are described herein with reference to the flowcharts shown in FIGS. 1A-1F. In some variations, these methods are used to prepare liquid formulations including but not limited to those described in the Detailed Description section including those liquid formulations described in the tables and examples. Some variations of the exemplary processes shown in the flowcharts of FIGS. 1A-1F do not include all of the steps shown. In some variations, some of the steps shown in these flowcharts are executed in an order other than that depicted. Also, some variations of the methods include process steps not shown in the flowcharts.

Figure 1A:
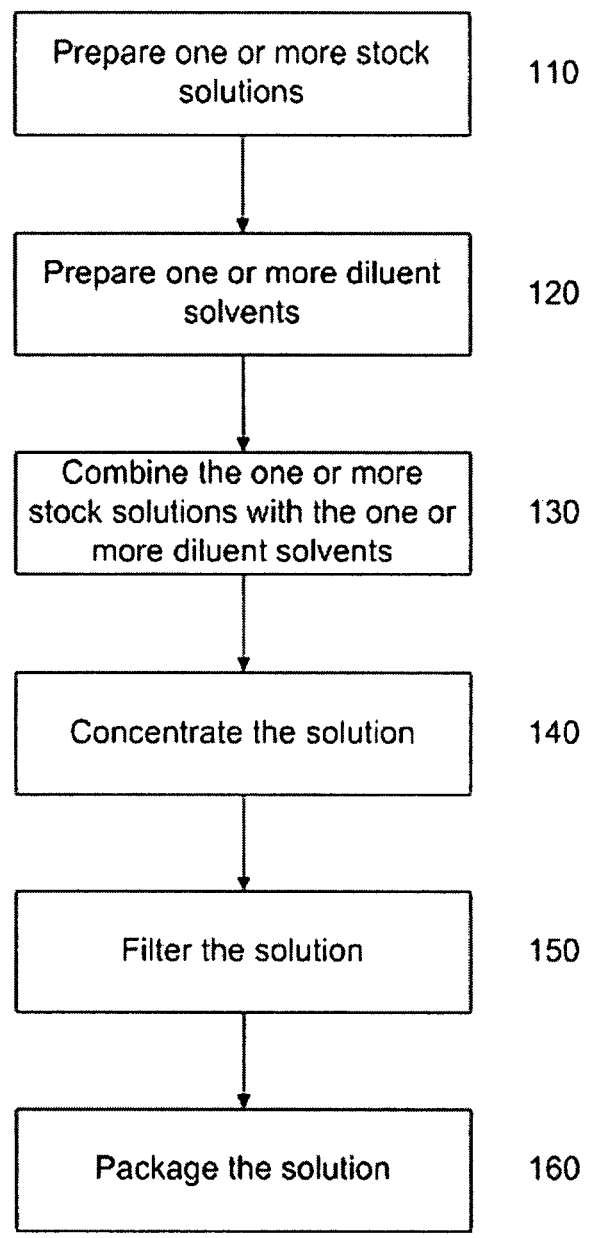
FIGS. 1A-1F depict variations of one process for preparing the formulations described herein.
Figure 1B:
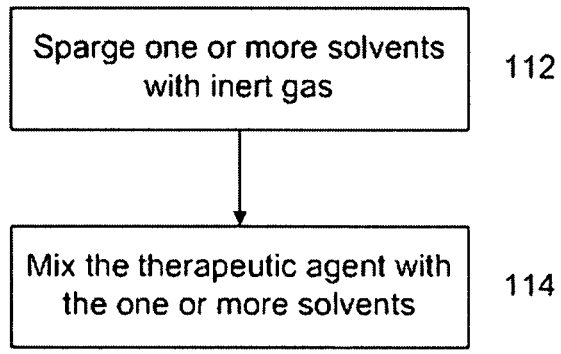

Referring to FIG. 1A, in step 110 of one exemplary process for preparing and packaging a liquid formulation of one or more therapeutic agents one or more stock solutions are prepared. In some variations, stock solutions of one or more therapeutic agents are prepared. Where the liquid formulation includes more than one therapeutic agent, in some variations a stock solution comprising several therapeutic agents is prepared. In other variations a separate stock solution is prepared for each therapeutic agent. In some variations stock solutions of other components included in the liquid formulation such as stabilizers, for example, are prepared or one or more such components are included in a therapeutic agent stock solution. In some variations stock solutions of one or more components of the liquid formulation are obtained commercially rather than prepared as part of the process shown in FIG. 1A.

In some variations one or more stock solutions are prepared in step 110 for immediate use in preparation of a liquid formulation of one or more therapeutic agents. In other variations one or more stock solutions are prepared and then stored for a period of time that does not decrease the stability of the one or more therapeutic agents by more than about 10%. In some variations, the one or more stock solutions are stored for up to about 1 hour, up to about 2 hours, up to about 3 hours, up to about 4 hours, up to about 6 hours, up to about 8 hours, up to about 10 hours, up to about 16 hours, up to about 24 hours, up to about 2 days, up to about 3 days, up to about 5 days, up to about 7 days, up to about 1 month, up to about 2 months, up to about 3 months, up to about 4 months, up to about 5 months, up to about 6 months, up to about 7 months, up to about 8 months, up to about 9 months, up to about 10 months, up to about 11 months, up to about 12 months, or longer. In some variations, the one or more stock solutions are stored for a period of between about 1 minute and about 2 hours. In some variations, the one or more stock solutions are stored for a period of between about 1 minute and about 1 hour. In some variations, the one or more stock solutions are stored for a period of between about 30 and about 60 minutes. Generally, the stock solution may be stored for any period of time under any conditions that retain stability of the one or more therapeutic agents by at least about 50%, at least about 60%, at least about 70%, at least about 80%, at least about 90%, at least about 92%, at least about 94%, at least about 96%, at least about 98%, or at least about 99%.

Solvents used to prepare stock solutions include but are not limited to solvents, solubilizing agents, and other components of liquid formulations such as those described in the Detailed Description including the tables and examples, and mixtures thereof. Therapeutic agents for which stock solutions are prepared include but are not limited to those listed in the Therapeutic Agents section and in the tables and examples, and mixtures thereof. Therapeutic agents may be provided in solid, powder, solution, suspension, or emulsion form, for example.

In some variations, the solvent is treated in such a way as to reduce the level of oxygen in the solvent. In some variations, shown in FIG. 1B, the solvent is sparged with an inert gas, such as a noble gas. In some variations, the solvent is sparged with nitrogen.

In some variations, the therapeutic agent is mixed with the solvent and sonicated for a period of time sufficient to dissolve the therapeutic agent in the solvent. In some variations, the mixture is sonicated for a period of time under conditions that retain stability of the one or more therapeutic agents by at least about 50%, at least about 60%, at least about 70%, at least about 80%, at least about 90%, at least about 92%, at least about 94%, at least about 96%, at least about 98%, or at least about 99%.

In some variations, stability of a component of the formulations described herein is measured by HPLC or mass spectrometry.

In step 120 one or more diluent solvents are prepared. In some variations the diluent solvents are subsequently used (step 130) to dilute the one or more stock solutions, such as those prepared in step 110. Diluent solvents also include but are not limited to solvents, solubilizing agents, and other components of liquid formulations such as those described in the Detailed Description including the tables and examples, and mixtures thereof.

Figure 1C:
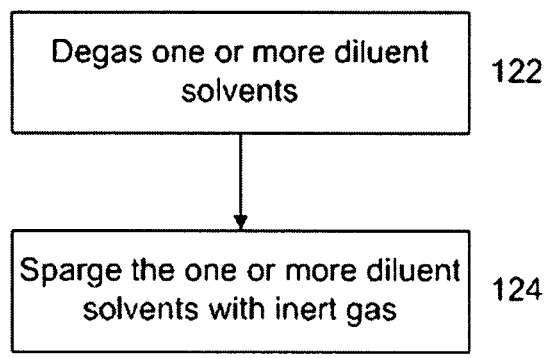

In some variations, including but not limited to those shown in FIG. 1C, the diluent solvent is degased. In some variations this treatment is to decrease the level of air bubbles, and hence the oxygen in the diluent solvent. In some variations the diluent solvent is degassed by centrifugation, included but not limited to by use of a double inverted centrifuge. In some variations the diluent solvent is sonicated for a period of time sufficient to decrease the level of oxygen in the diluent solvent. In some variations the diluent solvent is sonicated for a period of time and under conditions that retain the stability of the diluent solvent by at least about 50%, at least about 60%, at least about 70%, at least about 80%, at least about 90%, at least about 92%, at least about 94%, at least about 96%, at least about 98%, or at least about 99%. In some variations, including but not limited to those shown in FIG. 1C, the diluent solvent is sparged with an inert gas for a period of time sufficient to decrease the level of oxygen in the diluent solvent. In some variations, the diluent solvent is both sonicated and sparged with an inert gas. In some variations the inert gas is a noble gas, including but not limited to nitrogen, argon, or helium. In some variations, the inert gas is nitrogen.

In some variations the therapeutic agent or the diluent solvent is treated with a chemical agent to reduce the level of oxygen or oxygen radicals in the diluent solvent, including but not limited to an antioxidant or oxygen scavenger. In some variations the oxygen scavenger is sodium sulfate. In some variations the diluent solvent is treated with a physical force to reduce the level of oxygen in the diluent solvent, including but not limited to a physical pressure, including but not limited to centrifugation. In some variations the diluent solvent is heated to reduce the level of oxygen therein. In some variations the diluent solvent is heated to reduce the level of oxygen therein, and cooled under a nitrogen blanket.

In some variations one or more diluent solvents are prepared in step 120 for immediate use in preparation of a liquid formulation of one or more therapeutic agents. In other variations one or more diluent solvents are prepared and then stored for a period of time prior to use. In some variations the diluent solvent is stored for a period of time such that it remains sufficiently degassed. By "sufficiently degassed" is meant that the diluent solvent is treated for a period of time that, when the active agent is exposed to the diluent solvent, the therapeutic agent retains stability of at least about 90% relative to the stability of the therapeutic agent prior to exposure to the diluent solvent. In some variations, the diluent solvent is degassed to the extent that the therapeutic agent retains stability of at least about 70%, at least about 75%, at least about 80%, at least about 85%, at least about 90%, at least about 92%, at least about 94%, at least about 96%, at least about 98%, or at least about 99% after the period of storage.

In some variations, the period of time the diluent solvent is stored depends upon the sensitivity of the therapeutic agent to the gas that was removed by one or more of the treatments described herein. In some variations, the period of time the diluent solvent is stored depends upon the sensitivity of the therapeutic agent to oxygen that was removed by one or more of the treatments described herein.

In some variations, the diluent solvent is used within an hour of preparation. In some variations, the diluent solvent is stored for a period of about 1 minute to about 24 hours; about 1 minute to about 12 hours; about 1 minute to about 6 hours; about 1 minute to about 4 hours; about 1 minute to about 2 hours; or about 1 minute to about 1 hours.

Figure 1D:
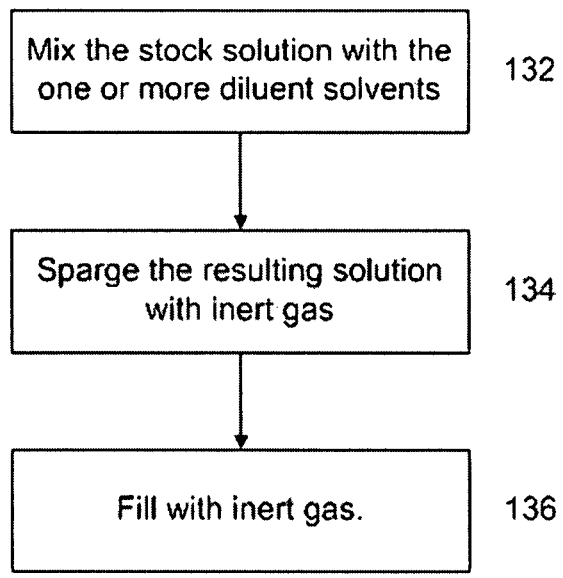
Figure 1E:
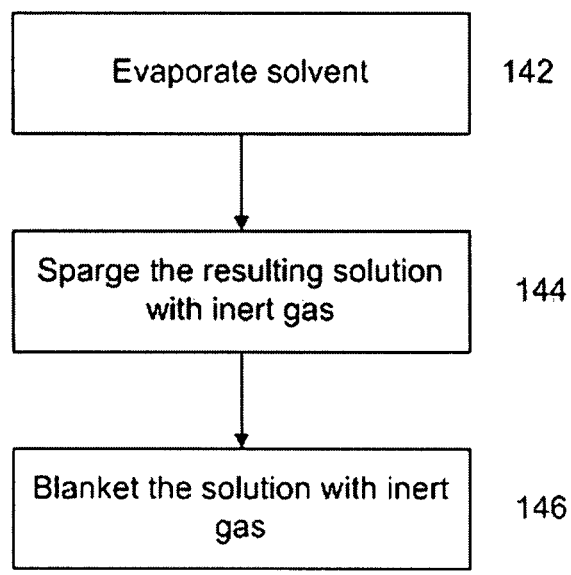

In step 130 one or more stock solutions such as those prepared in step 110 are combined with one or more diluent solvents such as those prepared in step 120. In some variations this process is as shown in FIG. 1D. In some variations, the stock solution is mixed with the diluent solvent by rotation on a rotary evaporator for a period of time that is sufficient to mix the stock solution with the stock solution with the diluent solvent, while retaining the stability of the therapeutic agent for by least about 70%, at least about 75%, at least about 80%, at least about 85%, at least about 90%, at least about 92%, at least about 94%, at least about 96%, at least about 98%, or at least about 99% relative to the therapeutic agent prior to mixing. In some variations the one or more stock solutions are mixed with the diluent solvent using any method to make a homogeneous mixture, such as mixing or vortexing. In some variations stock solutions of or including other components of the liquid formulation are similarly prepared.

Referring to FIG. 1D, in some variations combining the stock solution or solutions with the diluent solvent or solvents (FIG. 1A step 130) comprises mixing the stock solution or solutions with the diluent solvent or solvents in step 132, sparging the resulting solution with inert gas in step 134, and filling with inert gas in step 136. In some variations the stock solution or solutions are combined with the diluent solvent or solvents and mixed by rotating the solution in a rotary evaporator for a period of time and at a temperature to get the desired final concentration of the stock solution solvent. In some variations this period of time is between about 10 minutes and about 6 hours. In some variations the period of time is between about 30 minutes and about 4 hours. In some variations the period of time is between about 1 and about 4 hours. In some variations the temperature of the solution is kept below a level that results in substantial degradation of the therapeutic agent.

In some variations, the mixture resulting from step 130 is treated to reduce the level of oxygen or other gas. In some variations the mixture is treated by treatment with an inert gas, a chemical agent, or a physical pressure as described herein. In some variations, the mixture is then treated so as to reduce the exposure of the mixture to the surrounding environment, including but not limited to the air. In some variations the mixture is blanketed with an inert gas, such as a noble gas, including but not limited to nitrogen, argon, or helium.

In some variations the mixture resulting from step 130 is a solution.

In step 140 a solution resulting from step 130 is concentrated. In some variations, including but not limited to those shown in FIG. 1E, the solution is concentrated by evaporating or otherwise driving off some or all of a lower boiling point solvent. In some variations, a solvent removed in whole or in part in step 140 was a component of a stock solution in which a therapeutic agent or other component of the liquid formulation was dissolved prior to dilution in step 110.

In step 150 the solution resulting from step 140 is filtered. The mixture may be filtered with any filter capable of removing microbes. In some variations the filter is a 0.2 micron filter. In some variations the membranes or filters are made of PTFE (poly-(tetrafluoro)ethylene) or PVDF (poly(vinylidene)difluoride), including but not limited to those filters or membranes made by the Pall Corporation.

Figure 1F:
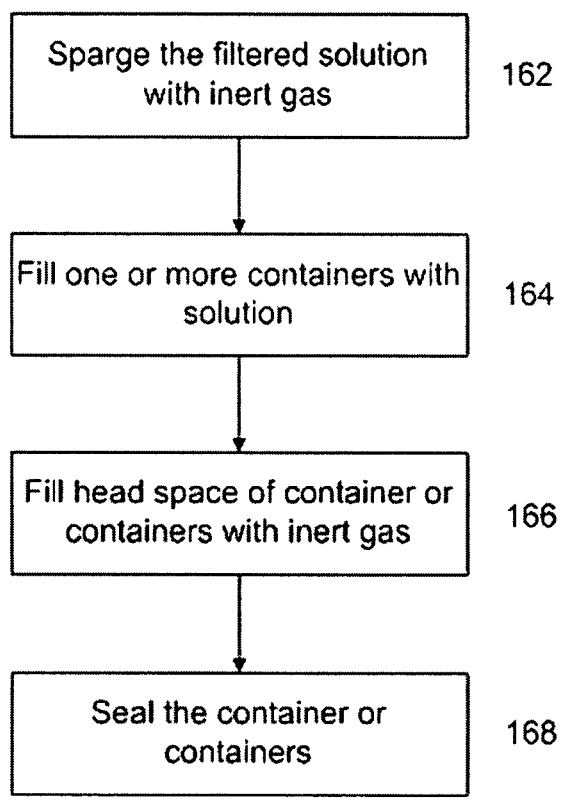

In some variations, including but not limited to those shown in FIG. 1F, a filtered solution is treated to reduce the level of oxygen or other gas in the solution. In some variations the mixture is treated with an inert gas, such as sparging with a noble gas, or treatment with a chemical agent or a physical pressure as described herein. In some variations, the mixture is then treated so as to reduce the exposure of the mixture to the surrounding environment, including but not limited to the air. In some variations the mixture is blanketed with an inert gas, such as a noble gas, including but not limited to nitrogen, argon, or helium.

In step 160 the filtered solution resulting from step 150 is packaged in one or more containers. In some variations, including but not limited to those shown in FIG. 1F, the filtered solution is packaged in one or more containers in such a way as to minimize exposure of the solution to one or more components of air. In some variations, containers with low head space are used for solutions wherein exposure to one or more components of air, including but not limited to oxygen, changes the level or quality of the activity of the solution as compared to the level or quality of the activity prior to exposure of the one or more components to air.

In some variations, the container is of a size or shape that minimizes head space relative to the volume of the liquid formulation contained therein. In some variations, the head space is minimized by maximizing the fill volume of the container. In some variations the head space is less than about 0.1%, less than about 0.5%, less than about 1%, less than about 2%, less than about 3%, less than about 4%, less than about 5%, or less than about 10% of the volume of the solution. In some variations the head space is between about 0.1% to about 0.5%, between about 0.5% to about 1%, between about 1% to 2%, between about 2% to about 3%, between about 3% to about 4%, between about 4% to about 5%, or between about 5% to about 10% of the volume of the solution.

In some variations the head space is filled with air. In some variations the head space is filled with an inert material, including but not limited to one or more inert gases. In some variations the inert gas is a noble gas, including but not limited to nitrogen, argon or helium.

In some variations, the container is configured to minimize contact area between the solution and the surface of the container. In some variations the portion of the container to which the solution is exposed is treated or manufactured to minimize interaction of the portion of the container to which the solution is exposed with the solution.

In some variations, the container comprises a plastic or glass, or combination thereof, including but not limited to any one or more of a plastic or glass used by those of skill in the art given the teachings herein. In some variations the portion of the container to which the solution is exposed is made of a clear or amber glass. In some variations, the portion of the container to which the solution is exposed is made of a clear glass, including but not limited to those manufactured by West.

In some variations the portion of the container that is exposed to the formulation in liquid form is made of any material that substantially holds its shape and does not react or interact with the formulation in liquid form in such a way as to substantially diminish or change the activity of the formulation in liquid form. In some variations the activity of the formulation in liquid form is diminished or changed by between about 0.1 to about 1%, between about 1 to about 2%, between about 2 to about 3%, between about 3 to about 5%, between about 5 to about 10%, between about 10 to about 15%, between about 15 to about 20%, between about 20 to about 25%, between about 25 to about 50%, or greater than about 50% when compared to the formulation in liquid form prior to being placed in the low volume container. In some variations the activity of the formulation in liquid form is diminished or changed by less than about 20%, less than about 15%, less than about 13%, less than about 10%, less than about 8, less than about 6, less than about 4, or less than about 2% when compared to the formulation prior to being placed in the container.

In some variations the portion of the container that is exposed to the formulation comprises glass. In some variations the portion of the container that is exposed to the formulation does not comprise silicon. In some variations the portion of the container that is exposed to the formulation does comprise silicon. In some variations the portion of the container that is exposed to the formulation is silanized. In some variations the portion of the container that is exposed to the formulation comprises a plastic material that does not react or interact with the formulation in such a way as to substantially diminish or change the activity of the formulation.

The containers may generally be made of any material. In some variations the container comprises a moldable polymer. In some variations the container comprises a thermoplastic polymer. In some variations the thermoplastic polymer is blended with one or more other polymers, including but not limited to elastomer(s) and plasticized polyolefins.

Thermoplastic polymers include, but are not limited to, polyolefins, polyamides, polyesters, polycarbonates, polysulfones, polyacetals, polylactones, acrylonitrile-butadiene-styrene resins, polyphenylene oxide, polyphenylene sulfide, styrene-acrylonitrile resins, styrene maleic anhydride, polyimides, aromatic polyketones, or mixtures of two or more of the above. Polyolefins include, but are not limited to, polymers comprising one or more linear, branched or cyclic C2 to C40 olefins, polymers comprising propylene copolymerized with one or more C3 to C40 olefins, C3 to C20 alpha olefins, or C3 to C10 alpha-olefins. Polyolefins include, but are not limited to, polymers comprising ethylene including but not limited to ethylene copolymerized with a C3 to C40 olefin, a C3 to C20 alpha olefin, or propylene and or butene.

Elastomers include, but are not limited to, ethylene propylene rubber, ethylene propylene diene monomer rubber, styrenic block copolymer rubbers (including SI, SIS, SB, SBS, SIBS and the like, where S=styrene, I=isobutylene, and B=butadiene), butyl rubber, halobutyl rubber, copolymers of isobutylene and para-alkylstyrene, halogenated copolymers of isobutylene and para-alkylstyrene, natural rubber, polyisoprene, copolymers of butadiene with acrylonitrile, polychloroprene, alkyl acrylate rubber, chlorinated isoprene rubber, acrylonitrile chlorinated isoprene rubber, polybutadiene rubber (both cis and trans).

In some variations, a container comprises one or more of polybutene, ethylene vinyl acetate, low density polyethylene (density 0.915 to less than 0.935 g/cm3) linear low density polyethylene, ultra low density polyethylene (density 0.86 to less than 0.90 g/cm3), very low density polyethylene (density 0.90 to less than 0.915 g/cm3), medium density polyethylene (density 0.935 to less than 0.945 g/cm3), high density polyethylene (density 0.945 to 0.98 g/cm3), ethylene vinyl acetate, ethylene methyl acrylate, copolymers of acrylic acid, polymethylmethacrylate or any other polymers polymerizable by a high-pressure free radical process, polyvinylchloride, polybutene-1, isotacetic polybutene, ABS resins, ethylene-propylene rubber (EPR), vulcanized EPR, EPDM, block copolymer, styrenic block copolymers, polyamides, polycarbonates, PET resins, crosslinked polyethylene, copolymers of ethylene and vinyl alcohol (EVOH), polymers of aromatic monomers such as polystyrene, poly-1 esters, polyacetal, polyvinylidine fluoride, polyethylene glycols and/or polyisobutylene. Polymers include those available from Exxon Chemical Company in Baytown, Tex. under the tradenames EXCEED and EXACT.

The containers may be processed or formed by any suitable means. In some variations the container is a low volume syringe. In some variations the low volume syringe is processed or formed via casting, blow molding, compression molding, injection molding, thermoforming, cast molding, rotational molding, or other forms of processing such as described in, for example, PLASTICS PROCESSING (Radian Corporation, Noyes Data Corp. 1986), which is incorporated herein by reference in its entirety.

In some variations the portion of the container that is exposed to the formulation comprises a plastic material that includes but is not limited to a cyclic olefin material. In some variations the cyclic olefin material is a cyclic polyolefin Resin CZ® material.

In some variations the portion of the container that is exposed to the formulation is coated with a material that is different from the material from which the body of the container is made. In some variations the coating is made of a material that does not react or interact with the formulation in such a way as to substantially diminish or change the activity of the formulation. In some variations the therapeutic agent in the formulation is not substantially absorbed or adsorbed onto the surface of the portion of the container with which it is in contact.

In some variations, a formulation is in a sealed vessel and is stable at one or more of 25° C., 5° C., or −20° C. for an extended period of time. In some variations the formulation is in a sealed vessel and is stable for a period of at least about 1, at least about 2, at least about 3, at least about 4, at least about 5, at least about 6, at least about 7, at least about 8, at least about 9, at least about 10, at least about 11, at least about 12, at least about 15, at least about 18, or at least about 24 months at −20° C. In some variations the formulation is in a sealed vessel and is stable for a period of at least about 1, at least about 2, at least about 3, at least about 4, at least about 5, at least about 6, at least about 7, at least about 8, at least about 9, at least about 10, at least about 11, at least about 12, at least about 15, at least about 18, or at least about 24 weeks at 5° C. In some variations the formulation is in a sealed vessel and is stable for a period of at least about 1, at least about 2, at least about 3, at least about 4, at least about 5, at least about 6, at least about 7, at least about 8, at least about 9, at least about 10, at least about 11, at least about 12, at least about 15, at least about 18, or at least about 24 months at 5° C. In some variations the formulation is in a sealed vessel and is stable for a period of at least about 1, at least about 2, at least about 3, at least about 4, at least about 5, at least about 6, at least about 7, at least about 8, at least about 9, at least about 10, at least about 11, at least about 12, at least about 15, at least about 18, or at least about 24 weeks at 25° C.

In some variations the formulation is in a sealed vessel and is at least about 95% stable for a period of at least about 1, at least about 2, at least about 3, at least about 4, at least about 5, at least about 6, at least about 7, at least about 8, or at least about 12 months at minus 20° C. In some variations the formulation is in a sealed vessel and is at least about 95% stable for a period of at least about 1, at least about 2, at least about 3, at least about 4, at least about 5, at least about 6, at least about 7, at least about 8, or at least about 12 months at 5° C. In some variations the formulation is in a sealed vessel and is at least about 95% stable for a period of at least about 1, at least about 2, or at least about 3 months at 25° C.

In some variations the container is a low volume applicator, and the low volume applicator is pre-filled.

In some variations the composition is stable in a pre-filled low volume applicator for at least about 1, at least about 2, at least about 3, at least about 4, at least about 5, at least about 6, at least about 7, at least about 14, at least about 21, at least about 28, or at least about 35 days; at least about 1 month, at least about 2, at least about 3, at least about 4, at least about 5, at least about 6, at least about 7, at least about 8, at least about 9, at least about 10, at least about 11, or at least about 12 months after being filled.

Described herein are containers whose walls are transparent, clear, tinted, opaque, translucent, or combinations thereof. In some variations the walls are translucent and tinted amber. In some variations the formulation container is opaque or translucent to protect the formulation from light or other forms of radiation, with portions that are transparent or translucent.

In some variations at least one of the materials with which the container is constructed is selected to preserve or enhance the stability of the composition. In some variations, the container is designed for containing a formulation wherein the therapeutic agent or other element of the formulation is sensitive to light or other form of radiation. In some variations, the container reduces or attenuates the level, intensity, or form of light or other form of radiation that would otherwise act or impinge upon the formulation. In some variations, the container is designed to reduce or attenuate the level, intensity, or form of UV light, including but not limited to UVA, UVB and UVC.

In some variations, the container has a secondary packaging that preserves or enhances the stability of the composition. In some variations, the secondary packaging reduces or attenuates the level, intensity, or form of light or other form of radiation that would otherwise act or impinge upon the formulation.

In some variations, the secondary packaging limits the exposure of the formulation to one or more components of the air. In some variations, the secondary packaging acts as a barrier to oxygen. In some variations, the secondary packaging is surrounded with an inert gas and impermeable to air. In some variations, the container is in secondary packaging, and the space between the container and the secondary packaging is filled with nitrogen.

In some variations, the container is designed to maintain its integrity and general level of nonreactivity with the formulation when stored at temperatures other than standard room temperature and/or pressure. In some variations the container is prefilled and maintains its integrity and general level of nonreactivity with the formulation when the container is stored at temperatures between about −80° C. and about 40° C.; between about −40° C. and about −10° C.; between about −25° C. and about 10° C.; between about 0° C. and about 20° C.; or between about 20° C. and about 40° C. In some variations the container maintains its integrity and general level of nonreactivity with the formulation when stored in the recited temperature ranges for at least about 1, at least about 2, at least about 3, at least about 4, at least about 5, at least about 6, at least about 7, at least about 8, at least about 9, at least about 10, at least about 11, at least about 12, at least about 15, at least about 18, or at least about 24 months.

In some variations, the container is designed or selected to minimize the surface area to volume ratio. In some variations, the container is designed to minimize the surface area to volume ratio for a fill volume of less than about 5 mls, less than about 4 mls, less than about 3 mls, less than about 2 mls, less than about 1 ml, less than about 0.7 mls, less than about 0.6 mls, less than about 0.5 mls, less than about 0.3 mls, less than about 0.2 mls, less than about 120 µl, less than about 100 µl, less than about 75 µl, less than about 60 µl, less than about 40 µl, less than about 30 µl, less than about 20 µl, less than about 10 µl, less than about 5 µl, less than about 2 µl, between about 0.1 and about 20 µl, between about 0.1 and about 10 µl, between about 0.1 and about 5 µl, between about 0.1 and about 50 µl, between about 50 and about 100 µl, between about 10 and about 200 µl, between about 400 to about 600 µl, between about 0.5 ml and about 1 ml, between about 1 ml and about 2 ml, or between about 1 ml and about 5 ml.

In some variations, a low-volume applicator is pre-filled with a therapeutic agent for treatment of an ophthalmic disease or condition, including but not limited to a limus compound for treatment of age-related macular degeneration. Described herein is a pre-filled low-volume applicator pre-filled with a formulation comprising rapamycin. In some variations a low-volume applicator is pre-filled with a stable formulation comprising rapamycin and a polyethylene glycol, and optionally further comprises one or more additional components including but not limited to ethanol. In some variations a pre-filled low-volume applicator is pre-filled with a stable formulation comprising about 2% rapamycin, about 94% PEG-400, about 4% ethanol.

Described herein are kits comprising one or more containers. In some variations a kit comprises one or more low-volume applicators pre-filled with one or more formulations in liquid form comprising one or more therapeutic agents, including but not limited to formulations in liquid form comprising rapamycin, formulations in liquid form comprising rapamycin and a polyethylene glycol, and optionally further comprises one or more additional components including but not limited to ethanol, and formulations in liquid form comprising about 2% rapamycin, about 94% PEG-400, about 4% ethanol. In some variations the kit comprises one or more containers, including but not limited to pre-filled low-volume applicators, with instructions for its use. In a further variation a kit comprises one or more low-volume applicators pre-filled with rapamycin, with instructions for its use in treating a disease or condition of the eye.

In some variations, the containers described herein are in a secondary packaging. In some variations the secondary packaging that is configured to preserve the stability of the therapeutic agent relative to the stability of the therapeutic agent prior to packaging. In some variations, the secondary packaging is designed to exclude or reduce exposure of the formulation to light. In some variations, the secondary packaging is designed to exclude or reduce exposure of the formulation to one or more components of the air, such as oxygen. In some variations, the container is an ampule, vial, or prefilled syringe. In some variations, the container is a low volume applicator such as that described in U.S. provisional patent application No. 60/725,934, filed Oct. 11, 2005 with attorney docket number 57796-30009.00.

In some variations, some or all of steps 110-160 are performed in a glove box, clean room, or other controlled environment. In some variations the solution is manipulated in a sterile environment. In some variations the solution is manipulated under a nitrogen blanket. In some variations the solution is manipulated under a layer of an inert or noble gas, including but not limited to nitrogen, argon or helium. In some variations the inert gas blankets the surface of the solution as the solution is placed in the container.

For example, in some variations one or more steps are performed under nitrogen or other inert gas atmosphere to prevent or reduce contact of the liquid formulation and its ingredients with water, water vapor, and oxygen.

In some variations the grade of inert gas is medical grade. In some variations the inert gas is a medical grade noble gas. In some variations the inert gas is medical grade compressed nitrogen. It is believed that in some variations the stability of the liquid formulation may be thereby enhanced.

In some variations, a container or containers of a filtered solution is stable at a temperature of about −20° C., 5° C., or 25° C. for a period of at least about one week, at least about two weeks, at least about three weeks, at least about four weeks, at least about one month, at least about two months, at least about three months, at least about four months, at least about five months, at least about six months, at least about seven months, at least about eight months, at least about nine months, at least about ten months, at least about eleven months, at least about twelve months, at least about 14 months, at least about 16 months, at least about 18 months, at least about 20 months, at least about 22 months, at least about 24 months, at least about three years, at least about four years, or at least about five years. In some variations, the solution is stable at a temperature of about −20° C. for a period of at least about 3 months, at least about 6 months, at least about 9 months, or at least about 12 months. In some variations, the solution is stable at a temperature of about 5° C. for a period of at least about 1 week, at least about 2 weeks, at least about 4 weeks, at least about 1 month, at least about 2 months, at least about 3 months, at least about 6 months, at least about 9 months, at least about 12 months, at least about 18 months, or at least about 24 months.

In some variations, stability is measured relative to the amount of therapeutic agent at the time the solution is prepared. Therapeutic agent stability may be measured using mass spectrometry or HPLC.

In some variations, the formulations described herein are provided in one or more unit dose forms, wherein the unit dose form contains an amount of a liquid rapamycin formulations described herein that is effective to treat or prevent the disease or condition for which it is being administered.

In some embodiments, the unit dose form is prepared in the concentration at which it will be administered. In some variations, the unit dose form is diluted prior to administration to a subject.

In a further aspect, provided herein are kits comprising one or more unit dose forms as described herein. In some embodiments, the kit comprises one or more of packaging and instructions for use to treat one or more diseases or conditions. In some embodiments, the kit comprises a diluent which is not in physical contact with the formulation or pharmaceutical formulation. In some embodiments, the kit comprises any of one or more unit dose forms described herein in one or more sealed vessels. In some embodiments, the kit comprises any of one or more sterile unit dose forms.

Diseases and Conditions that May be Treated, Prevented, Inhibited, Onset Delayed, or Regression Caused Described herein are nonlimiting examples of diseases and conditions that may be treated, prevented, inhibited, onset delayed, or regression caused using the therapeutic agents and the formulations, liquid formulations, and methods described herein. In some variations, the diseases or conditions are treated using the therapeutic agents and the formulations, liquid formulations, and methods described herein. Unless the context indicates otherwise, it is envisioned that the subjects on whom all of the methods of treatment may be performed include human subjects.

Generally, any diseases or condition of the eye susceptible to treatment, prevention, inhibition, delaying the onset of, or causing the regression of using the therapeutic agents and the formulations, liquid formulations and methods described herein may be treated, prevented, inhibited, onset delayed, or regression caused treated or prevented. Examples of diseases or conditions of the eye include, but are not limited to, diseases or conditions associated with neovascularization including retinal and/or choroidal neovascularization.

The following references, each of which is incorporated herein by reference in its entirety, show one or more formulations, including but not limited to rapamycin formulations, which may be made stable by the methods described herein, and which describe use of rapamycin at various doses and other therapeutic agents for treating various diseases or conditions: U.S. 60/651,790, filed Feb. 9, 2005, titled FORMULATIONS FOR OCULAR TREATMENT; U.S. 60/664,040, filed Feb. 9, 2005, titled LIQUID FORMULATIONS FOR TREATMENT OF DISEASES OR CONDITIONS; U.S. 60/664,119, filed Mar. 21, 2005, titled DRUG DELIVERY SYSTEMS FOR TREATMENT OF DISEASES OR CONDITIONS; U.S. 60/664,306, filed Mar. 21, 2005, titled 1N SITU GELLING FORMULATIONS AND LIQUID FORMULATIONS FOR TREATMENT OF DISEASES OR CONDITIONS; U.S. Ser. No. 11/351,844, filed Feb. 9, 2006, titled FORMULATIONS FOR OCULAR TREATMENT; U.S. Ser. No. 11/351,761, filed Feb. 9, 2006, titled LIQUID FORMULATIONS FOR TREATMENT OF DISEASES OR CONDITIONS; U.S. Ser. No. 11/386,290, filed Mar. 21, 2006, titled DRUG DELIVERY SYSTEMS FOR TREATMENT OF DISEASES OR CONDITIONS; U.S. Ser. No. 11/352,092, filed Feb. 9, 2006, entitled RAPAMYCIN FORMULATIONS AND METHODS OF THEIR USE; U.S. 60/772,018, filed Feb. 9, 2006, titled STABLE FORMULATIONS, AND METHODS OF THEIR PREPARATION AND USE; US 2005/0187241, and US 2005/0064010.

Diseases or conditions associated with retinal and/or choroidal neovascularization that can be treated, prevented inhibited, have onset delayed, or be caused to regress using the formulations, liquid formulations, and methods described herein include, but are not limited to, diabetic retinopathy, macular degeneration, wet and dry AMD, retinopathy of prematurity (retrolental fibroplasia), infections causing a retinitis or choroiditis, presumed ocular histoplasmosis, myopic degeneration, angioid streaks, and ocular trauma. Other nonlimiting examples of diseases and conditions of the eye that may be treated, prevented inhibited, have onset delayed, or be caused to regress using the formulations, liquid formulations, and methods described herein include, but are not limited to, pseudoxanthoma elasticum, vein occlusion, artery occlusion, carotid obstructive disease, Sickle Cell anemia, Eales disease, myopia, chronic retinal detachment, hyperviscosity syndromes, toxoplasmosis, trauma, polypoidal choroidal vasculopathy, post-laser complications, complications of idiopathic central serous chorioretinopathy, complications of choroidal inflammatory conditions, rubeosis, diseases associated with rubeosis (neovascularization of the angle), neovascular glaucoma, uveitis and chronic uveitis, macular edema, proliferative retinopathies and diseases or conditions caused by the abnormal proliferation of fibrovascular or fibrous tissue, including all forms of proliferative vitreoretinopathy (including post-operative proliferative vitreoretinopathy), whether or not associated with diabetes.

In some variations, the formulations and pharmaceutical formulations described herein are used to prevent or delay onset of a disease or condition of the eye where the subject, including but not limited to a human subject, is at heightened risk of developing the disease or condition of the eye. A subject with a heightened risk of developing a disease or condition is a subject with one or more indications that the disease or condition is likely to develop in the particular subject. In some variations the subject with a heightened risk of developing wet AMD is a subject with dry AMD in at least one eye. In some variations the subject with a heightened risk of developing wet AMD in a fellow eye is a subject with wet AMD in the other eye. In some variations, the formulations and pharmaceutical formulations described herein are used to prevent or delay onset of CNV in a subject at heightened risk of developing CNV, including but not limited to prevention or delaying onset of CNV in the fellow eye of a subject, including but not limited to a human subject, with AMD in one eye. In some variations, the formulations and pharmaceutical formulations described herein are used to prevent or delay onset of CNV in the fellow eye of a subject with wet AMD in one eye. In some variations, the formulations and pharmaceutical formulations comprise a limus compound, including but not limited to rapamycin. In some variations the formulations and pharmaceutical formulations are administered subconjunctivally to an eye with vision of 20/40 or better.

In some variations, the formulations and pharmaceutical formulations described herein are used to treat, prevent, or delay onset of AMD. In some variations, the formulations and pharmaceutical formulations described herein are used to treat, prevent, or delay onset of dry AMD. In some variations subjects, including but not limited to human subjects, with non-central geographic atrophy are administered a formulation or pharmaceutical formulations described herein to treat, prevent, or delay onset of central geographic atrophy. In some variations, the formulations and pharmaceutical formulations comprise a limus compound, including but not limited to rapamycin. In some variations the formulations and pharmaceutical formulations are administered subconjunctivally to an eye with vision of 20/40 or better. In some variations, the formulations and pharmaceutical formulations described herein are administered and the subject, including but not limited to a human subject is also treated with a second therapy for treating the disease or disorder. In some variations, the formulations and pharmaceutical formulations described herein are used to treat, prevent, or delay onset of wet or dry AMD and the subject, including but not limited to a human subject is also treated with laser therapy such as photodynamic laser therapy, either before, during, or after treatment with the formulations or pharmaceutical formulations described herein.

In some variations, the formulations and pharmaceutical formulations described herein are used to treat one or more of uveitis, allergic conjunctivitis, macular edema, glaucoma, or dry eye.

In some variations, a formulations or pharmaceutical formulation comprises a limus compound such as rapamycin, and is administered to treat, prevent, or delay onset of dry eye. In some variations, a formulations or pharmaceutical formulation comprises a limus compound such as rapamycin, and is administered to treat, prevent, or delay onset of allergic conjunctivitis.

In some variations, the formulations and pharmaceutical formulations described herein are used to treat glaucoma. In some variations, the formulations and pharmaceutical formulations described herein for treating glaucoma comprise a limus compound such as rapamycin, and are used as a surgical adjuvant to prevent, reduce or delay surgical complications. In some variations, the formulations and pharmaceutical formulations described herein for treating glaucoma comprise a limus compound such as rapamycin, and are used to improve or prolong surgical implant success. In some variations, the formulations and pharmaceutical formulations described herein for treating glaucoma comprise a limus compound such as rapamycin, and are used to improve or prolong success of an argon laser trabeculectomy or other glaucoma-related surgery. In some variations, the formulations and pharmaceutical formulations described herein have a neuroprotective effect and are used to treat glaucoma.

In some variations, the formulations and pharmaceutical formulations described herein are used to treat retinitis pigmentosa. In some variations, the formulations and pharmaceutical formulations described herein for treating glaucoma comprise a limus compound such as rapamycin, and are used to treat, prevent, or delay onset of retinitis pigmentosa. In some variations, the formulations and pharmaceutical formulations described herein have a neuroprotective effect and are used to treat retinitis pigmentosa.

In some variations, the formulations and pharmaceutical formulations described herein are used to treat one or more of central retinal vein occlusive diseases (CRVO), branch retinal venous occlusion (BRVO), retinal vascular diseases and conditions, macular edema, diabetic macular edema, iris neovascularization, diabetic retinopathy, corneal neovascularization, or corneal graft rejection. In some variations, a formulations or pharmaceutical formulation comprises a limus compound such as rapamycin, and is administered to treat, prevent, or delay onset of one or more of these diseases or conditions. In some variations the formulations and pharmaceutical formulations are administered subconjunctivally to an eye with vision of 20/40 or better.

When used to treat, prevent, inhibit, delay the onset of, or cause regressions of uveitis, the formulations and pharmaceutical formulations described herein may be administered by a variety of routes as is known in the art, including but not limited to by ocular or oral administration. Other routes of administration are known and are routine in the art. In some variations, the formulations described herein comprise rapamycin and are used to treat uveitis.

One disease that may be treated, prevented, inhibited, have onset delayed, or be caused to regress using the formulation, liquid formulations and methods described herein is the wet form of AMD. In some variations wet AMD is treated using the formulations, liquid formulations and methods described herein. The wet form of AMD is characterized by blood vessels growing from their normal location in the choroid into an undesirable position under the retina. Leakage and bleeding from these new blood vessels results in vision loss and possibly blindness.

The formulations, liquid formulations, and methods described herein may also be used to prevent or slow the transition from the dry form of AMD (wherein the retinal pigment epithelium or RPE degenerates and leads to photoreceptor cell death and the formation of yellow deposits called drusen under the retina) to the wet form of AMD.

"Macular degeneration" is characterized by the excessive buildup of fibrous deposits in the macula and retina and the atrophy of the retinal pigment epithelium. As used herein, an eye "afflicted" with macular degeneration is understood to mean that the eye exhibits at least one detectable physical characteristic associated with the disease of macular degeneration. The administration of rapamycin appears to limit and regress angiogenesis, such as choroidal neovascularization in age-related macular degeneration (AMD), which may occur without treatment. As used herein, the term "angiogenesis" means the generation of new blood vessels ("neovascularization") into a tissue or organ. An "angiogenesis-mediated disease or condition" of the eye or retina is one in which new blood vessels are generated in a pathogenic manner in the eye or retina, resulting in diminution or loss of vision or other problem, e.g., choroidal neovascularization associated with AMD.

The formulations and liquid formulations described herein, including but not limited to rapamycin-containing formulations and liquid formulations, may also be used to treat, prevent, inhibit, delay the onset of, or cause regression of various immune-related diseases and conditions, including but not limited to organ transplant rejection in a host, graft vs. host disease, autoimmune diseases; diseases of inflammation, hyperproliferative vascular disorders, solid tumors, ocular tumors, and fungal infections. In some variations, the formulations and liquid formulations described herein, including but not limited to rapamycin-containing formulations and liquid formulations, are used to treat various immune-related diseases and conditions, including but not limited to organ transplant rejection in a host, graft vs. host disease, and autoimmune diseases; diseases of inflammation, hyperproliferative vascular disorders, solid tumors, ocular tumors, and fungal infections. The formulations and liquid formulations described herein, including but not limited to rapamycin-containing formulations and liquid formulations, may be used as immunosuppressants. The formulations and liquid formulations described herein, including but not limited to rapamycin-containing formulations and liquid formulations, may be used to treat, prevent, inhibit, or delay the onset of rejection of transplanted organs or tissues including but not limited to transplanted heart, liver, kidney, spleen, lung, small bowel, pancreas, and bone marrow. In some variations, the formulations and liquid formulations described herein are used to treat the onset of rejection of transplanted organs or tissues including but not limited to transplanted heart, liver, kidney, spleen, lung, small bowel, pancreas, and bone marrow. When used to treat, prevent, inhibit, delay the onset of, or cause regressions of immune-related diseases, including but not limited to transplant rejection, the formulations and liquid formulations described herein may be administered by a variety of routes as is known in the art, including but not limited to by oral administration.

Systemic administration may be achieved by oral administration of the liquid formulation. Other systemic routes of administration are known and are routine in the art. Some examples thereof are listed in the Detailed Description section.

As used herein, to "inhibit" a disease or condition by administration of a therapeutic agent means that the progress of at least one detectable physical characteristic or symptom of the disease or condition is slowed or stopped following administration of the therapeutic agent as compared to the progress of the disease or condition without administration of the therapeutic agent.

As used herein, to "prevent" a disease or condition by administration of a therapeutic agent means that the detectable physical characteristics or symptom of the disease or condition do not develop following administration of the therapeutic agent.

As used herein, to "delay onset of" a disease or condition by administration of a therapeutic agent means that at least one detectable physical characteristic or symptom of the disease or condition develops later in time following administration of the therapeutic agent as compared to the progress of the disease or condition without administration of the therapeutic agent.

As used herein, to "treat" a disease or condition by administration of a therapeutic agent means that the progress of at least one detectable physical characteristic or symptom of the disease or condition is slowed, stopped, or reversed following administration of the therapeutic agent as compared to the progress of the disease or condition without administration of the therapeutic agent.

As used herein, to "cause regression of" a disease or condition by administration of a therapeutic agent means that the progress of at least one detectable physical characteristic or symptom of the disease or condition is reversed to some extent following administration of the therapeutic agent.

A subject, including but not limited to a human subject, having a predisposition for or in need of prevention may be identified by the skilled practitioner by established methods and criteria in the field given the teachings herein. The skilled practitioner may also readily diagnose individuals as in need of inhibition or treatment based upon established criteria in the field for identifying angiogenesis and/or neovascularization given the teachings herein.

As used herein, a "subject" is generally any animal that may benefit from administration of the therapeutic agents described herein. In some variations the therapeutic agents are administered to a mammalian subject. In some variations the therapeutic agents are administered to a human subject. In some variations the therapeutic agents may be administered to a veterinary animal subject. In some variations the therapeutic agents may be administered to a model experimental animal subject.

Other diseases and conditions that may be treated, prevented, inhibited, have the onset delayed, or be caused to regress using the methods described herein include those disclosed in the following patents and publications, the contents of each of which is incorporated herein in its entirety: PCT publication WO 2004/027027, published Apr. 1, 2004, titled Method of inhibiting choroidal neovascularization, assigned to Trustees of the University of Pennsylvania; U.S. Pat. No. 5,387,589, issued Feb. 7, 1995, titled Method of Treating Ocular Inflammation, with inventor Prassad Kulkarni, assigned to University of Louisville Research Foundation; U.S. Pat. No. 6,376,517, issued Apr. 23, 2003, titled Pipecolic acid derivatives for vision and memory disorders, assigned to GPI NIL Holdings, Inc; PCT publication WO 2004/028477, published Apr. 8, 2004, titled Method subretinal administration of therapeutics including steroids: method for localizing pharmadynamic action at the choroid and retina; and related methods for treatment and or prevention of retinal diseases, assigned to Innorx, Inc; U.S. Pat. No.

6,416,777, issued Jul. 9, 2002, titled Ophthalmic drug delivery device, assigned to Alcon Universal Ltd; U.S. Pat. No. 6,713,081, issued Mar. 30, 2004, titled Ocular therapeutic agent delivery device and methods for making and using such devices, assigned to Department of Health and Human Services; and U.S. Pat. No. 5,536,729, issued Jul. 16, 1996, titled Rapamycin Formulations for Oral Administration, assigned to American Home Products Corp.

Routes of Administration

The formulations, methods, and liquid formulations described herein deliver one or more therapeutic agents to a subject, including but not limited to a human subject.

In some variations, the formulations, methods, and liquid formulations described herein deliver one or more therapeutic agents to an aqueous medium of a subject, including but not limited to a human subject.

In some variations, the formulations, methods, and liquid formulations described herein deliver one or more therapeutic agents to an aqueous medium in or proximal to an area where a disease or condition is to be treated, prevented, inhibited, onset delayed, or regression caused.

The liquid formulations may generally be administered in any volume that has the desired effect; in some variations a liquid formulation is administered to the vitreous and the liquid formulation is less than one half the volume of the vitreous. In some variations the liquid formulation is administered between the sclera and conjunctiva in a volume less than about 50 μl.

When a certain volume is administered, it is understood that there is some imprecision in the accuracy of various syringes that may be used to administer the liquid formulation. Where a certain volume is specified, it is understood that this is the target volume. However, certain syringes such as insulin syringes are inaccurate to greater than 10%, and sometimes inaccurate up to 20% or more. Hamilton HPLC type syringes are generally considered precise to within 10%, and are recommended for volumes below 10 μl.

In some variations, a volume of a liquid formulation described herein is administered to the vitreous of a rabbit eye or a subject's eye that is less than about 200 μl, less than about 100 μl, less than about 90 μl, less than about 80 μl, less than about 70 μl, less than about 60 μl, less than about 50 μl, less than about 40 μl, less than about 30 μl, less than about 20 μl, less than about 10 μl, less than about 5 μl, less than about 3 μl, or less than about 1 μl. In some variations, a volume of a liquid formulation described herein is administered to the vitreous of a rabbit eye or subject's eye that is less than about 20 μl. In some variations, a volume of a liquid formulation described herein is administered to the vitreous that is less than about 10 μl. In some variations, a volume of a liquid formulation described herein is administered to the vitreous of a rabbit eye or a subject's eye that is between about 0.1 μl and about 200 μl, between about 50 μl and about 200 μl, between about 50 μl and about 150 μl, between about 0.1 μl and about 100 μl, between about 0.1 μl and about 50 μl, between about 1 μl and about 40 μl, between about 1 μl and about 30 μl, between about 1 μl and about 20 μl, between about 1 μl and about 10 μl, or between about 1 μl and about 5 μl. In some variations, a volume of a liquid formulation described herein is administered to the vitreous of a rabbit eye or a subject's eye that is between about 1 μl and about 10 μl. In some variations, a volume of a liquid formulation described herein is administered to the vitreous of a rabbit eye or a subject's eye that is between about 1 μl and about 5 μl. In some variations, a volume of a liquid formulation described herein is administered to the vitreous of a rabbit eye or a subject's eye that is between about 1 μl and about 5 μl. In some variations, a volume of a liquid formulation described herein is administered to the vitreous of a rabbit eye or a subject's eye that is between about 0.1 μl and about 200 μl.

In some variations, a total volume of a liquid formulation described herein is subconjunctivally administered to a rabbit eye or a subject's eye that is less than about 1000 μl, less than about 600 μl, less than about 500 μl, less than about 400 μl, less than about 200 μl, less than about 100 μl, less than about 90 μl, less than about 80 μl, less than about 70 μl, less than about 60 μl, less than about 50 μl, less than about 40 μl, less than about 30 μl, less than about 20 μl, less than about 10 μl, less than about 5 μl, less than about 3 μl, or less than about 1 μl. In some variations, a volume of a liquid formulation described herein is subconjunctivally administered to a rabbit eye or a subject's eye that is less than about 20 μl. In some variations, a volume of a liquid formulation described herein is subconjunctivally administered to a rabbit eye or a subject's eye that is less than about 10 μl. In some variations, a volume of a liquid formulation described herein is subconjunctivally administered to a rabbit eye or a subject's eye that is between about 0.1 μl and about 200 μl, between about 50 μl and about 200 μl, between about 100 μl and about 300 μl, between about 300 μl and about 400 μl, between about 400 μl and about 500 μl, between about 500 μl and about 1000 μl, between about 50 μl and about 150 μl, between about 0.1 μl and about 100 μl, between about 0.1 μl and about 50 μl, between about 1 μl and about 40 μl, between about 1 μl and about 30 μl, between about 1 μl and about 20 μl, between about 1 μl and about 10 μl, or between about 1 μl and about 5 μl. In some variations, a volume of a liquid formulation described herein is subconjunctivally administered to a rabbit eye or a subject's eye that is between about 1 μl and about 10 μl. In some variations, a volume of a liquid formulation described herein is subconjunctivally administered to a rabbit eye or a subject's eye that is between about 1 μl and about 5 μl. In some variations, a volume of a liquid formulation described herein is administered to subconjunctivally administered to a rabbit eye or a subject's eye that is between about 1 μl and about 5 μl. In some variations, a volume of a liquid formulation described herein is administered to subconjunctivally administered to a rabbit eye or a subject's eye that is between about 0.1 μl and about 200 μl.

In some variations the liquid formulations described herein contain no greater than about 250 μl of polyethylene glycol. In some variations the liquid formulations described herein contain no greater than about 250 μl, no greater than about 200 μl, no greater than about 150 μl, no greater than about 125 μl, no greater than about 100 μl, no greater than about 75 μl, no greater than about 50 μl, no greater than about 25 μl, no greater than about 20 μl, no greater than about 15 μl, no greater than about 10 μl, no greater than about 7.5 μl, no greater than about 5 μl, no greater than about 2.5 μl, no greater than about 1.0 μl, or no greater than about 0.5 μl of polyethylene glycol. Formulations containing polyethylene glycol may contain, for example, PEG 300 or PEG 400.

In some variations the liquid formulations described herein are administered in multiple subconjunctival locations within some period of time, including without limitation within an hour of one another. Without being bound by theory, it is thought that such multiple administrations, such as multiple injections, allow for a greater total dose to be administered subconjunctivally than a single dose due to a potentially limited ability of the local ocular tissues to absorb larger volumes.

In some variations, the formulations, methods, and liquid formulations described herein deliver one or more therapeutic agents to an eye of a subject, including the macula and the retina choroid tissues, in an amount and for a duration effective to treat, prevent, inhibit, delay the onset of, or cause the regression of the diseases and conditions described in the Diseases and Conditions section.

"Retina choroid" and "retina choroid tissues," as used herein, are synonymous and refer to the combined retina and choroid tissues of the eye.

"Subconjunctival" placement or injection, as used herein, refers to placement or injection between the sclera and conjunctiva.

As a non-limiting example, the formulations, liquid formulations, and methods described herein may be administered to the vitreous, aqueous humor, sclera, conjunctiva, between the sclera and conjunctiva, the retina choroid tissues, macula, or other area in or proximate to the eye of a subject, either by direct administration to these tissues or by periocular routes, in amounts and for a duration effective to treat, prevent, inhibit, delay the onset of, or cause the regression of CNV and wet AMD. Other nonlimiting routes of administration to reach the target tissues include but are not limited to intravitreal, intracameral, and periocular routes. The effective amounts and durations may be different for each of treating, preventing, inhibiting, delaying the onset of, or causing the regression of CNV and wet AMD, and for each of the different sites of delivery.

Intravitreal administration is more invasive than some other types of ocular procedures. Because of the potential risks of adverse effects, intravitreal administration may not be optimal for treatment of relatively healthy eyes. By contrast, periocular administration, such as subconjunctival administration, is much less invasive than intravitreal administration. When a therapeutic agent is delivered by a periocular route, it may be possible to treat patients with healthier eyes than could be treated using intravitreal administration. In some variations, subconjunctival injection is used to prevent or delay onset of a disease or condition of the eye, where the eye of the subject has visual acuity of 20/40 or better.

Routes of administration that may be used to administer a liquid formulation include but are not limited to placement of the liquid formulation, for example by injection, into an aqueous medium in the subject, including but not limited to placement, for example by injection, into the eye of a subject. The liquid formulation may be administered systemically, including but not limited to the following delivery routes: rectal, vaginal, infusion, intramuscular, intraperitoneal, intraarterial, intrathecal, intrabronchial, intracisternal, cutaneous, subcutaneous, intradermal, transdermal, intravenous, intracervical, intraabdominal, intracranial, intraocular, intrapulmonary, intrathoracic, intratracheal, nasal, buccal, sublingual, oral, parenteral, or nebulised or aerosolized using aerosol propellants. In some variations, the self-emulsifying formulation is administered subconjunctivally. In some variations, the self-emulsifying formulation is administered intravitreally.

Compositions and liquid formulations comprising therapeutic agent can be administered directly to the eye using a variety of procedures, including but not limited to procedures in which (1) the therapeutic agent is administered by injection using a syringe and hypodermic needle, (2) a specially designed device is used to inject the therapeutic agent, (3) prior to injection of the therapeutic agent, a pocket is surgically formed within the sclera to serve as a receptacle for the therapeutic agent or therapeutic agent composition. For example, in one administration procedure a surgeon forms a pocket within the sclera of the eye followed by injection of a solution or liquid formulation comprising the therapeutic agent into the pocket.

Other administration procedures include, but are not limited to procedures in which (1) a formulation of the therapeutic agent is injected through a specially designed curved cannula to place the therapeutic agent directly against a portion of the eye, (2) a compressed form of the therapeutic agent is placed directly against a portion of the eye, (3) the therapeutic agent is inserted into the sclera by a specially designed injector or inserter, (4) the liquid formulation comprising the therapeutic agent is incorporated within a polymer, (5) a surgeon makes a small conjunctival incision through which to pass a suture and any therapeutic agent delivery structure so as to secure the structure adjacent to the sclera, (6) a needle is used for injection directly into the vitreous of an eye, or into any other site described.

The liquid formulations described herein may be used by injection, as an elixir, for topical administration, including but not limited to topical administration to the eye via eye drops or other method. In some variations the liquid formulations described herein are in hard or soft gelatin or starch capsules. The capsules may be banded, for example to prevent leakage.

Some variations that may be used to deliver the formulations and liquid formulations described herein is delivery by injection. In this method formulations and liquid formulations may be injected into a subject or into a position in or proximate to an eye of the subject for delivery to a subject or to the eye of a subject. Nonlimiting examples of positions that are in or proximate to an eye of a subject are as follows.

Injection of therapeutic agent into the vitreous may provide a high local concentration of therapeutic agent in the vitreous and retina. Further, it has been found that in the vitreous the clearance half-lives of drugs increases with molecular weight.

Intracameral injection, or injection into the anterior chamber of they eye, may also be used. In one example, up to about 100 µl may be injected intracamerally.

Periocular routes of delivery may deliver therapeutic agent to the retina without some of the risks of intravitreal delivery. Periocular routes include but are not limited to subconjunctival, subtenon, retrobulbar, peribulbar and posterior juxtascleral delivery. A "periocular" route of administration means placement near or around the eye. For a description of exemplary periocular routes for retinal drug delivery, see *Periocular routes for retinal drug delivery*, Raghava et al. (2004), Expert Opin. Drug Deliv. 1(1):99-114, which is incorporated herein by reference in its entirety.

In some variations the liquid formulations described herein are administered intraocularly. Intraocular administration includes placement or injection within the eye, including in the vitreous.

Subconjunctival injection may be by injection of therapeutic agent underneath the conjunctiva, or between the sclera and conjunctiva. In one example, up to about 500 µl may be injected subconjunctivally. As one nonlimiting example, a needle of up to about 25 to about 30 gauge and about 30 mm long may be used. Local pressure to the subconjunctival site of therapeutic agent administration may elevate delivery of the therapeutic agent to the posterior segment by reducing local choroidal blood flow.

Subtenon injection may be by injection of therapeutic agent into the tenon's capsule around the upper portion of the eye and into the "belly" of the superior rectus muscle. In one example, up to about 4 ml may be injected subtenon. As one nonlimiting example, a blunt-tipped cannula about 2.5 cm long may be used.

Retrobulbar injection refers to injection into the conical compartment of the four rectus muscles and their intermuscular septa, behind the globe of the eye. In one example, up to about 5 ml may be injected retrobulbarly. As one nonlimiting example, a blunt needle of about 25- or about 27-gauge may be used.

Peribulbar injection may be at a location external to the confines of the four rectus muscles and their intramuscular septa, i.e., outside of the muscle cone. A volume of, for example, up to about 10 ml may be injected peribulbarly. As one nonlimiting example, a blunt-tipped cannula about 1.25 inches long and about 25-gauge may be used.

Posterior juxtascleral delivery refers to placement of a therapeutic agent near and above the macula, in direct contact with the outer surface of the sclera, and without puncturing the eyeball. In one example, up to about 500 ml may be injected posterior juxtascierally. As one nonlimiting example, a blunt-tipped curved cannula, specially designed at 56°, is used to place the therapeutic agent in an incision in the sclera.

For a description of exemplary methods of injection via periocular routes for retinal drug delivery, see Periocular routes for retinal drug delivery, Raghava et al. (2004), Expert Opin. Drug Deliv. 1(1):99-114, which is incorporated herein by reference in its entirety.

Sites to which the formulations and liquid formulations may be administered include but are not limited to the vitreous, aqueous humor, sclera, conjunctiva, between the sclera and conjunctiva, the retina choroid tissues, macula, or other periocular area. Methods that may be used for placement of the formulations and liquid formulations include but are not limited to injection.

In some variations that may be used, the therapeutic agent is dissolved in an solvent or solvent mixture and then injected into or proximate to the vitreous, aqueous humor, sclera, conjunctiva, between the sclera and conjunctiva, the retina choroid tissues, macula, other area in or proximate to the eye of a subject, or other medium of a subject, according to any of the procedures mentioned above. In one such method that may be used, the therapeutic agent is rapamycin in a liquid formulation. In some variations, the liquid formulation is an in situ gelling formulation.

When the therapeutic agent is rapamycin, the compositions and liquid formulations may be used to deliver or maintain an amount of rapamycin in tissues of the eye, including without limitation retina, choroid, or the vitreous, which amount is effective to treat AMD. In one nonlimiting example, it is believed that a liquid formulation delivering rapamycin in an amount capable of providing a concentration of rapamycin of about 0.01 pg/ml to about 2 µg/ml in the vitreous may be used for treatment of wet AMD. In another nonlimiting example, it is believed that a liquid formulation delivering a concentration of rapamycin of about 0.01 pg/mg to about 1 µg/mg in the retina choroid tissues may be used for treatment of wet AMD. Other effective concentrations are readily ascertainable by those of skill in the art based on the teachings described herein.

The formulations and liquid formulations described herein may be delivered to a variety of positions in the ocular region to enable delivery of the therapeutic agent, including but not limited to intraocular or periocular delivery; delivery to the vitreous, aqueous humor, sclera, conjunctiva, between the sclera and conjunctiva, the retina choroid tissues, macula, periocular tissue, tenons areas, and other area in or proximate to the eye of a subject or other environment. Other sites of delivery and routes of administration, such as systemic routes, are described above.

Formulations and liquid formulations comprising therapeutic agent can be administered directly to the eye using a variety of procedures, including but not limited to procedures in which (1) the therapeutic agent is administered by injection using a syringe and hypodermic needle, (2) a specially designed device is used to inject the therapeutic agent, (3) prior to injection of the therapeutic agent, a pocket is surgically formed within the sclera to serve as a receptacle for the therapeutic agent or therapeutic agent formulation. For example, in one administration procedure a surgeon forms a pocket within the sclera of the eye followed by injection of a solution or liquid formulation comprising the therapeutic agent into the pocket.

Other administration procedures include, but are not limited to procedures in which (1) a formulation of the therapeutic agent is injected through a specially designed curved cannula to place the therapeutic agent directly against a portion of the eye, (2) a compressed form of the therapeutic agent is placed directly against a portion of the eye, (3) the therapeutic agent is inserted into the sclera by a specially designed injector or inserter, (4) the liquid formulation comprising the therapeutic agent is incorporated within a polymer, (5) a surgeon makes a small conjunctival incision through which to pass a suture and any therapeutic agent delivery structure so as to secure the structure adjacent to the sclera, (6) a needle is used for injection directly into the vitreous of an eye, or into any other site described.

Intravitreal and Subconjunctival Delivery of Rapamycin for Treatment, Prevention, Inhibition, Delay of Onset, or Cause of Regression of AMD In some variations described herein, a stable formulation comprising rapamycin is delivered subconjunctivally or to the vitreous of an eye of a subject, including but not limited to a human subject, to prevent, treat, inhibit, delay onset of, or cause regression of angiogenesis in the eye, including but not limited to treating CNV as observed, for example, in AMD. In some variations, the stable formulation is used to treat angiogenesis in the eye, including but not limited to treating CNV as observed, for example, in AMD. Rapamycin has been shown to inhibit CNV in rat and mice models, as described in U.S. application Ser. No. 10/665,203, which is incorporated herein by reference in its entirety. Rapamycin has been observed to inhibit Matrigel™ and laser-induced CNV when administered systemically and subretinally.

Other therapeutic agents that may be delivered to the eye, including without limitation the vitreous of an eye, for treatment, prevention, inhibition, delaying onset, or causing regression of angiogenesis in the eye (such as CNV) are members of the limus family of compounds other than rapamycin including but not limited to everolimus and tacrolimus (FK-506).

As described herein, the dosage of the therapeutic agent will depend on the condition being addressed, whether the condition is to be treated, prevented, inhibited, have onset delayed, or be caused to regress, the particular therapeutic agent, and other clinical factors such as weight and condition of the subject and the route of administration of the therapeutic agent. It is to be understood that the methods, liquid formulations including in situ gelling formulations, and formulations described herein have application for both human and veterinary use, including but not limited to laboratory, experimental, pet, or agriculturally important animals. As described herein, tissue concentrations of therapeutic agents expressed in units of mass per volume generally refer to tissues that are primarily aqueous such as the vitreous, for example. Tissue concentrations of therapeutic agents expressed in unit of mass per mass generally refer to other tissues such as the sclera or retina choroid tissues, for example.

One concentration of rapamycin that may be used in the methods described herein is one that provides to a subject about 0.01 pg/ml or pg/mg or more of rapamycin at the tissue level. Another concentration that may be used is one that provides to a subject about 0.1 pg/ml or pg/mg or more at the tissue level. Another concentration that may be used is one that provides to a subject about 1 pg/ml or pg/mg or more at the tissue level. Another concentration that may be used is one that provides to a subject about 0.01 ng/ml or ng/mg or more at the tissue level. Another concentration that may be used is one that provides to a subject about 0.1 ng/ml or ng/mg or more at the tissue level. Another concentration that may be used is one that provides to a subject about 0.5 ng/ml or ng/mg or more at the tissue level. Another concentration that may be used is one that provides to a subject about 1 ng/ml or ng/mg or more at the tissue level. Another concentration that may be used is one that provides to a subject about 2 ng/ml or ng/mg or more at the tissue level. Another concentration that may be used is one that provides to a subject about 3 ng/ml or ng/mg or more at the tissue level. Another concentration that may be used is one that provides to a subject about 5 ng/ml or ng/mg or more at the tissue level. Another concentration that may be used is one that provides to a subject about 10 ng/ml or ng/mg or more at the tissue level. Another concentration that may be used is one that provides to a subject about 15 ng/ml or ng/mg or more at the tissue level. Another concentration that may be used is one that provides to a subject about 20 ng/ml or ng/mg or more at the tissue level. Another concentration that may be used is one that provides to a subject about 30 ng/ml or ng/mg or more at the tissue level. Another concentration that may be used is one that provides to a subject about 50 ng/ml or ng/mg or more at the tissue level. Another concentration that may be used is one that provides to a subject about 100 ng/ml or ng/mg or more at the tissue level. Another concentration that may be used is one that provides to a subject about 200 ng/ml or ng/mg or more at the tissue level. Another concentration that may be used is one that provides to a subject about 300 ng/ml or ng/mg or more at the tissue level. Another concentration that may be used is one that provides to a subject about 400 ng/ml or ng/mg or more at the tissue level. Another concentration that may be used is one that provides to a subject about 500 ng/ml or ng/mg or more at the tissue level. Another concentration that may be used is one that provides to a subject about 1 µg/ml or µg/mg or more at the tissue level. Another concentration that may be used is one that provides to a subject about 1.5 µg/ml or µg/mg or more at the tissue level. Another concentration that may be used is one that provides to a subject about 2 µg/ml or µg/mg or more at the tissue level. Another concentration that may be used is one that provides to a subject about 5 µg/ml or more at the tissue level. In some variations, the tissue is the vitreous. In some variations, the tissue is the retina choroid. In some variations, the tissue is the sclera. One of ordinary skill in the art would know how to arrive at an appropriate concentration depending on the route and duration of administration utilized, given the teachings herein.

Generally, the amount of rapamycin administered in a liquid formulation is an amount sufficient to treat, prevent, inhibit, delay the onset, or cause regression of the disease or condition of the eye for the required amount of time. In some variations the amount of rapamycin administered in the liquid formulation is an amount sufficient to treat the disease or condition of the eye for the required or specified amount of time.

In some variations, a total amount of rapamycin less than about 5 mg is administered subconjunctivally. In some variations, a total amount of rapamycin less than about 5.0 mg is administered subconjunctivally. In some variations, a total amount of rapamycin less than about 4.5 mg is administered subconjunctivally. In some variations, a total amount of rapamycin less than about 4.0 mg is administered subconjunctivally. In some variations, a total amount of rapamycin less than about 3.5 mg is administered subconjunctivally. In some variations, a total amount of rapamycin less than about 3.0 mg is administered subconjunctivally. In some variations, a total amount of rapamycin less than about 2.5 mg is administered subconjunctivally. In some variations, a total amount of rapamycin less than about 2 mg is administered subconjunctivally. In some variations, a total amount of rapamycin less than about 1.2 mg is administered subconjunctivally. In some variations, a total amount of rapamycin less than about 1.0 mg is administered subconjunctivally. In some variations, a total amount of rapamycin less than about 0.8 mg is administered subconjunctivally. In some variations, a total amount of rapamycin less than about 0.6 mg is administered subconjunctivally. In some variations, a total amount of rapamycin less than about 0.4 mg is administered subconjunctivally. In some variations, a volume of a formulation is administered that contains an amount of rapamycin described herein.

In some variations, a total amount of rapamycin less than about 200 µg is administered intravitreally. In some variations, a total amount of rapamycin less than about 200 µg is administered intravitreally. In some variations, a total amount of rapamycin less than about 300 µg is administered intravitreally. In some variations, a total amount of rapamycin less than about 400 µg is administered intravitreally. In some variations, a total amount of rapamycin less than about 500 µg is administered intravitreally. In some variations, a total amount of rapamycin less than about 600 µg is administered intravitreally. In some variations, a total amount of rapamycin less than about 800 µg is administered intravitreally. In some variations, a total amount of rapamycin less than about 1 mg is administered intravitreally. In some variations, a total amount of rapamycin less than about 2 mg is administered intravitreally. In some variations, a total amount of rapamycin less than about 2.5 mg is administered intravitreally. In some variations, a total amount of rapamycin less than about 3 mg is administered intravitreally. In some variations, a total amount of rapamycin less than about 3.5 mg is administered intravitreally. In some variations, a total amount of rapamycin less than about 4 mg is administered intravitreally. In some variations, a volume of a formulation is administered that contains an amount of rapamycin described herein.

In some variations a stable formulation as described herein containing an amount of rapamycin of between about 1 µg and about 5 mg is administered to a human subject for treatment of wet AMD. In some variations a stable formulation as described herein containing an amount of rapamycin of between about 20 µg and about 4 mg is administered to a human subject for treatment of wet AMD. In some variations a liquid formulation as described herein containing an amount of rapamycin of between about 20 µg and about 1.2 mg is administered to a human subject for treatment of wet AMD. In some variations an amount of rapamycin of between about 10 µg and about 0.5 mg is administered to a human subject for treatment of wet AMD. In some variations an amount of rapamycin of between about 10 µg and 90 µg is administered to a human subject for treatment of wet AMD. In some variations an amount of rapamycin of between about 60 µg and about 120 µg is administered to a human subject for treatment of wet AMD. In some variations an amount of rapamycin of between about 100 µg and about 400 µg is administered to a human subject for treatment of wet AMD. In some variations an amount of rapamycin of between about 400 µg and about 1 mg is administered to a human subject for treatment of wet AMD. In some variations an amount of rapamycin of between about 1 mg and about 5 mg is administered to a human subject for treatment of wet AMD. In some variations, an amount of rapamycin of between about 3 mg and about 7 mg is administered to a human subject for treatment of wet AMD. In some variations, an amount of rapamycin of between about 5 mg and about 10 mg is administered to a human subject for treatment of wet AMD.

In some variations a stable formulation as described herein containing an amount of rapamycin of between about 1 µg and about 5 mg is administered to a human subject for prevention of wet AMD. In some variations a stable formulation as described herein containing an amount of rapamycin of between about 20 µg and about 4 mg is administered to a human subject for prevention of wet AMD. In some variations a liquid formulation as described herein containing an amount of rapamycin of between about 20 µg and about 1.2 mg is administered to a human subject for prevention of wet AMD. In some variations an amount of rapamycin of between about 10 µg and about 0.5 mg is administered to a human subject for prevention of wet AMD. In some variations an amount of rapamycin of between about 10 µg and 90 µg is administered to a human subject for prevention of wet AMD. In some variations an amount of rapamycin of between about 60 µg and about 120 µg is administered to a human subject for prevention of wet AMD. In some variations an amount of rapamycin of between about 100 µg and about 400 µg is administered to a human subject for prevention of wet AMD. In some variations an amount of rapamycin of between about 400 µg and about 1 mg is administered to a human subject for prevention of wet AMD. In some variations an amount of rapamycin of between about 1 mg and about 5 mg is administered to a human subject for prevention of wet AMD. In some variations, an amount of rapamycin of between about 3 mg and about 7 mg is administered to a human subject for prevention of wet AMD. In some variations, an amount of rapamycin of between about 5 mg and about 10 mg is administered to a human subject for prevention of wet AMD.

In some variations a stable formulation as described herein containing an amount of rapamycin of between about 1 µg and about 5 mg is administered to a human subject for treatment of dry AMD. In some variations a stable formulation as described herein containing an amount of rapamycin of between about 20 µg and about 4 mg is administered to a human subject for treatment of dry AMD. In some variations a liquid formulation as described herein containing an amount of rapamycin of between about 20 µg and about 1.2 mg is administered to a human subject for treatment of dry AMD. In some variations an amount of rapamycin of between about 10 µg and about 0.5 mg is administered to a human subject for treatment of dry AMD. In some variations an amount of rapamycin of between about 10 µg and 90 µg is administered to a human subject for treatment of dry AMD. In some variations an amount of rapamycin of between about 60 µg and about 120 µg is administered to a human subject for treatment of dry AMD. In some variations an amount of rapamycin of between about 100 µg and about 400 µg is administered to a human subject for treatment of dry AMD. In some variations an amount of rapamycin of between about 400 µg and about 1 mg is administered to a human subject for treatment of dry AMD. In some variations an amount of rapamycin of between about 1 mg and about 5 mg is administered to a human subject for treatment of dry AMD. In some variations, an amount of rapamycin of between about 3 mg and about 7 mg is administered to a human subject for treatment of dry AMD. In some variations, an amount of rapamycin of between about 5 mg and about 10 mg is administered to a human subject for treatment of dry AMD.

In some variations, a liquid formulation as described herein containing an amount of rapamycin of between about 1 µg and about 5 mg is administered to a human subject for treatment of angiogenesis, including but not limited to choroidal neovascularization. In some variations, an amount of rapamycin of between about 20 µg and about 4 mg is administered to the human subject; between about 20 µg and about 1.2 mg; between about 10 µg and about 0.5 mg is administered to a human subject for treatment of wet AMD, between about 10 µg and 90 µg, between about 60 µg and 120 µg is administered to the human subject; between about 100 µg and 400 µg, between about 400 µg and 1 mg is administered to the human subject; in some variations, an amount of rapamycin of between about 1 mg and 5 mg is administered to the human subject; in some variations, an amount of rapamycin of between about 3 mg and 7 mg is administered to the human subject; in some variations, an amount of rapamycin of between about 5 mg and 10 mg is administered to the human subject for treatment of angiogenesis, including but not limited to choroidal neovascularization.

In some variations, a liquid formulation as described herein contains an amount of a therapeutic agent equivalent to an amount of rapamycin. In some variations, a liquid formulation as described herein containing an amount of a therapeutic agent equivalent to an amount of rapamycin of between about 1 µg and about 5 mg is administered to a human subject for treatment of wet AMD. In some variations, an amount of a therapeutic agent equivalent to an amount of rapamycin of between about 1 µg and about 5 mg is administered to the human subject; between about 20 µg and about 1.2 mg; between about 10 µg and about 0.5 mg is administered to a human subject for treatment of wet AMD, between about 10 µg and 90 µg, between about 60 µg and 120 µg is administered to the human subject; between about 100 µg and 400 µg, between about 400 µg and 1 mg is administered to the human subject; in some variations, an amount of a therapeutic agent equivalent to an amount of rapamycin of between about 1 mg and 5 mg is administered to the human subject; in some variations, an amount of a therapeutic agent equivalent to an amount of rapamycin of between about 3 mg and 7 mg is administered to the human subject; in some variations, an amount of a therapeutic agent equivalent to an amount of rapamycin of between about 5 mg and 10 mg is administered to the human subject.

In some variations, a liquid formulation as described herein containing an amount of a therapeutic agent equivalent to an amount of rapamycin of between about 1 µg and about 5 mg is administered to a human subject for treatment of dry AMD. In some variations, an amount of a therapeutic agent equivalent to an amount of rapamycin of between about 20 µg and about 4 mg is administered to the human subject; between about 20 µg and about 1.2 mg; between about 10 µg and about 0.5 mg is administered to a human subject for treatment of wet AMD, between about 10 µg and 90 µg, between about 60 µg and 120 µg is administered to the human subject; between about 100 µg and 400 µg, between about 400 µg and 1 mg is administered to the human subject; in some variations, an amount of a therapeutic agent equivalent to an amount of rapamycin of between about 400 µg and 1 mg is administered to the human subject; in some variations, an amount of a therapeutic agent equivalent to an amount of rapamycin of between about 1 mg and 5 mg is administered to the human subject; in some variations, an amount of a therapeutic agent equivalent to an amount of rapamycin of between about 3 mg and 7 mg is administered to the human subject; in some variations, an amount of a therapeutic agent equivalent to an amount of rapamycin of between about 5 mg and 10 mg is administered to the human subject to treat dry AMD.

In some variations, a liquid formulation as described herein containing an amount of a therapeutic agent equivalent to an amount of rapamycin of between about 1 µg and about 5 mg is administered to a human subject for prevention of wet AMD. In some variations, an amount of a therapeutic agent equivalent to an amount of rapamycin of between about 20 µg and about 4 mg is administered to the human subject; between about 20 µg and about 1.2 mg; between about 10 µg and about 0.5 mg is administered to a human subject for prevention of wet AMD, between about 10 µg and 90 µg, between about 60 µg and 120 µg is administered to the human subject; between about 100 µg and 400 µg, between about 400 µg and 1 mg is administered to the human subject; in some variations, an amount of a therapeutic agent equivalent to an amount of rapamycin of between about 400 µg and 1 mg is administered to the human subject; in some variations, an amount of a therapeutic agent equivalent to an amount of rapamycin of between about 1 mg and 5 mg is administered to the human subject; in some variations, an amount of a therapeutic agent equivalent to an amount of rapamycin of between about 3 mg and 7 mg is administered to the human subject; in some variations, an amount of a therapeutic agent equivalent to an amount of rapamycin of between about 5 mg and 10 mg is administered to the human subject to prevent wet AMD.

In some variations, a liquid formulation as described herein containing an amount of a therapeutic agent equivalent to an amount of rapamycin of between about 20 µg and about 10 mg is administered to a human subject for treatment of angiogenesis, including but not limited to choroidal neovascularization. In some variations, an amount of a therapeutic agent equivalent to an amount of rapamycin of between about 30 µg and about 9 mg is administered to the human subject; in some variations, an amount of a therapeutic agent equivalent to an amount of rapamycin of between about 10 µg and 90 µg is administered to the human subject; in some variations, an amount of a therapeutic agent equivalent to an amount of rapamycin of between about 60 µg and 120 µg is administered to the human subject; in some variations, an amount of a therapeutic agent equivalent to an amount of rapamycin of between about 100 µg and 400 µg is administered to the human subject; in some variations, an amount of a therapeutic agent equivalent to an amount of rapamycin of between about 400 µg and 1 mg is administered to the human subject; in some variations, an amount of a therapeutic agent equivalent to an amount of rapamycin of between about 1 mg and 5 mg is administered to the human subject; in some variations, an amount of a therapeutic agent equivalent to an amount of rapamycin of between about 3 mg and 7 mg is administered to the human subject; in some variations, an amount of a therapeutic agent equivalent to an amount of rapamycin of between about 5 mg and 10 mg is administered to the human subject.

In some variations, any one or more of the formulations described herein are administered intravitreally every 3 or more months, every 6 or more months, every 9 or more months, or every 12 or more months, or longer, to treat one or more of choroidal neovascularization, wet AMD, dry AMD, or to prevent wet AMD. In some variations, any one or more of the formulations described herein are administered subconjunctivally every 3 or more months, every 6 or more months, every 9 or more months, or every 12 or more months, or longer, to treat one or more of choroidal neovascularization, wet AMD, dry AMD, or to prevent wet AMD.

In some variations, any one or more of the rapamycin formulations described herein are administered intravitreally every 3 or more months, every 6 or more months, every 9 or more months, or every 12 or more months, or longer, to treat one or more of choroidal neovascularization, wet AMD, dry AMD, or to prevent wet AMD. In some variations, any one or more of the rapamycin formulations described herein are administered subconjunctivally every 3 or more months, every 6 or more months, every 9 or more months, or every 12 or more months, or longer, to treat one or more of choroidal neovascularization, wet AMD, dry AMD, or to prevent wet AMD. In some variations, the effect of the rapamycin persists beyond the period during which it is measurable in the ocular tissues by LCMS.

Delivery of the therapeutic agents described herein may, for example, be delivered at a dosage range between about 1 ng/day and about 100 µg/day, or at dosages higher, or lower than this range, depending on the route and duration of administration. In some variations of liquid formulation or formulation used in the methods described herein, the therapeutic agents are delivered at a dosage range of between about 0.1 µg/day and about 10 µg/day. In some variations of stable formulation used in the methods described herein, the therapeutic agents are delivered at a dosage range of between about 1 µg/day and about 5 µg/day. Dosages of various therapeutic agents for treatment, prevention, inhibition, delay of onset, or cause of regression of various diseases and conditions described herein can be refined by the use of clinical trials.

When a therapeutically effective amount of rapamycin is administered to a subject suffering from wet AMD, the rapamycin may treat, inhibit, or cause regression of the wet AMD. Different therapeutically effective amounts may be required for treatment, inhibition or causing regression. A subject suffering from wet AMD may have CNV lesions, and without being bound by theory it is believed that administration of a therapeutically effective amount of rapamycin may have a variety of effects, including but not limited to causing regression of the CNV lesions, stabilizing the CNV lesion, and preventing progression of an active CNV lesion.

When a therapeutically effective amount of rapamycin is administered to a subject suffering from dry AMD, it is believed that the rapamycin may prevent or slow the progression of dry AMD to wet AMD.

EXAMPLES

Where ethanol is used, it is 200 proof ethanol from Gold Shield Distributors, Hayward, Calif. Where rapamycin is used, it is from LC laboratories, Woburn, Mass., or Chunghwa Chemical Synthesis & Biotech Co., LTD (CCSB), Taipei Hsien, Taiwan, ROC. Where PEG 400 is used, it is from The Dow Chemical Company, New Milford, Conn.

Example 1

Preparation of a Rapamycin-Containing Solution by Sonication

Rapamycin was dissolved in 100% ethanol by sonication. Excess ethanol was driven off by forced evaporation. PEG 400 was sonicated. The rapamycin-ethanol solution was added to the PEG 400, and the mixture was sonicated until a solution was formed. Sonication was performed such that the temperature of the mixture did not exceed 40° C. for an extended period of time. Final concentrations as a percentage of the final formulation weight were approximately: rapamycin 2% w/w, ethanol 4% w/w, and PEG 400 94% w/w. The solution was sterilized by filtration through a 0.2 micron filter.

Clear glass 2 ml vials were filled with 2 ml of the filtered solution to leave a head space in each container of up to about 400 μl. Amber glass 2 ml vials were filled with 0.5 ml of the filtered solution to leave a head space in each container of up to about 1900 μl.

Results are shown in Table 1. Analysis was performed for each vial configuration for which there is a number in Table 1. Generally there were 2-3 replicates of each vial configuration. Generally 3 samples of each vial configuration replicate were analyzed via standard HPLC.

When 0.5 ml of the formulation were placed in a 2 ml amber glass vial, after one month at 25 degrees Celsius the formulation had a reduced level of rapamycin of about 29% relative the starting amount of rapamycin in the formulation. When 0.5 ml of the formulation were placed in a 2 ml amber glass vial, after one, two, three and six months at 5 degrees Celsius the formulation had a reduced level of rapamycin of about 5.2%, 14%, 22.3%, and 26.7% relative the starting amount of rapamycin in the formulation. When 0.5 ml of the formulation were placed in a 2 ml amber glass vial, after one, two, three and six months at −20 degrees Celsius the formulation had a reduced level of rapamycin of about 1.2%, 5.1%, 8.8%, and 21.5% relative the starting amount of rapamycin in the formulation. Without being bound by theory, it is thought that this reduced level of therapeutic agent was caused in part by a large head space relative to the volume of the formulation, as well as the components of the amber glass. Amber glass has components such as metals that are known to oxidize formulations sensitive to oxidation.

When 2 ml of the formulation was placed in a 2 ml clear glass vial, after one, two, and three months at 25 degrees Celsius the formulation had a reduced level of rapamycin of about 3%, 4%, and 9% respectively relative the starting amount of rapamycin in the formulation.

There is a standardized conversion known by those of skill in the art, by which stability for a formulation or a therapeutic agent in a formulation stored at elevated temperatures is indicative of the stability of a formulation or a therapeutic agent in a formulation stored at a lower temperatures. This conversion is based on the ICH Harmonized Tripartite Guideline "Stability Testing of New Drug Substances and Products Q1A(R2). According to this Guideline, storage at 25° C. for a period of time is indicative of stability of the formulation or therapeutic agent for twice this period of time at 5° C. See also Drug Stability, Principles and Practices, Third Edition, Jens T. Cartensen, Chris T. Rhodes, published by Marcel Dekker. Assuming an Arrhenius dependence for the degradation kinetics, an increase of 10° C. accelerates the effective period of storage by approximately a factor of 2. Hency, the ICH guidelines estimate that 6 months at 40° C. is equivalent to 2 years at room temperature. This conversion therefore allows that 6 month storage at 25° C. and 60% relative humidity is similar to a 2 year shelf-life for a formulation at 5° C.

The oxygen and nitrogen levels in a formulation may be measured by any method known by those of skill in the art. As one nonlimiting example, the percent oxygen in the head space or dissolved gases of a formulation may be measured by the method described in Example 10. As one nonlimiting example, the percent nitrogen in the head space or dissolved gases of a formulation may be estimated by subtracting from 100 the percent oxygen measured by the method described in Example 10.

Described herein are liquid formulations of rapamycin, including without limitation a formulation of about 2% w/w rapamycin, about 4% w/w ethanol, and 94% w/w PEG 400, wherein the formulation has a level of dissolved oxygen less than or approximately equal to the level of dissolved oxygen in a formulation as prepared by the method described in Example 1, measured by the fluorimetric method described in Example 10. Described herein are liquid formulations of rapamycin, including without limitation a formulation of about 2% w/w rapamycin, about 4% w/w ethanol, and 94% w/w PEG 400, wherein the formulation has a level of dissolved nitrogen approximately equal to the level of dissolved nitrogen in a formulation as prepared by the method described in Example 1, measured by the flourimetric method described in Example 1.

Example 2

Preparation of a Rapamycin-Containing Solution by Roto Evaporation

In some of the samples, BHT (butylated hydroxytoluene) was added to the ethanol prior to preparing the stock solutions of sirolimus (rapamycin). Rapamycin was added to 100% ethanol, which ethanol either had or did not have BHT. The mixture was sonicated for a period of time sufficient to reduce the dissolved oxygen, and until all of the rapamycin had gone into solution to form a rapamycin stock solution. A diluent solvent was prepared by sonicating PEG 400 for a period of time sufficient to decrease the dissolved oxygen.

The rapamycin stock solution and the diluent solvent (PEG 400) were then rotated at about room temperature in a rotary evaporator for a period of time sufficient to mix the stock solution with the diluent solvent. A portion of ethanol was evaporated from the solution by increasing the solution temperature, maintaining a temperature that did not exceed 40° C. for an extended period of time, and continuing to rotate the solution.

The resulting solution comprised about 2% rapamycin w/w, about 4% ethanol w/w, and about 94% PEG 400 w/w.

The solution was then filtered through a 0.2 micron filter. Clear 2 ml glass vials were filled with either 2 ml or 0.5 ml of the filtered solution to leave a head space in each container of about 400 or 1900 μl, respectively. The vial was then stoppered using, for example, Teflon, and crimped using aluminum seals.

Rapamycin stability was measured according to the method described in Example 1. Analysis was performed for each vial configuration for which there is a number in Table 1. Results are shown in Table 1.

When 2 ml of the formulation without BHT was placed in a 2 ml clear glass vial, after one, two, and three months at 25 degrees Celsius the formulation had a reduced level of rapamycin of about 7.0%, 6.8%, and 9.6% respectively relative to the starting amount of rapamycin in the formulation. When 2 ml of the formulation was placed in a 2 ml clear glass vial, after one, two, three, and six months at 5 degrees Celsius the formulation had a reduced level of rapamycin of about 4.9%, 5.4%, 7.7%, and 9.3% respectively relative to the starting amount of rapamycin in the formulation. When 2 ml of the formulation was placed in a 2 ml clear glass vial, after one, two, three, and six months at −20 degrees Celsius the formulation had a reduced level of rapamycin of about 0.6%, 0.2%, 1.7%, and 1.7% respectively relative to the starting amount of rapamycin in the formulation.

When 2 ml of the formulation with BHT was placed in a 2 ml clear glass vial, after one, two, and three months at 25 degrees Celsius the formulation had a reduced level of rapamycin of about 4.2%, 6.0%, and 10.8% respectively relative to the starting amount of rapamycin in the formulation. When 2 ml of the formulation with BHT was placed in a 2 ml clear glass vial, after one, two, three, and six months at 5 degrees Celsius the formulation had a reduced level of rapamycin of about 2.3%, 1.5%, 4.4%, and 5.2% respectively relative to the starting amount of rapamycin in the formulation. When 2 ml of the formulation with BHT was placed in a 2 ml clear glass vial, after one, two, three, and six months at −20 degrees Celsius the formulation had a reduced level of rapamycin of about 0.9%, 0.7%, 3.1%, and 2.4% respectively relative to the starting amount of rapamycin in the formulation. Without being bound by theory, it is generally that at this vial configuration the effect of the BHT is likely to result in an increased stability of the formulation relative to a formulation without BHT at certain temperatures, though this effect may not be seen at all temperatures. Without being bound by theory, it is thought that at this vial configuration with a 2 ml fill volume has a increased stability of rapamycin relative to a 0.5 ml fill volume due to the reduced head space, which results in a lower degree of exposure of the formulation to components of the air than a 0.5 ml fill volume in a 2 ml vial.

When 0.5 ml of the formulation with BHT was placed in a 2 ml clear glass vial, after one, two, and three months at 25 degrees Celsius the formulation had a reduced level of rapamycin of about 5.2%, 5.8%, and 10.8% respectively relative to the starting amount of rapamycin in the formulation. When 0.5 ml of the formulation with BHT was placed in a 2 ml clear glass vial, after one, two, three, and six months at 5 degrees Celsius the formulation had a reduced level of rapamycin of about 3.3%, 2.0%, 4.1%, and 6.0% respectively relative to the starting amount of rapamycin in the formulation. When 0.5 ml of the formulation with BHT was placed in a 2 ml clear glass vial, after one, two, three, and six months at −20 degrees Celsius the formulation had a reduced level of rapamycin of about 1.5%, 1.4%, 3.0%, and 2.2% respectively relative to the starting amount of rapamycin in the formulation. Without being bound by theory, it is thought that at this vial configuration storage at −20 degrees Celsius results in greater stability of rapamycin than storage at 5 degrees Celsius, and storage at either of −20 or 5 degrees Celsius results in greater stability of rapamycin than storage at 25 degrees Celsius. Without being bound by theory, it is generally that at this vial configuration the effect of the BHT is likely to result in an increased stability of the formulation relative to a formulation without BHT. Without being bound by theory, it is thought that at this vial configuration with a 0.5 ml fill volume has a reduced stability of rapamycin due to the greater head space, which results in a higher degree of exposure of the formulation to components of the air than a 2 ml fill volume in a 2 ml vial.

The oxygen and nitrogen levels in these formulations may be measured by the method described in either one or more of Example 1 or Example 10.

Described herein are liquid formulations of rapamycin, including without limitation a formulation of about 2% w/w rapamycin, about 4% w/w ethanol, and 94% w/w PEG 400, wherein the formulation has a level of dissolved oxygen less than or approximately equal to the level of dissolved oxygen in a formulation as prepared by the method described in Example 2, measured by the fluorimetric method described in Example 10. Described herein are liquid formulations of rapamycin, including without limitation a formulation of about 2% w/w rapamycin, about 4% w/w ethanol, and 94% w/w PEG 400, wherein the formulation has a level of dissolved nitrogen approximately equal to the level of dissolved nitrogen in a formulation as prepared by the method described in Example 2, measured by the flourimetric method described in Example 1.

Example 3

Preparation of a Rapamycin-Containing Solution by Sonication, Rotovap, and Nitrogen Sparging In one example of the preparation and packaging of a liquid formulation, about 320 g of 100% ethanol was sparged with medical grade compressed nitrogen for about 10 minutes. In some of the samples, BHT (butylated hydroxytoluene) was added to the ethanol prior to preparing the stock solutions of rapamycin. 40 g of rapamycin was added to the ethanol which either had or did not have BHT. The mixture was sonicated for about 20 minutes, by the end of which all of the rapamycin had gone into solution to form a sirolimus stock solution. A diluent solvent was prepared by sonicating about 1880 g of PEG 400 for about 60 minutes, and then sparging the solvent with nitrogen for about 10 minutes.

The rapamycin stock solution and the diluent solvent (PEG 400) were then rotated at about room temperature in a rotary evaporator for about 10 minutes to mix the stock solution with the diluent solvent. After mixing, the solution was sparged with medical grade compressed nitrogen for about 10 minutes. After sparging, about 240 g of excess ethanol was evaporated from the solution by increasing the solution temperature, maintaining a temperature that did not exceed 40° C. for an extended period of time, and continuing to rotate the solution for about 2.5 hours.

The resulting solution comprised about 2% by final of rapamycin, about 4% by final weight of ethanol, and about 94% by final weight of PEG 400. This solution was sparged with nitrogen for about 10 minutes. The solution was then filtered through a 0.2 micron filter.

Regular clear glass 2 ml vials were filled with 2 ml each of the filtered solution to leave a head space in each container of about 400 µl. Clear glass 2 ml vials were filled with 0.5 ml or 2 ml each of the filtered solution to leave a head space in each container of about 1900 and 400 µl, respectively. The vials were then stoppered with Teflon and crimped using aluminum seals.

Rapamycin stability was measured according to the method described in Example 1. Analysis was performed for each vial configuration for which there is a number in Table 1. Results are shown in Table 1.

When 2 ml of the formulation with BHT was placed in a 2 ml clear glass vial, after one, two, and three months at 25 degrees Celsius the formulation had a reduced level of rapamycin of about 0.29%, 4.8%, and 8.7% respectively relative to the starting amount of rapamycin in the formulation. When 2 ml of the formulation with BHT was placed in a 2 ml clear glass vial, after one, two, three and six months at 5 degrees Celsius the formulation had a reduced level of rapamycin of about 0%, 0%, 1.7%, and 2.5%, respectively relative to the starting amount of rapamycin in the formulation. When 2 ml of the formulation with BHT was placed in a 2 ml clear glass vial, after one, two, three and six months at −20 degrees Celsius the formulation had a reduced level of rapamycin of about 0%, 0%, 2.2% and 1.4%, respectively relative to the starting amount of rapamycin in the formulation. Without being bound by theory, it is generally that at this vial configuration the effect of the BHT is likely to result in an increased stability of the formulation relative to a formulation without BHT at certain temperatures, though this effect may not be seen at all temperatures. Without being bound by theory, it is thought that at this vial configuration with a 2 ml fill volume has a increased stability of rapamycin relative to a 0.5 ml fill volume due to the reduced head space, which results in a lower degree of exposure of the formulation to components of the air than a 0.5 ml fill volume in a 2 ml vial.

When 0.5 ml of the formulation with BHT was placed in a 2 ml clear glass vial, after one, two, and three months at 25 degrees Celsius the formulation had a reduced level of rapamycin of about 0%, 4.7%, and 9.5% respectively relative to the starting amount of rapamycin in the formulation. When 0.5 ml of the formulation with BHT was placed in a 2 ml clear glass vial, after one, two, three and six months at 5 degrees Celsius the formulation had a reduced level of rapamycin of about 0%, 0%, 2.4% and 2.5 respectively relative to the starting amount of rapamycin in the formulation. When 0.5 ml of the formulation with BHT was placed in a 2 ml clear glass vial, after one, two, three and six months at −20 degrees Celsius the formulation had a reduced level of rapamycin of about 0%, 0.6%, 1.3% and 1.4% respectively relative to the starting amount of rapamycin in the formulation. Without being bound by theory, it is generally that at this vial configuration the effect of the BHT is likely to result in an increased stability of the formulation relative to a formulation without BHT. Without being bound by theory, it is thought that at this vial configuration with a 0.5 ml fill volume has a reduced stability of rapamycin due to the greater head space, which results in a higher degree of exposure of the formulation to components of the air than a 2 ml fill volume in a 2 ml vial.

When 2 ml of the formulation without BHT was placed in a 2 ml clear glass vial, after one, two, and three months at 25 degrees Celsius the formulation had a reduced level of rapamycin of about 6.3%, 5.5%, and 9.9% respectively relative to the starting amount of rapamycin in the formulation. When 2 ml of the formulation without BHT was placed in a 2 ml clear glass vial, after one, two, three and six months at 5 degrees Celsius the formulation had a reduced level of rapamycin of about 1.1%, 1.3%, 7.0%, and 6.9% respectively relative to the starting amount of rapamycin in the formulation. When 2 ml of the formulation without BHT was placed in a 2 ml clear glass vial, after one, two, three and six months at −20 degrees Celsius the formulation had a reduced level of rapamycin of about 0.2%, 0%, 1.8% and 0.9% respectively relative to the starting amount of rapamycin in the formulation. Without being bound by theory, it is thought that at this vial configuration the omission of the BHT is likely to result in an increased stability of the formulation relative to a formulation with BHT. Without being bound by theory, it is thought that this vial configuration with a 2 ml fill volume has an increased stability of rapamycin due to the lesser head space, which results in a lower degree of exposure of the formulation to components of the air than a 0.5 ml fill volume in a 2 ml vial.

The oxygen and nitrogen levels in these formulations may be measured by the method described in either one or more of Example 1 or Example 10.

Described herein are liquid formulations of rapamycin, including without limitation a formulation of about 2% w/w rapamycin, about 4% w/w ethanol, and 94% w/w PEG 400, wherein the formulation has a level of dissolved oxygen less than or approximately equal to the level of dissolved oxygen in a formulation as prepared by the method described in Example 3, measured by the fluorimetric method described in Example 10. Described herein are liquid formulations of rapamycin, including without limitation a formulation of about 2% w/w rapamycin, about 4% w/w ethanol, and 94% w/w PEG 400, wherein the formulation has a level of dissolved nitrogen approximately equal to the level of dissolved nitrogen in a formulation as prepared by the method described in Example 3, measured by the flourimetric method described in Example 1.

Example 4

Preparation of a Rapamycin-Containing Solution by Sonication, Rotovap, Nitrogen Sparging, and Nitrogen Blanketing The method described in Example 3 was performed, but with the additional steps of blanketing the rapamycin solution with medical grade compressed nitrogen for about five minutes after each of (a) the rotary evaporation step to drive off ethanol, (b) filtering the solution, and (c) filling the vial. In these experiments, there was no BHT added to the samples. All vials were 2 ml clear glass, and were filed with either 0.5 ml or 2.0 ml of the formulation.

Three replicates of this experiment were performed of this experiment with the 2 ml fill volume, and two replicates were performed at the 0.5 ml fill volume. Rapamycin stability was measured according to the method described in Example 1. Analysis was performed for each vial configuration for which there is a number in Table 1. Results are shown in Table 1. For the first and third replicates shown, relative humidity was measured at 60%.

When 0.5 ml of the formulation without BHT was placed in a 2 ml clear glass vial, the replicates show overall consistency in the following observations. Without being bound by theory, it is thought that at this vial configuration with a 0.5 ml fill volume has a reduced stability of rapamycin than a 2 ml fill volume due to the greater head space, which results in a higher degree of exposure of the formulation to components of the air than a 2 ml fill volume in a 2 ml vial. Without being bound by theory, it is thought that at this vial configuration with a 0.5 ml fill volume has improved stability relative to a formulation as in Example 1 without BHT that was stored in amber glass.

When 2 ml of the formulation without BHT was placed in a 2 ml clear glass vial, the replicates show overall consistency in the following observations. At least at the later timepoint, this vial configuration with a 2 ml fill volume has improved stability relative to a formulation as in Example 1 without BHT that was stored in amber glass. At the majority of the timepoints this vial configuration with a 2 ml fill volume has improved stability relative to a formulation as in Example 2 without BHT that was stored in clear glass. At the majority of timepoints, this vial configuration with a 2 ml fill volume has improved stability relative to a formulation as in Example 3 without BHT that was stored in clear glass.

Figure 2:
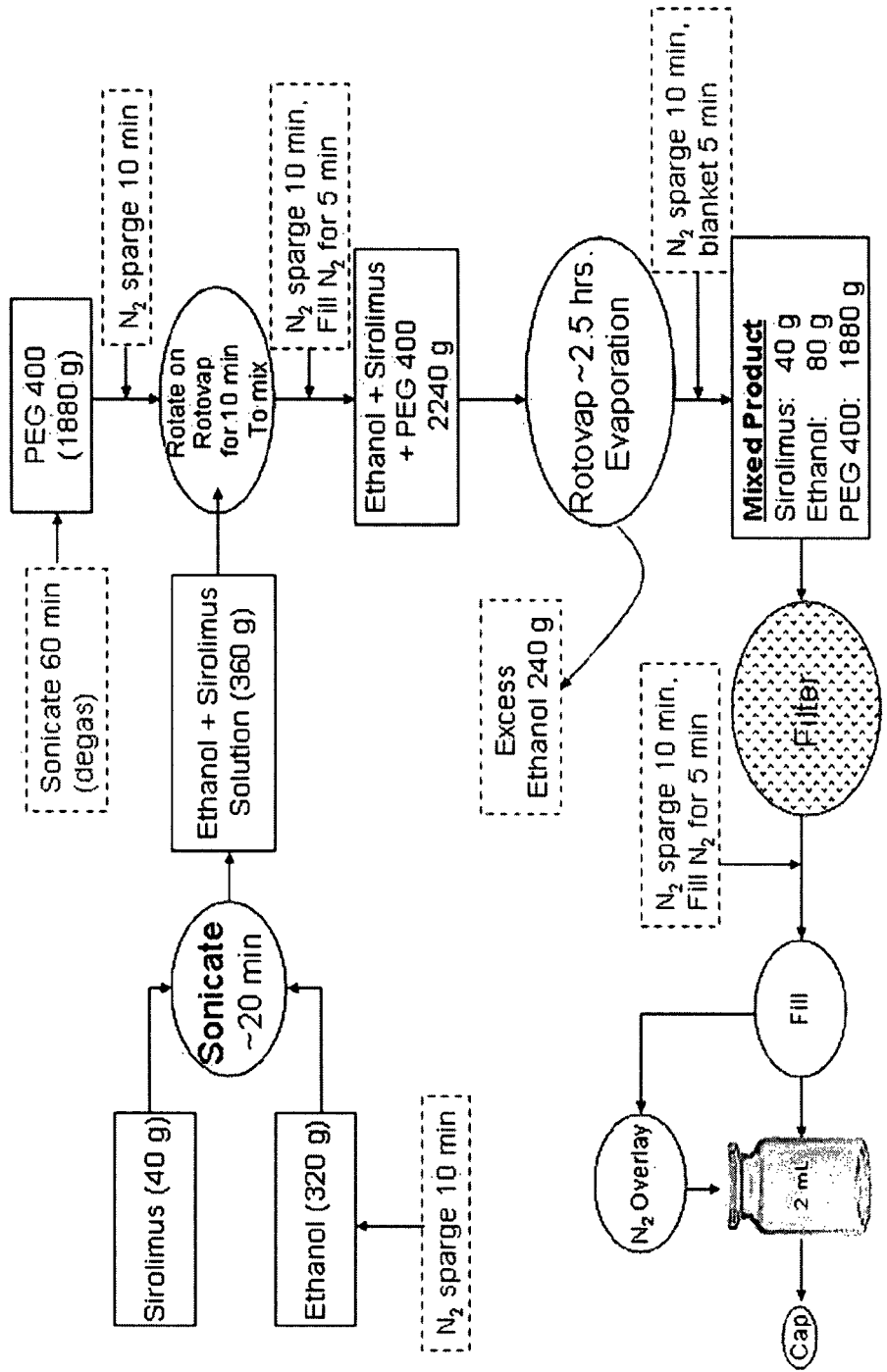
FIG. 2 depicts one variation for preparing the formulations described herein.

FIG. 2 depicts this process for preparing a stable formulation.

The oxygen and nitrogen levels in these formulations may be measured by the method described in either one or more of Example 1 or Example 10.

Described herein are liquid formulations of rapamycin, including without limitation a formulation of about 2% w/w rapamycin, about 4% w/w ethanol, and 94% w/w PEG 400, wherein the formulation has a level of dissolved oxygen less than or approximately equal to the level of dissolved oxygen in a formulation as prepared by the method described in Example 4, measured by the fluorimetric method described in Example 10. Described herein are liquid formulations of rapamycin, including without limitation a formulation of about 2% w/w rapamycin, about 4% w/w ethanol, and 94% w/w PEG 400, wherein the formulation has a level of dissolved nitrogen approximately equal to the level of dissolved nitrogen in a formulation as prepared by the method described in Example 4, measured by the flourimetric method described in Example 1.

Example 5

Any one or more of the liquid formulations recited in Table 2 may be prepared by sonication. Generally, to prepare a stable formulation comprising a therapeutic agent that is sensitive to one or more components of the air, including but not limited to oxygen, one or more of the components of the formulation is treated to reduce the oxygen content. The one or more components of the liquid formulation are sonicated for a period of time sufficient to degas the one or more components. The one or more components are sonicated either before or after their combination with other components of the liquid formulation. The sonication is performed under conditions that retain stability of the therapeutic agent relative to the therapeutic agent prior to sonication. Where one or more of the components of the liquid formulation is sensitive to temperature, sonication is performed under such conditions that the stability of the one or more temperature-sensitive components is retained. Where the therapeutic agent is rapamycin, the temperature is preferably not over 40 degrees Celsius for an extended period of time. Where one or more of the components of the liquid formulation is sensitive to light, sonication is performed under such conditions that the stability of the one or more temperature-sensitive components is retained.

This method is performed either alone or in combination with one or more other methods to produce a stable formulation.

The oxygen and nitrogen levels in these formulations may be measured by the method described in either one or more of Examples 1 or 10.

Described herein are liquid formulations of rapamycin, including without limitation a formulation of about 2% w/w rapamycin, about 4% w/w ethanol, and 94% w/w PEG 400, wherein the formulation has a level of dissolved oxygen less than or approximately equal to the level of dissolved oxygen in a formulation as prepared by the method described in Example 5, measured by the fluorimetric method described in Example 10. Described herein are liquid formulations of rapamycin, including without limitation a formulation of about 2% w/w rapamycin, about 4% w/w ethanol, and 94% w/w PEG 400, wherein the formulation has a level of dissolved nitrogen approximately equal to the level of dissolved nitrogen in a formulation as prepared by the method described in Example 5, measured by the flourimetric method described in either one or more of Examples 1 or 10.

Example 6

Any one or more of the liquid formulations recited in Table 2 are prepared by a process described herein. Generally, to prepare a stable formulation comprising a therapeutic agent that is sensitive to one or more components of the air, including but not limited to oxygen, one or more of the components of the formulation is treated to reduce the oxygen content. The one or more components of the liquid formulation are sparged with an inert gas, such as a noble gas, including but not limited to nitrogen, argon, or helium.

This method is performed either alone or in combination with one or more other methods to produce a stable formulation.

In some examples the therapeutic agent is rapamycin, and the one or more components of the rapamycin formulation are sparged with an inert gas such as nitrogen at various stages of the process described in examples 5-7.

Stability of the therapeutic agent may be measured according to the method described in Example 1.

The oxygen and nitrogen levels in these formulations may be measured by the method described in either one or more of Examples 1 or 10.

Described herein are liquid formulations of rapamycin, including without limitation a formation of about 2% w/w rapamycin, about 4% w/w ethanol, and 94% w/w PEG 400, wherein the formulation has a level of dissolved oxygen less than or approximately equal to the level of dissolved oxygen in a formulation as prepared by the method described in Example 6, measured by the fluorimetric method described in Example 10. Described herein are liquid formulations of rapamycin, including without limitation a formulation of about 2% w/w rapamycin, about 4% w/w ethanol, and 94% w/w PEG 400, wherein the formulation has a level of dissolved nitrogen approximately equal to the level of dissolved nitrogen in a formulation as prepared by the method described in Example 6, measured by the flourimetric method described in Example 1.

Example 7

Any one or more of the liquid formulations recited in Table 2 are prepared by a process described herein. Generally, to prepare a stable formulation comprising a therapeutic agent that is sensitive to one or more components of the air, including but not limited to oxygen, one or more of the components of the formulation is treated to reduce the oxygen content. The one or more components of the liquid formulation are blanketed with an inert gas, such as a noble gas, including but not limited to nitrogen, argon, or helium.

This method may be performed either alone or in combination with one or more other methods to produce a stable formulation.

In some examples the therapeutic agent is rapamycin, and the one or more components of the rapamycin formulation are blanketed with an inert gas such as nitrogen at various stages of the process described in examples 5-7.

Stability of the therapeutic agent is measured according to the method described in Example 1.

The oxygen and nitrogen levels in these formulations may be measured by the method described in either one or more of Examples 1 or 10.

Described herein are liquid formulations of rapamycin, including without limitation a formulation of about 2% w/w rapamycin, about 4% w/w ethanol, and 94% w/w PEG 400, wherein the formulation has a level of dissolved oxygen less than or approximately equal to the level of dissolved oxygen in a formulation as prepared by the method described in Example 7, measured by the fluorimetric method described in Example 10. Described herein are liquid formulations of rapamycin, including without limitation a formulation of about 2% w/w rapamycin, about 4% w/w ethanol, and 94% w/w PEG 400, wherein the formulation has a level of dissolved nitrogen approximately equal to the level of dissolved nitrogen in a formulation as prepared by the method described in Example 7, measured by the flourimetric method described in Example 1.

Example 8

A stable suspension is prepared by any one or more of the methods of producing a stable formulation described in Examples 5-7. Generally, to prepare a stable suspension comprising a therapeutic agent that is sensitive to one or more components of the air, including but not limited to oxygen, one or more of the components of the formulation is treated to reduce the oxygen content. The one or more components of the liquid formulation is treated by one or more of sonication, sparging with an inert gas, or blanketing with an inert gas, wherein the inert gas is a noble gas that is nitrogen, argon, or helium.

The one or more components of the suspension are then filtered through a 0.2 micron filter for sterilization. The suspension either comprises particles of a sufficiently small size to be filtered through the 0.2 micron filter, or comprises particles that are sterilized by other methods known by those of skill in the art. The particles are optionally particles or crystals of pure therapeutic agent that have been sterilized either prior to or subsequently to adding the particles or crystals to other components of the formulation. The particles are optionally treated with gamma irradiation, or e-beam sterilization, which are non-limiting examples of standard methods of sterilizing solids used by those of in the art.

In some examples the therapeutic agent is rapamycin, and the suspension is a nanosuspension. In some examples the therapeutic agent is rapamycin, and rapamycin is present as particles of pure rapamycin that are sterilized either by gamma irradiation or e-beam treatment.

This method may be performed either alone or in combination with one or more other methods to produce a stable formulation.

Stability of the therapeutic agent may be measured according to the method described in Example 1.

The oxygen and nitrogen levels in these formulations may be measured by the method described in either one or more of Examples 1 or 10.

Described herein are liquid formulations of rapamycin, including without limitation a formulation of about 2% w/w rapamycin, about 4% w/w ethanol, and 94% w/w PEG 400, wherein the formulation has a level of dissolved oxygen less than or approximately equal to the level of dissolved oxygen in a formulation as prepared by the method described in Example 8, measured by the fluorimetric method described in Example 10. Described herein are liquid formulations of rapamycin, including without limitation a formulation of about 2% w/w rapamycin, about 4% w/w ethanol, and 94% w/w PEG 400, wherein the formulation has a level of dissolved nitrogen approximately equal to the level of dissolved nitrogen in a formulation as prepared by the method described in Example 8, measured by the flourimetric method described in Example 1.

Example 10

Measurement of Oxygen in Dissolved Gases

By way of overview, the fiber optic oxygen sensor was a phase fluorometer-coupled sensor for monitoring oxygen partial pressure in gases and liquids. A fluorescence method was used to measure the partial pressure of dissolved or gaseous oxygen. Optical fiber carried excitation light produced by the blue LED to the thin-film coating at the probe tip. The probe collected fluorescence generated at the tip and carried it via the optical fiber to the high-sensitivity spectrometer. The degree of fluorescence quenching relates to the frequency of collisions, and therefore to the concentration, pressure and temperature of the oxygen-containing media.

The thin film used in the probe tips is reported to consume no oxygen, allowing for continuous contact with the sample. Additionally, FOXY Sensors are reported to be immune to interference caused by pH change or from changes in ionic strength, salinity, and biofouling.

The measurement was taken as follows. The pulsed blue LED sent light at about 475 nm to an optical fiber. The optical fiber carried the light to the oxygen probe. The distal end of the probe tip consisted of a thin layer of a hydrophobic sol-gel material. A ruthenium complex was trapped in the sol-gel matrix, which immobilized the ruthenium complex and protected it from water. The light from the LED excited the ruthenium complex at the probe tip. The excited ruthenium complex fluoresced, emitting energy at about 600 nm.

If the excited ruthenium complex encountered an oxygen molecule, the excess energy was transferred to the oxygen molecule in a non-radiative transfer, decreasing or quenching the fluorescence signal.

The energy was collected by the probe and carried through the optical fiber to the spectrometer. The A/D converter converted this analog data to digital data, which was displayed in the OOISensors software.

Example 11

Oxygen Levels and Formulation Stability

A 2% w/w rapamycin, 4% w/w ethanol, 94% w/w PEG400 formulation was prepared by the method of Example 3, and blanketed with air or the gas indicated in Table 3. Nitrogen blanketing resulted in 0.8% oxygen gas in the headspace. Air blanketing resulted in 20.4% oxygen gas in the headspace. Oxygen blanketing resulted in 84.7% oxygen gas in the headspace.

100 ml of the formulation was filled in 100 ml amber bottles and stored. For each sample, 1 ml of this formulation was placed in a 2 ml vial. Samples were sparged (bubbled) with oxygen gas for the period of time indicated in Table 3. Samples were allowed to equilibrate for 24 hours before the percent oxygen in the head space and in the dissolved gas was measured by the method described in Example 10.

There were 3 replicates for the stability measurement at each time point. For the percent oxygen measurement, there were three replicates per treatment groups 1, 2, 3, and 6, two replicates per treatment groups 4, 5, 7, 8 and 12, and one replicate per treatment groups 9, 10, 11 and 13. Samples were kept at room temperature and in the dark prior to analysis.

Stability was measured by calculating the weight percent of rapamycin at a particular time point relative to the weight of rapamycin added to the original formulation. Stability was measured at 1 week, 2 weeks, 1 month, and 2 months by the method described in Example 1. Results are shown in Table 3, and depicted graphically in FIGS. 3, 4 and 5.

Without being bound by theory, samples sparged with oxygen for 10 or 30 minutes may show a higher percent of rapamycin due to evaporation of ethanol.

Figure 3:
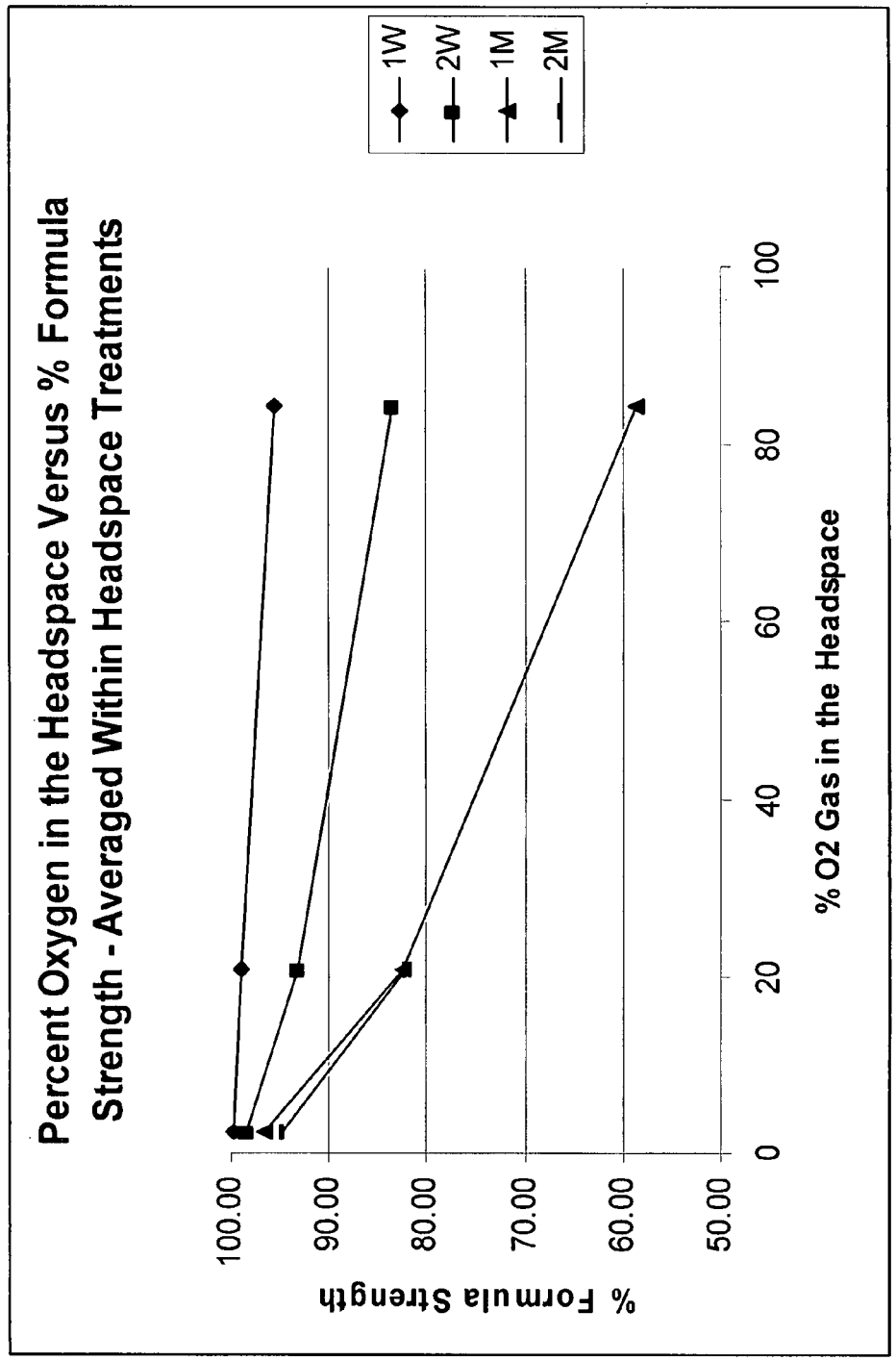
FIG. 3 shows the percent of oxygen in the head space versus the percent formula strength at 1 week (1 W), 2 weeks (2 W), 1 month (1 M), and 2 months (2 M); treatment groups have been averaged within head space treatments (e.g., all samples from treatment groups 1-7 were averaged, all samples from treatment groups 8-12 were averaged, and all samples from treatment group 13 were averaged).

FIG. 3 shows the percent of oxygen in the head space versus the percent formula strength at 1 week, 2 weeks, 1 month, and 2 months for treatment groups 1-13. Treatment groups were averaged within head space treatments (e.g., all samples from each of treatment groups 1-7, 8-12, and treatment group 13 were averaged). Across all treatment groups, the averaged data consistently correlated a higher percentage formula strength with a lesser percentage of oxygen in the head space.

Figure 4:
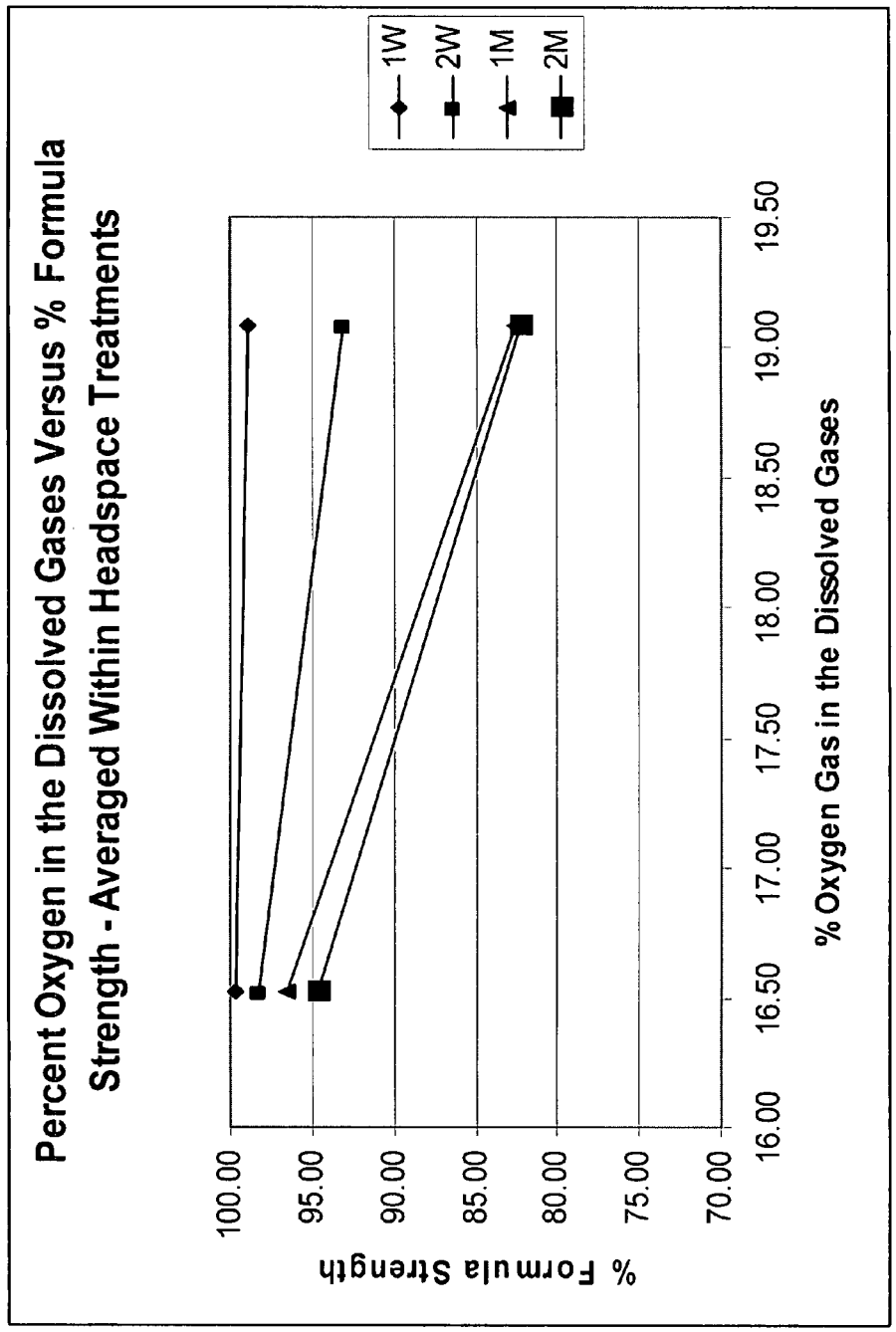
FIG. 4 shows the percent of oxygen in the dissolved gases versus the percent formula strength at 1 week (1 W), 2 weeks (2 W), 1 month (1 M), and 2 months (2 M); treatment groups have been averaged within head space treatments (e.g., all samples from treatment groups 1-7 were averaged, all samples from treatment groups 8-12 were averaged, and all samples from treatment group 13 were averaged).

FIG. 4 shows the percent of oxygen in the dissolved gases versus the percent formula strength at 1 week, 2 weeks, 1 month, and 2 months for treatment groups 1-13. Treatment groups were averaged within head space treatments (e.g., all samples from treatment groups 1-7 were averaged, all samples from treatment groups 8-12 were averaged, and all samples from treatment group 13 were averaged). Across all treatment groups, the averaged data consistently correlated a higher percentage formula strength with a lesser percentage of oxygen in the head space.

Figure 5:
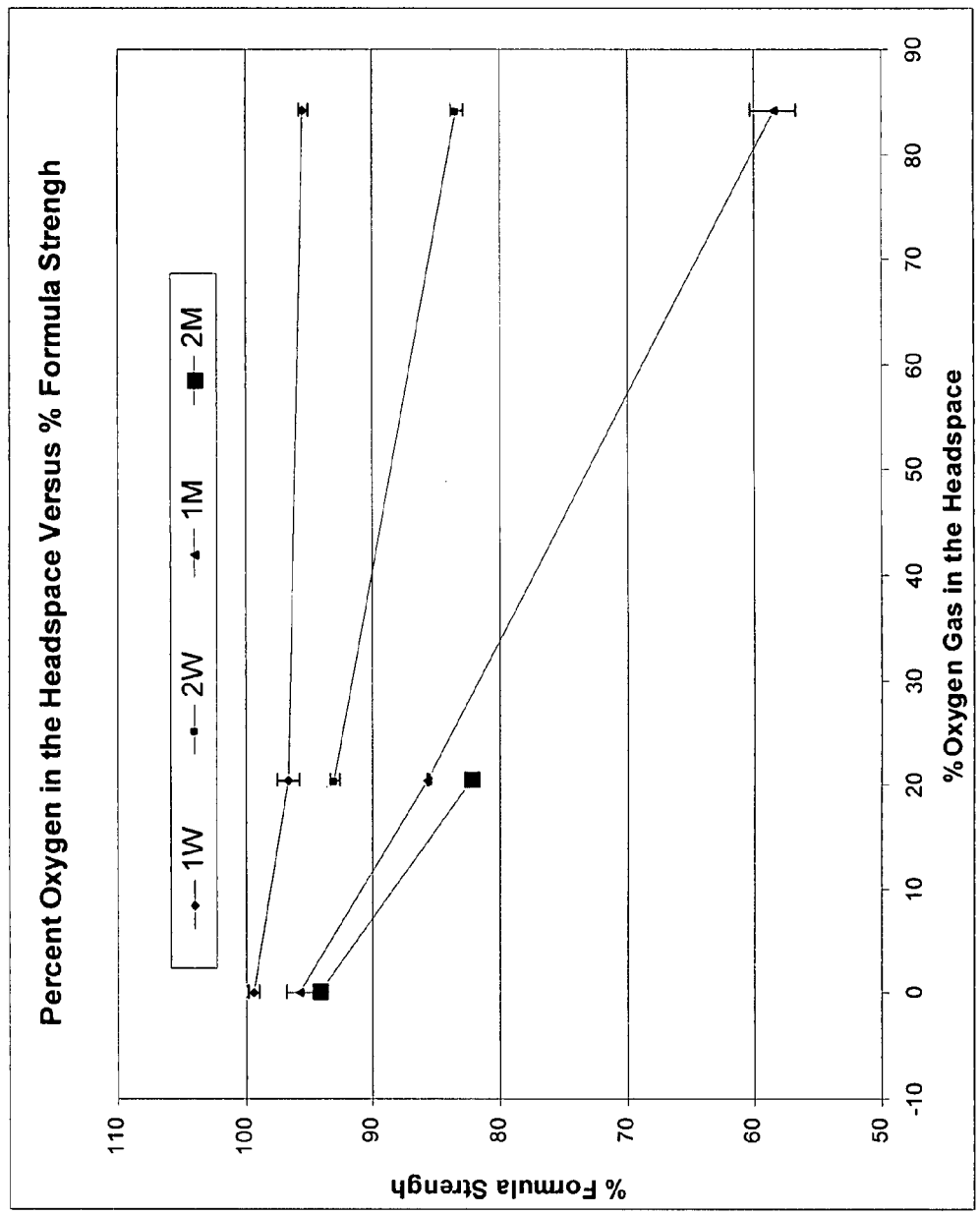
FIG. 5 shows the percent formula strength relative to the percent of oxygen gas in the head space for treatment groups 1, 8 and 13 (treatment groups that were not subjected to oxygen sparging) at 1 week (1 W), 2 weeks (2 W), 1 month (1 M), and 2 months (2 M).

FIG. 5 shows the percent formula strength relative to the percent of oxygen gas in the head space for treatment groups 1, 8 and 13 (treatment groups that were not subjected to oxygen sparging) at 1 week, 2 weeks, 1 month, and 2 months. At all time points, the averaged data consistently correlated greater formula strength with a lesser percentage of oxygen in the head space.

Example 12

Correlation of Formulation Strength with Microliters of Oxygen in the Head Space per Milligram of Rapamycin in a 2% Rapamycin Formulation The microliter amount of oxygen in the head space per milligram of rapamycin in a 2% rapamycin formulation was calculated for a number of samples, and the microliter amount of oxygen per milligram of rapamycin effect on formulation strength over a period of time is shown in FIGS. 6A, 6C, 7A, and 8A.

The rapamycin formulation was prepared as described in Example 4 for data in Table 4. The rapamycin formulation was prepared as described in Example 11 for data in Table 5. All of the formulations analyzed in FIGS. 6A, 6B, 7A, 7B, 8A and 8B had been blanketed with nitrogen. In particular, the 0.5 ml fill volume samples from Table 1 showing potency 98.6% at time zero were used, and the 2.0 ml fill volume samples from Table 1 showing potency 96.1% at time zero were used. For FIG. 6C, the blanketing treatments were the nitrogen blanket treatment group 1 from Example 11 (resulting in 0.80% oxygen gas in the head space), the air blanket treatment group 8 from Example 11 (resulting in 20.4% oxygen gas in the head space), and the oxygen blanket treatment group 13 from Example 11 (resulting in 84.7% oxygen gas in the head space).

The amount of oxygen in the head space was calculated as follows. The percentage of oxygen in the headspace was determined using the fiber optic fluorescence based probe described in Example 10. Based on the percent of oxygen in the head space, and the volume of head space, the amount of oxygen in terms of µl was calculated. For example, if the head space volume was 2.0 ml (2000 µl) and the percent of oxygen measured was 0.8%, the amount of oxygen in the head space was 0.8% of 2.0 ml, which was 16 µl.

The mg amount of rapamycin in the fill volume was calculated by converting the solution volume to mass using the solution density of 1.1. The mass was multiplied by the 2% concentration of rapamycin in the solution. For example, for a 0.5 ml fill volume there was 0.55 g of solution. For 2% in 0.55 g, the amount of rapamycin in the fill volume was 11 mg.

Accordingly, the amount of oxygen in the head space per mg of rapamycin in the fill volume was 16 µl/11 mg, or 1.455 µl/mg of rapamycin.

The formulation strength for the 25° C. samples at various time points was from Table 3, and was summarized along with the microliter amount of oxygen per milligram of rapamycin in Tables 4 and 5. Data from treatments 1, 8 and 13 are shown in Table 5. The formulation strength for the 5° C. and −20° C. samples at various time points was from Table 1, and was summarized along with the microliter amount of oxygen per milligram of rapamycin in Table 4. Note that, though Table 1 shows a percent drop in rapamycin/rapamycin potency, this is a percent drop relative to the time zero formulation. Thus, the formulation strengths shown in Table 4 were obtained by subtracting the percent drop in rapamycin potency from 100, and multiplying the resulting number by the time zero formulation strength.

Figure 7:
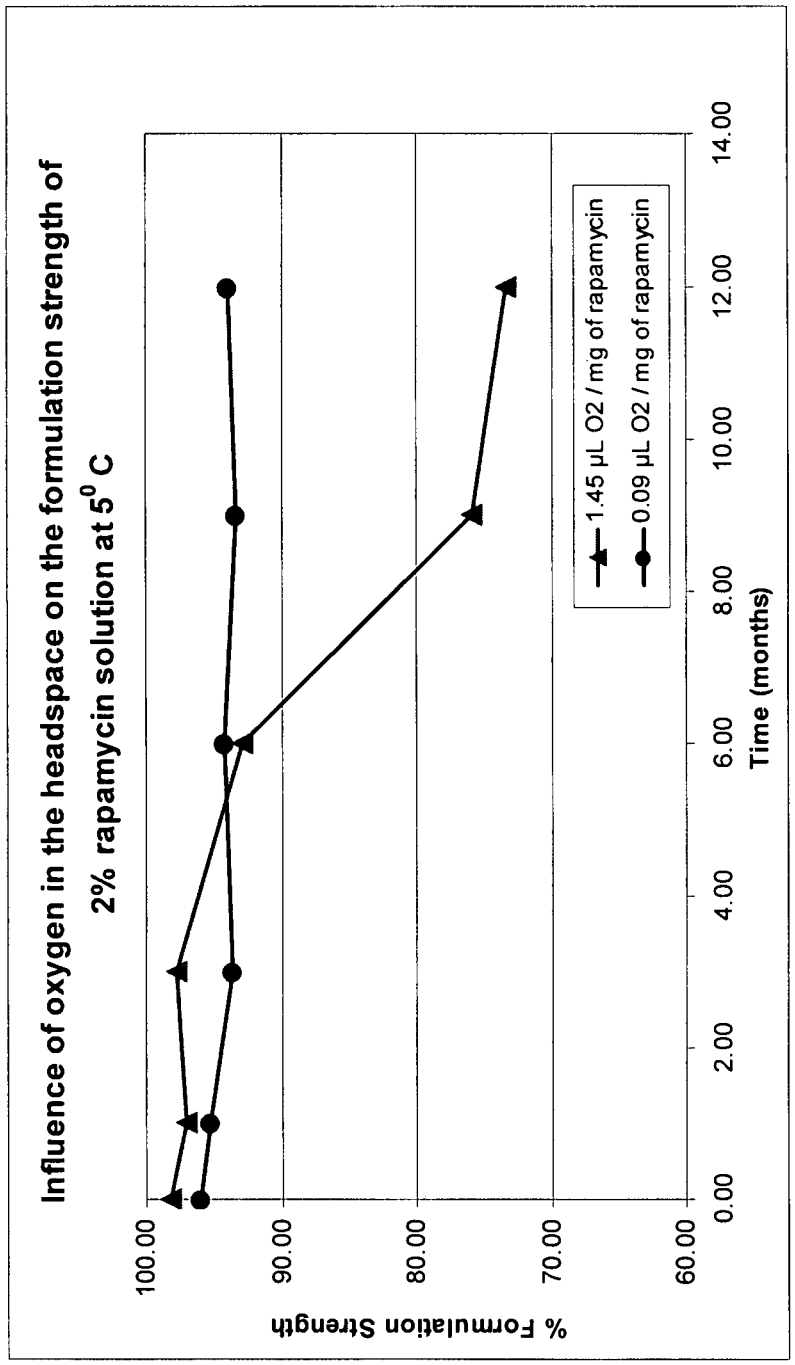
FIG. 7A shows the influence of the amount of oxygen in the head space on the formula strength of a 2% rapamycin solution at 5° C.
FIG. 7B shows the influence of the head space to fill volume ratio (HS/FV) on the formulation strength of a 2% rapamycin solution at 5° C.
Figure 7:
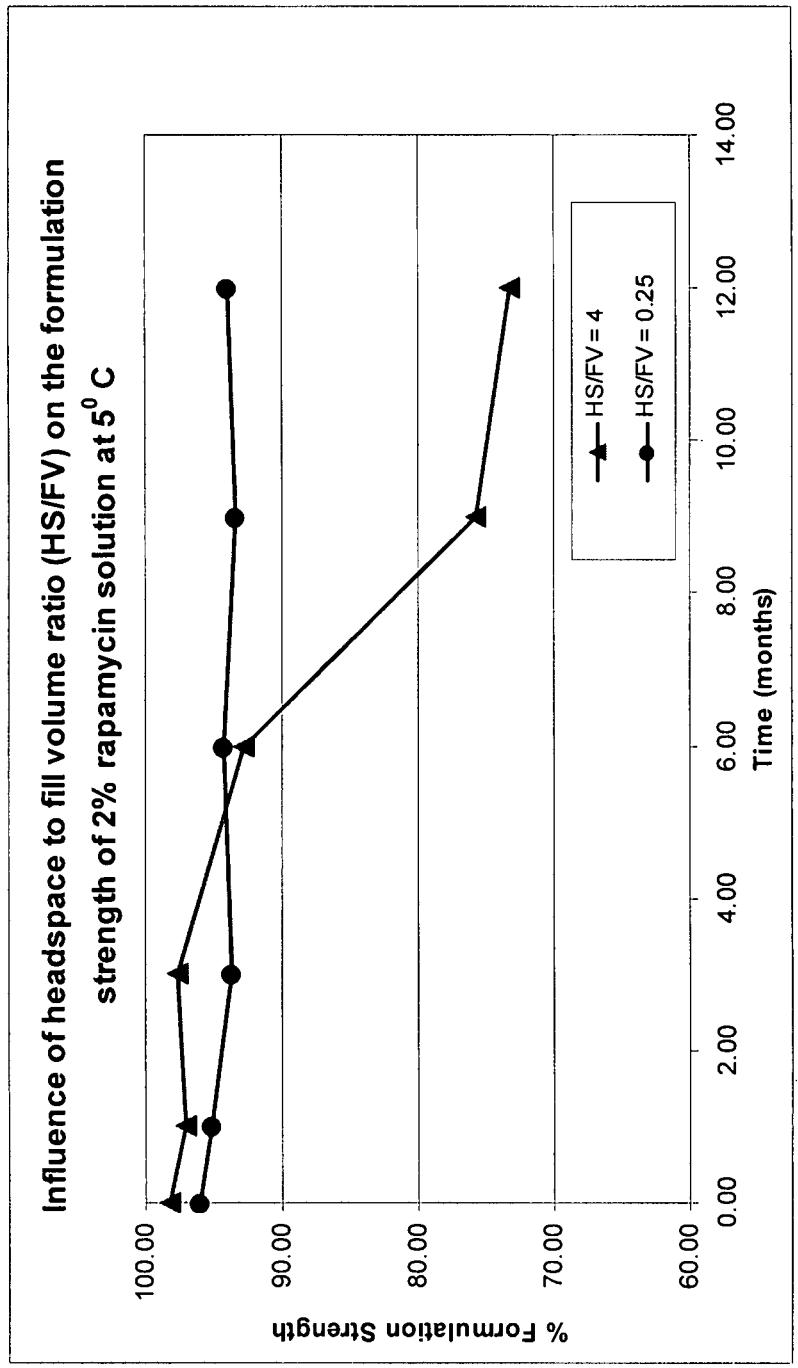

As can be seen in FIGS. 6A and 7A, the groups with the lower microliters of oxygen gas in the head space to milligrams of rapamycin in the formulation had a higher formulation strength over extended periods of time at the 25° C. and 5° C. temperatures. Not being bound by theory, it appears that the effect of the lower temperature in the −20° C. group was larger than the effect of the oxygen gas in the head space to milligrams of rapamycin in the formulation.

Example 13

Correlation of Head Space to Fill Volume Ratio with Formulation Strength

Figure 8:
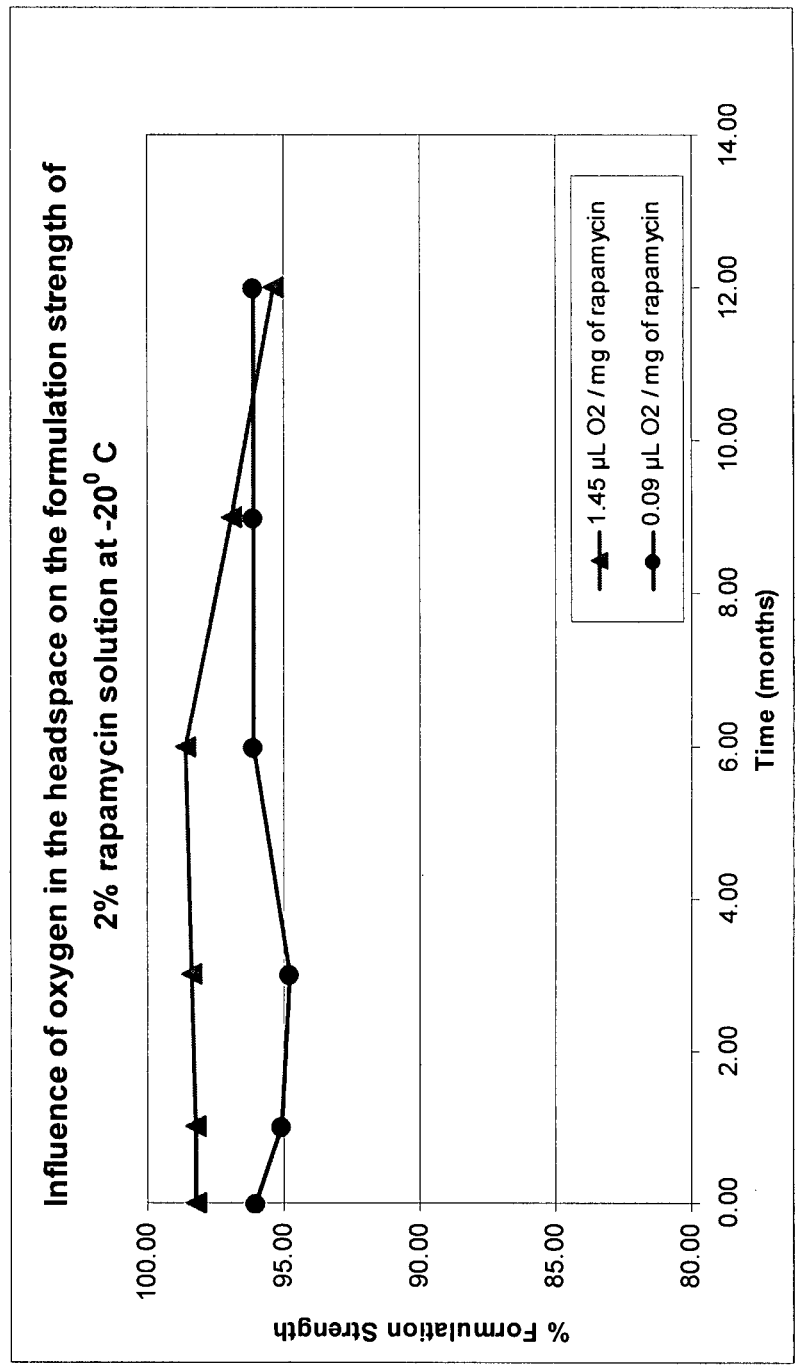
FIG. 8A shows the influence of the amount of oxygen in the head space on the formula strength of a 2% rapamycin solution at −20° C.
FIG. 8B shows the influence of the head space to fill volume ratio (HS/FV) on the formulation strength of a 2% rapamycin solution at −20° C.
Figure 8:
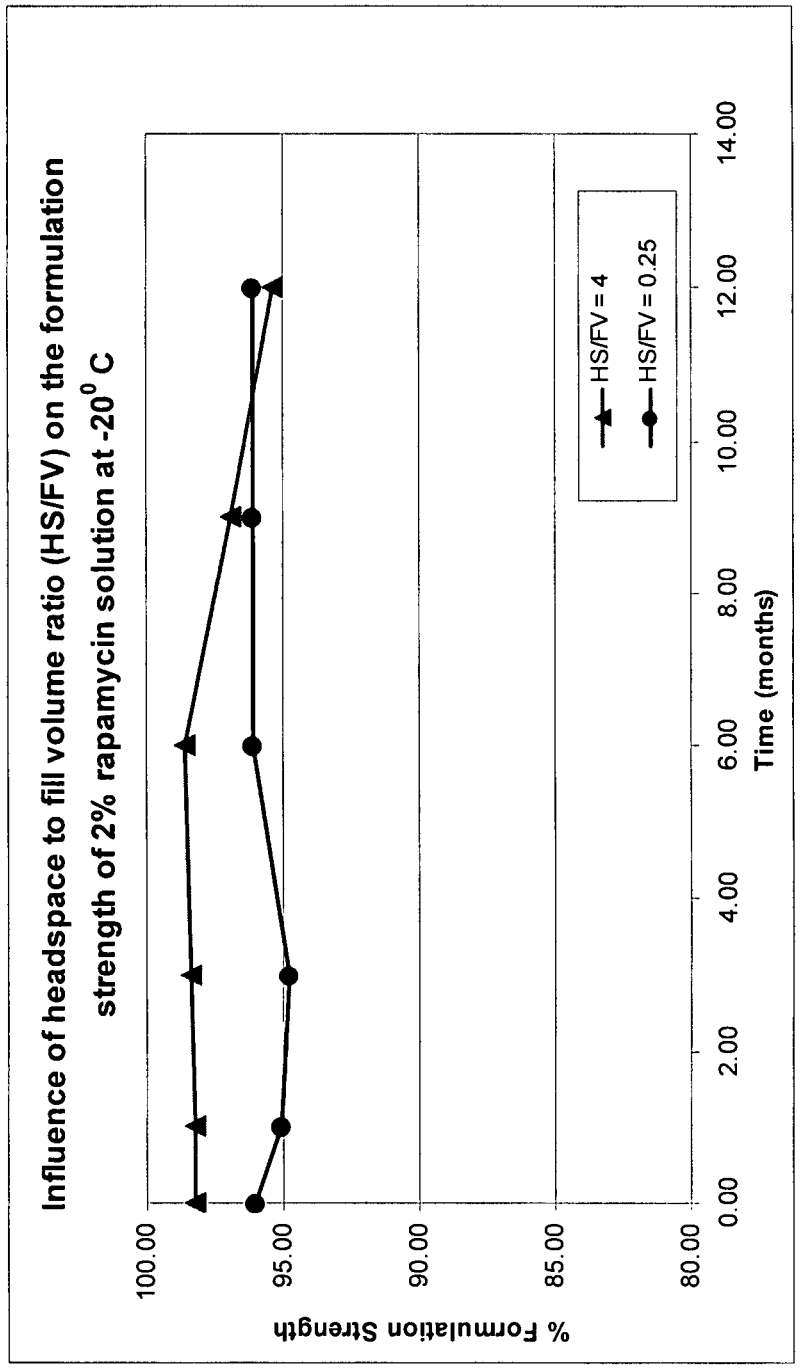

The ratio of the head space to fill volume is shown in FIGS. 6B, 7B and 8B. The head space to fill volume ratio was calculated by dividing the head space volume by the fill volume. The head space per fill volume ratios are shown in Table 4. Note that, though the vials were all 2 ml vials, there is additional head space volume in these vials which was taken into account in calculating the head space to fill volume ratios.

As can be seen in FIGS. 6B and 7B, the lower head space to fill volume groups had a higher formulation strength over extended periods of time at the 25° C. and 5° C. temperatures. Not being bound by theory, it appears that the effect of the lower temperature in the −20° C. group was larger than the effect of the head space to fill volume ratio.

All references cited herein, including patents, patent applications, and publications, are hereby incorporated by reference in their entireties, whether previously specifically incorporated or not.

TABLE 1

| | | Fill | | Percent drop in Rapamycin Potency | | | | | | | | | | | | | |
|---|---|---|---|---|---|---|---|---|---|---|---|---|---|---|---|---|---|
| 2 mL | | vol in | % potency | Months of storage at 25° C. | | | | Months of storage at 5° C. | | | | | | Months of storage at −20° C. | | | | |
| Ex vial | BHT | mL | $T_0$ | $T_1$ | $T_2$ | $T_3$ | $T_1$ | $T_2$ | $T_3$ | $T_6$ | $T_9$ | $T_{12}$ | $T_1$ | $T_2$ | $T_3$ | $T_6$ | $T_9$ | $T_{12}$ |
| 1 Amber | N | 0.5 | 98.10 | 29 | | | 5.20 | 14 | 22.30 | 26.70 | | | 1.20 | 5.10 | 8.80 | 21.50 | | |
| Clear | N | 2 | 96.78 | 3 | 4 | 9 | | | | | | | | | | | | |
| 2 Clear | N | 2 | 98.74 | 7.00 | 6.80 | 9.60 | 4.90 | 5.40 | 7.70 | 9.30 | | | 0.60 | 0.20 | 1.70 | 1.70 | | |
| | Y | 2 | 99.68 | 4.20 | 6.00 | 10.80 | 2.30 | 1.50 | 4.40 | 5.20 | | | 0.90 | 0.70 | 3.10 | 2.40 | | |
| | Y | 0.5 | | 5.20 | 5.80 | 10.80 | 3.30 | 2.00 | 4.10 | 6.00 | | | 1.50 | 1.40 | 3.00 | 2.20 | | |
| 3 Clear | Y | 2 | 100.8 | 0.29 | 4.82 | 8.72 | 0.00 | 0.00 | 1.72 | 2.52 | | | 0.00 | 0.00 | 2.18 | 1.40 | | |
| | Y | 0.5 | | 0.00 | 4.70 | 9.53 | 0.00 | 0.08 | 2.38 | 2.50 | | | 0.00 | 0.59 | 1.26 | 1.40 | | |
| Clear | N | 2 | 97.82 | 6.30 | 5.50 | 9.94 | 1.10 | 1.30 | 7.00 | 6.86 | | | 0.20 | 0 | 1.76 | 0.90 | | |

TABLE 1-continued

| | | | Fill vol in mL | % potency $T_0$ | Percent drop in Rapamycin Potency | | | | | | | | | | | | | | |
|---|---|---|---|---|---|---|---|---|---|---|---|---|---|---|---|---|---|---|---|---|
| | | | | | Months of storage at 25° C. | | | Months of storage at 5° C. | | | | | | Months of storage at −20° C. | | | | | |
| Ex | vial | BHT | | | $T_1$ | $T_2$ | $T_3$ | $T_1$ | $T_2$ | $T_3$ | $T_6$ | $T_9$ | $T_{12}$ | $T_1$ | $T_2$ | $T_3$ | $T_6$ | $T_9$ | $T_{12}$ |
| 4 | Clear | N | 0.5 | 98.23 | | 23.50 | 24.40 | 0.20 | | 0.20 | 7.05 | 21.70 | 24.36 | 1.90 | 0* | 0* | | 0.95 | 2.47 |
| | | | 2.0 | | 5.40 | 6.40 | 6.70 | 0.10 | | 0* | 2.93 | 6.48 | 10.18 | 0.80 | 0* | 0* | | 0.49 | 2.94 |
| 4 | Clear | N | 0.5 | 98.60 | 12.10 | 16.40 | 16.80 | 1.60 | | 0.90 | 5.84 | 23.12 | 25.66 | 0.40 | 0.20 | 0* | | 1.72 | 3.25 |
| | | | 2.0 | | 5.60 | 5.00 | 6.00 | 1.20 | | 1.50 | 2.7 | 7.85 | 13.56 | 0.50 | 0* | 0* | | 1.12 | 3.42 |
| 4 | Clear | N | 2.0 | 96.1 | 4.90 | | 6.90 | 0.92 | | 2.50 | 1.98 | 2.81 | 2.29 | 1.09 | 1.34 | 0* | 0* | | |
| 4 | Clear | N | 2.0 | 100.0** | 7.20 | | 13.10 | 3.50 | | 7.90 | 4.50 | 2.60 | | 2.20 | 5.40 | 1.70 | 1.60 | | |
| 4 | Clear | N | 2.0 | 96.00 | 2.60 | | 5.83 | 0* | | 0* | | | | 0* | 0* | 0* | | | |

\* = values are negative (within 1%), method allows up to ±3% variation in the results
\*\* = determined to be out of trend value; values should be between 96–98%

TABLE 2

| Form. # | Composition (mg), % (w/w) | Formulation Type |
|---|---|---|
| 1 | DMSO = 2000 mg (20%)<br>Water = 8000 mg (80%) | S |
| 2 | F68 = 1000 mg (10%)<br>Water = 9000 mg (90%) | S |
| 3 | F68 = 3000 mg (30%)<br>Water = 7000 mg (70%) | S |
| 4 | F127 = 1000 mg (10%)<br>Water = 9000 mg (90%) | S |
| 5 | F127 = 1500 mg (15%)<br>Water = 8500 mg (85%) | S |
| 6 | Beta-cyclodextrin = 250 mg (2.5%)<br>Water = 9750 mg (97.5%) | S |
| 7 | Rapa = 10.2 mg (0.101%)<br>Pluronic, F68 = 1010 mg (9.99%)<br>Water = 9090 mg (89.909%) | S |
| 8 | Rapa = 10.2 mg (0.102%)<br>Pluronic, F68 = 3000 mg (29.969%)<br>Water = 7000 mg (69.929%) | S |
| 9 | Rapa = 10.5 mg (0.104%)<br>Pluronic, F127 = 1010 mg (9.99%)<br>Water = 9090 mg (89.907%) | S |
| 10 | Rapa = 10.5 mg (0.105%)<br>Pluronic, F127 = 1500 mg (14.984%)<br>Water = 8925 mg (84.9%) | S |
| 11 | Rapa = 10.7 mg (0.105%)<br>Beta-cyclodextrin = 255 mg (2.497%)<br>Water = 9945 mg (97.398%) | S |
| 12 | Rapa = 6.4 mg (0.0999%)<br>CMC = 48 mg (0.7493%)<br>Polysorbitan 20 = 2.56 mg (0.04%)<br>Water = 6349.44 mg (99.111%) | SP |
| 13 | Rapa = 6.5 mg (0.0999%)<br>DMSO = 325 mg (4.995%)<br>Water = 6175 mg (94.905%) | S |
| 14 | Rapa = 13.5 mg (0.0999%)<br>CMC = 101.25 mg (0.7493%)<br>Polysorbitan 20 = 5.4 mg (0.04%)<br>Water = 13393.35 mg (99.112%) | SP |
| 15 | Rapa = 11.0 mg (0.2%)<br>EtOH = 5500 mg (99.8%) | S |
| 16 | Rapa = 6.6 mg (0.1%)<br>EtOH = 1054.6 mg (15.933%)<br>F127 = 833.64 mg (12.595%)<br>Water = 4723.96 mg (71.372%) | S |
| 17 | Rapa = 5 mg (0.1%)<br>Cavitron = 0.25 g (5%)<br>Ethanol, 95% = 57 mg (1.1%)<br>Sterile water = 4.753 g (93.8%) | S |
| 18 | Rapa = 5 mg (0.1%)<br>Ethanol, 95% = 150 mg (2.9%)<br>PEG400 = 1.0 g (19.4%)<br>Sterile water = 4.01 g (77.6%) | S |
| 19 | Rapa = 5 mg (0.1%)<br>Ethanol, 95% = 152 mg (3.2%)<br>PEG 400 = 1.5227 g (30.2%)<br>Sterile water = 3.3592 g (66.67%) | S |
| 20 | Rapa = 6.6 mg (0.1%)<br>EtOH = 505.1 mg (7.618%)<br>F127 = 917.8 mg (13.843%)<br>Water = 5200.6 mg (78.44%) | S |
| 21 | Rapa = 6.6 mg (0.1%)<br>EtOH = 536 mg (7.5%)<br>Pluronic, F127 = 983.75 mg (14.0%)<br>Water = 5574.56 mg (78.4%) | S |
| 22 | Rapa = 5.2 mg (0.1023%)<br>EtOH = 56.6 mg (1.127%)<br>Captisol = 2008.9 mg (39.5%)<br>Water = 3013.3 mg (59.3%) | S |
| 23 | Rapa = 6.9 mg (0.201%)<br>EtOH = 3418.0 mg (99.799%) | S |
| 24 | Rapa = 9.1 mg (0.491%)<br>EtOH = 90.9 mg (4.908%)<br>F127 = 262.8 mg (14.191%)<br>Water = 1489.1 mg (80.409%) | S |
| 25 | Rapa = 0 mg (0%)<br>EtOH = 310.2 mg (5.144%)<br>F127 = 858.1 mg (14.228%)<br>Water = 4862.6 mg (80.628%) | S |
| 26 | Rapa = 0 mg (0%)<br>EtOH = 613.1 mg (10.19%)<br>F127 = 810.6 mg (13.471%)<br>Water = 4593.6 mg (76.339%) | S |
| 27 | Rapa = 53.5 mg (1.095%)<br>EtOH = 414.8 mg (8.488%)<br>F127 = 662.8 mg (13.563%)<br>Water = 3755.7 mg (76.854%) | S |
| 28 | Rapa = 0.3 g (10%)<br>PVP K90 = 0.35 g (12%)<br>Eudragit RS30D = 2.35 g (78%) | ISG, SP |
| 29 | Rapa = 0.2154 g (7.31%)<br>PVP K90 = 0.25 g (8.5%)<br>Eudragit RS30D = 2.48 g (84.19%) | ISG, SP |
| 30 | Rapa = 53.9 mg (1.103%)<br>EtOH = 413.6 mg (8.463%)<br>Sterile water = 3843.5 mg (78.647%)<br>F127 (Lutrol) = 576.0 mg (11.786%) | S |
| 31 | Rapa = 0 mg (0%)<br>EtOH = 411.9 mg (8.513%)<br>Sterile Water = 3849.3 mg (79.554%)<br>F127 (Lutrol) = 577.4 mg (11.933%) | S |
| 32 | Rapa = 54.1 mg (1.256%)<br>EtOH = 416.8 mg (9.676%)<br>Sterile Water = 3836.3 mg (78.569%)<br>F127 (Lutrol) = 577.5 mg (10.499%) | S |
| 33 | Rapa = 80.7 mg (1.964%)<br>EtOH = 65.0 mg (0.158%)<br>PEG 400 = 4021.8 mg (97.878%) | S |
| 34 | Rapa = 106.9 mg (5.233%)<br>EtOH = 129.6 mg (6.344%)<br>PEG 400 = 1806.5 mg (88.424%) | S |

TABLE 2-continued

| Form. # | Composition (mg), % (w/w) | Formulation Type |
|---|---|---|
| 35 | Rapa = mg (0%)<br>PVP K90 = 0.204 g (2.3%)<br>Ethanol, 100% = 0.4 g (4.5%)<br>Eudragit RL100 = 0.201 g (2.3%)<br>PEG 400 = 8.00 g (90.9%) | ISG, SP |
| 36 | Rapa = 0 mg (0%)<br>PVP K90 = 0.2 g (2.2%)<br>Ethanol, 100% = 0.4 g (4.4%)<br>PVAP = 0.4 g (4.4%)<br>PEG 400 = 8.00 g (88.9%) | ISG, SP |
| 37 | Rapa = 106.1 mg (4.2%)<br>PVP K90 = 55.2 mg (2.2%)<br>Ethanol, 100% = 108 mg (4.3%)<br>Eudragit RL 100 = 55 mg (2.2%)<br>PEG 400 = 2.2 g (87.1%) | ISG, SP |
| 38 | Rapa = 399.6 mg (9.965%)<br>F68 (Lutrol) = 40.6 mg (1.012%)<br>Sterile Water = 3569.7 mg (89.022%) | S |
| 39 | Rapa = 53.8 mg (1.1%)<br>EtOH = 415.2 mg (8.489%)<br>Sterile Water = 3844.2 mg (78.594%)<br>F127 = 578.0 mg (11.817%) | S |
| 40 | Rapa = 208.1 mg (3.148%)<br>PEG 400 = 6403.4 mg (96.852%) | S |
| 41 | Rapa = 200.4 mg (5.148%)<br>F68 (Lutrol) = 20.8 mg (0.534%)<br>PEG 400 = 3569.3 mg (91.697%)<br>EtOH (95%) = 102 mg (2.62%) | SP |
| 42 | Rapa = 200.4 g (5.259%)<br>PEG 400 = 3561.4 mg (93.46%)<br>Tween 80 = 48.8 mg (1.281%) | SP |
| 43 | Rapa = 30.9 mg (1.03%)<br>PEG 400 = 2.9624 g (98.97%) | S |
| 44 | Rapa = 61 mg (1.96%)<br>Ethanol, 100% = 0.1860 g (6%)<br>PEG 400 = 2.8588 g (92.04%) | S |
| 45 | Rapa = 90.7 mg (3.02%)<br>Ethanol, 100% = 0.2722 g (9.06%)<br>PEG 400 = 2.6423 g (87.94%) | S |
| 46 | Rapa = 101.6 mg (4.997%)<br>EtOH = 331.6 mg (16.308%)<br>PEG 400 = 1600.1 mg (78.695%) | S |
| 47 | Rapa = 120.9 g (3.189%)<br>F68 (Lutrol) = 42.4 mg (1.118%)<br>Sterile Water = 3627.7 mg (95.692%) | SP |
| 48 | Rapa = 100.1 g (1.999%)<br>EtOH = 305.1 mg (6.092%)<br>PEG 400 = 4602.9 mg (91.909%) | S |
| 49 | Rapa = 150.5 mg (3.004%)<br>PEG 400 = 4860.3 mg (96.996%) | SP |
| 50 | Rapa = 153.4 mg (3.055%)<br>F68 (Pluronic) = 50.6 mg (1.008%)<br>Sterile Water = 4816.6 mg (95.937%) | SP |
| 51 | Rapa = 116.6 mg (2.29%)<br>EtOH = 306.6 mg (6.05%)<br>PEG 400 = 4647.5 mg (91.66%) | S |
| 52 | Rapa = 150.4 mg (2.994%)<br>F68 Lutrol = 15.4 mg (0.306%)<br>Sterile water = 4859.1 mg (96.7%) | SP |
| 53 | Rapa = 306.5 mg (6.088%)<br>PEG 400 = 4727.7 mg (93.912%) | SP |
| 54 | Rapa = 309.3 mg (6.146%)<br>PEG 400 = 4723.3 mg (93.854%) | SP |
| 55 | Rapa = 303.3 mg (6.061%)<br>PEG 400 = 4700.6 mg (93.939%) | SP |
| 56 | Rapa = 305.4 mg (6.088%)<br>PEG 400 = 4711.0 mg (93.912%) | SP |
| 57 | Rapa = 306.9 mg (6.098%)<br>PEG 400 = 4725.5 mg (93.902%) | SP |
| 58 | Rapa = 302.5 mg (6.021%)<br>PEG 400 = 4721.6 mg (93.979%) | SP |
| 59 | Rapa = 304.5 mg (6.053%)<br>PEG 400 = 4726.4 mg (93.947%) | SP |
| 60 | Dexamethasone = 251.4 mg (5.011%)<br>PEG 400 = 4765.2 mg (94.989%) | SP |
| 61 | Dexamethasone = 252.4 mg (5%)<br>PEG 400 = 4600 mg (92%)<br>EtOH = 150 mg (3%) | SP |
| 62 | Rapa = 32.2 mg (0.641%)<br>PEG 400 = 4677.9 mg (93.096%)<br>EtOH = 314.7 mg (6.263%) | S |
| 63 | Rapa = 32.3 mg (0.6%)<br>PEG 400 = 5516.3 mg (93.1%)<br>EtOH = 314.7 mg (6.263%) | S |
| 64 | Rapa = 54.4 mg (1.007%)<br>PEG 400 = 4638.9 mg (92.702%)<br>EtOH = 314.8 mg (6.291%) | S |
| 65 | Rapa = 50.8 mg (1.013%)<br>PEG 400 = 4963.2 mg (98.987%) | S |
| 66 | Rapa = 52.1 mg (1.035%)<br>PEG 400 = 4868.6 mg (96.718%)<br>EtOH = 113.1 mg (2.247%) | S |
| 67 | Rapa = 50.5 mg (1.009%)<br>PEG 400 = 4752.8 mg (94.953%)<br>EtOH = 202.1 mg (4.038%) | S |
| 68 | Rapa = 101.8 mg (2.030%)<br>PEG 400 = 4712.4 mg (93.970%)<br>EtOH = 200.6 mg (4.000%) | S |
| 69 | Rapa = 102.1 mg (2.036%)<br>PEG 400 = 4605.5 mg (91.847%)<br>EtOH = 306.7 mg (6.117%) | S |
| 70 | Rapa = 101.6 mg (2.025%)<br>PEG 400 = 4510.6 mg (89.892%)<br>EtOH = 405.6 mg (8.083%) | S |
| 71 | Rapa = 75.9 mg (3.019%)<br>PEG 400 = 2438.4 mg (96.981%) | SP |
| 72 | Rapa = 50.9 mg (2.034%)<br>PEG 400 = 2350.1 mg (93.914%)<br>EtOH = 101.4 mg (4.052%) | S |
| 73 | Rapa = 12.5 mg (0.620%)<br>PEG 400 = 2004.8 mg (99.380%) | SP |
| 74 | Rapa = 1.20949 g (2.0152%)<br>EtOH = 2.401 g (4.000%)<br>PEG 400 = 56.407 g (93.9848%) | S |
| 75 | Rapa = 16.0 mg (0.795%)<br>EtOH = 80.0 mg (3.976%)<br>PEG 400 = 1916.0 mg (95.2298%) | S |
| 76 | Rapa = 8.1 mg (0.400%)<br>PEG 400 = 2014.5 mg (99.600%) | SP |
| 77 | Rapa = 8.6 mg (0.428%)<br>PEG 400 = 2002.5 mg (99.572%) | S |
| 78 | Rapa = 8.2 mg (0.410%)<br>PEG 400 = 1992.0 mg (99.590%) | S |
| 79 | Rapa = 8.7 mg (0.433%)<br>PEG 400 = 1998.8 mg (99.567%) | S |
| 80 | Rapa = 8.6 mg (0.427%)<br>PEG 400 = 2003.2 mg (99.573%) | S |
| 81 | Rapa = 8.6 mg (0.428%)<br>PEG 400 = 1999.3 mg (99.572%) | S |
| 82 | Rapa = 9.0 mg (0.448%)<br>PEG 400 = 2000.8 mg (99.552%) | S |
| 83 | Rapa = 8.0 mg (0.397%)<br>PEG 400 = 2008.8 mg (99.603%) | S |
| 84 | Rapa = 8.5 mg (0.422%)<br>PEG 400 = 2006.8 mg (99.578%) | S |
| 85 | Rapa = 8.0 mg (0.399%)<br>PEG 400 = 1998.2 mg (99.601%) | S |
| 86 | Rapa = 8.5 mg (0.422%)<br>PEG 400 = 2004.3 mg (99.578%) | S |
| 87 | Rapa = 8.6 mg (0.428%)<br>PEG 400 = 2002.5 mg (99.572%) | S |
| 88 | Rapa = 0.7 g (1.983%)<br>EtOH = 1.4 g (3.966%)<br>PEG 400 = 33.2 g (94.051%) | S |
| 89 | Rapa = 0 g (0%)<br>EtOH = 0.574 g (1.995%)<br>PEG 400 = 28.2 g (98.005%) | S |
| 90 | Rapa = 1.95 g (1.950%)<br>EtOH = 4.05 g (4.050%)<br>PEG 400 = 94.00 g (94000.%) | S |

TABLE 2-continued

| Form. # | Composition (mg), % (w/w) | Formulation Type |
|---|---|---|
| 91 | Rapa = 0.0107 g (0.534%)<br>EtOH = 0.0805 g (4.019%)<br>PEG 400 = 1.912 g (95.447%) | S |
| 92 | Rapa = 0.0081 g (0.403%)<br>EtOH = 0.0804 g (4.003%)<br>PEG 400 = 1.920 g (95.594%) | S |
| 93 | Rapa = 1.992 g (2%)<br>EtOH = 3.9419 (4%)<br>PEG 400 = 93.95 g (94%) | S |
| 94 | Rapa = 0.405 g (0.4%)<br>EtOH = 4.24 g (4%)<br>PEG 400 = 95.6 (95.6%) | S |
| 95 | PEG 400 = 96 g (96%)<br>EtOH = 3.9027 (4%) | S |
| 96 | Rapa = 0.4020 g (0.402%)<br>EtOH = 3.970 g (3.971%)<br>PEG 400 = 95.600 g (95.627%) | S |
| 97 | Rapa = 2.000 g (1.990%)<br>EtOH = 4.000 g (3.980%)<br>PEG 400 = 94.500 g (94.030%) | S |
| 98 | PEG 400 = 96 g (96%)<br>EtOH = 3.92 g (4%) | S |
| 99 | Rapa = 0.4036 g (0.4%)<br>EtOH = 3.9054 g (4%)<br>PEG 400 = 95.6 (95.6%) | S |
| 100 | Rapa = 2.0025 g (2%)<br>EtOH = 3.98 g (4%)<br>PEG 400 = 94.00 g (94%) | S |
| 101 | Rapa = 9.5 mg (0.472%)<br>EtOH = 90.3 mg (4.485%)<br>PEG 600 = 1913.5 mg (95.043%) | S |
| 102 | Rapa = 44.6 mg (2.21%)<br>EtOH = 86.1.0 mg (4.26%)<br>PEG 600 = 1891.1 mg (93.53%) | S |
| 103 | Rapa = 1.97 g (2%)<br>EtOH = 4.10 g (4%)<br>PEG 400 = 94.15 g (94%) | S |
| 104 | Rapa = 1.95 g (2%)<br>EtOH = 4.00 g (4%)<br>PEG 400 = 94.0 g (94%) | S |
| 105 | Rapa = 8.00 g (2%)<br>PEG 400 = 376.0 g<br>EtOH = 16.0 g (4%) | S |
| 106 | Rapa = 6.00 g (2%)<br>PEG 400 = 282.0 g (94%)<br>EtOH = 12.0 g (4%) | S |
| 107 | Rapa = 8.9 mg (0.4434%)<br>EtOH = 80.3 mg (4.0006%)<br>PEG 300 = 1918.0 mg (95.556%) | S |
| 108 | Rapa = 40.8 mg (2.00886%)<br>EtOH = 110.0 mg (5.41605%)<br>PEG 300 = 1880.2 mg (92.57509%) | S |
| 109 | Rapa = 9.9 mg (0.488%)<br>EtOH = 86.7 mg (4.277%)<br>PEG 400/300 (50/50) = 1930.3 mg (95.235%) | S |
| 110 | Dexamethasone = 142.5 mg (4.994%)<br>PEG 400 = 2710.7 mg (95.006%) | SP |
| 111 | Dexamethasone = 134.3 mg (4.891%)<br>PEG 400 = 2611.4 mg (95.109%) | SP |
| 112 | Triamcinolone = 139.2 mg (5.087%)<br>PEG 400 = 2597.4 mg (94.913%) | SP |
| 113 | Triamcinolone = 135.3 mg (5.089%)<br>PEG 400 = 2523.5 mg (94.911%) | SP |
| 114 | EtOH = 206.4 mg (4.121%)<br>PEG 400 = 4801.6 mg (95.879%) | S |
| 115 | Rapa = 43.0 mg (2.144%)<br>PEG 400 = 1962.3 mg (97.8567%) | SP |
| 116 | Rapa = 40.0 mg (2.001%)<br>PEG 400 = 1959.1 mg (97.999%) | SP |
| 117 | Rapa = 42.9 mg (2.142%)<br>PEG 400 = 1959.7 mg (97.858%) | SP |
| 118 | Rapa = 100.8 mg (2.013%)<br>PEG 400 = 4906.0 mg (97.987%) | SP |
| 119 | Rapa = 20.9 mg (0.42%)<br>EtOH = 209.1 mg (4.17%)<br>PEG 400 = 4784.9 mg (95.41%) | S |
| 120 | Rapa = 20.6 mg (0.41%)<br>EtOH = 211.5 mg (4.22%)<br>Benz. Chl = 19.1 mg (0.38%)<br>PEG 400 = 4762.0 mg (94.99%) | S |
| 121 | Rapa = 20.1 mg (0.40%)<br>EtOH = 211.5 mg (4.22%)<br>Benz. Chl = 2.3 mg (0.05%)<br>PEG 400 = 4782.3 mg (95.34%) | S |
| 122 | Rapa = 8.0 g (2%)<br>EtOH = 16.0 g (4%)<br>PEG 400 = 376.0 g (94%) | S |
| 123 | Rapa = 351.3 mg (2.006%)<br>EtOH = 2353.1 mg (4.093%)<br>PEG 400 = 16448.2 mg (93.901%) | S |
| 124 | Rapa = 2.2035 g (2%)<br>EtOH = 4.45 g (4%)<br>PEG 400 = 103.7 g (94%) | S |
| 125 | Rapa = 515.5 mg (2.021%)<br>PEG 400 = 24,993.8 mg (97.979%) | SP |
| 126 | Rapa = 0.3 g (2%)<br>EtOH = 0.6 g (4%)<br>PEG 400 = 14.1 g (94%)<br>BHT = 0.0002 (0.002%) | S |
| 127 | Rapa = 0.3 g (2%)<br>EtOH = 0.6 g (4%)<br>PEG 400 = 14.1 g (94%)<br>BHT = 0.00037 (0.004%) | S |
| 128 | Rapa = 0.3 g (2%)<br>EtOH = 0.6 g (4%)<br>PEG 400 = 14.1 g (94%)<br>BHT = 0.0081 (0.05%) | S |
| 129 | Rapa = 243.2 mg (1.869%)<br>EtOH = 4.88.4 mg (3.753%)<br>PEG 400 = 12283.3 mg (94.378%) | S |
| 130 | Rapa = 0.404 g (2%)<br>EtOH = 0.8 g (4%)<br>PEG 400 = 18.8 g (94%)<br>BHT = 0.00051 (0.002%) | S |
| 131 | Rapa = 0.6024 g (2%)<br>EtOH = 1.2 g (4%)<br>PEG 400 = 28.25 g (94%) | S |
| 132 | Rapa = 2.001 g (2%)<br>EtOH = 4.05 g (4%)<br>PEG 400 = 94.45 g (94%) | S |
| 133 | Rapa = 0.5155 g (2.057%)<br>EtOH = 1.0198 g (4.070%)<br>PEG 400 = 23.5225 g (93.873%) | S |
| 134 | PEG 400 = 9.6 g (96%)<br>EtOH = 0.4 g (4%) | S |
| 135 | Rapa = 0.610 g (2%)<br>EtOH = 1.2 g (4%)<br>PEG 400 = 28.2 g (94%) | S |
| 136 | Rapa = 24.6 mg (1.193%)<br>EtOH = 91.1 mg (4.418%)<br>Tyloxapol = 219.6 mg (10.649%)<br>BSS = 1726.8 mg (83.740%) | S |
| 137 | Rapa = 100.0 mg (1.993%)<br>PEG 400 = 4916.9 mg (98.007%) | SP |
| 138 | Rapa = 201.6 mg (4.005%)<br>PEG 400 = 4831.5 mg (95.995%) | SP |
| 139 | Rapa = 102.4 mg (2.036%)<br>EtOH = 209.0 mg (4.154%)<br>PEG 400 = 4719.3 mg (93.810%) | S |
| 140 | Rapa = 10.3 mg (0.205%)<br>EtOH = 27.4 mg (0.544%)<br>PEG 400 = 4995.8 mg (99.251%) | S |
| 141 | Rapa = 10.6 mg (0.211%)<br>EtOH = 208.4 mg (4.150%)<br>PEG 400 = 4802.3 mg (95.639%) | S |
| 142 | Rapa = 31.5 mg (0.628%)<br>EtOH = 67.1 mg (1.337%)<br>PEG 400 = 4918.9 mg (98.035%) | S |

TABLE 2-continued

| Form. # | Composition (mg), % (w/w) | Formulation Type |
|---|---|---|
| 143 | Rapa = 30.8 mg (0.613%)<br>EtOH = 204.5 mg (4.073%)<br>PEG 400 = 4786.1 mg (95.314%) | S |
| 144 | Rapa = 103.5 mg (2.057%)<br>EtOH = 207.1 mg (4.116%)<br>PEG 400 = 4720.8 mg (93.827%) | S |
| 145 | Rapa = 283.0 mg (2.020%)<br>EtOH = 566.1 mg (4.041%)<br>PEG 400 = 13,160.8 mg (93.939%) | S |
| 146 | Rapa = 280.1 mg (1.998%)<br>EtOH = 565.2 mg (4.033%)<br>PEG 400 = 13,171.7 mg (93.969%) | S |
| 147 | Rapa = 201.6 mg (3.000%)<br>PEG 400 = 6518.8 mg (97.000%) | SP |
| 148 | Rapa = 31.9 mg (1.019%)<br>Benzyl Alcohol = 1021.9 mg (20.070%)<br>Sesame Oil = 4017.9 mg (78.911%) | S |
| 149 | Rapa = 51.5 mg (1.03%)<br>Benzyl Alcohol = 259.9 mg (5.19%)<br>Sesame Oil = 4694.3 mg (93.78%) | S |
| 150 | Rapa = 5.96 g (2%)<br>EtOH = 12.0 g (4%)<br>PEG 400 = 282.0 g (94%) | S |
| 151 | Rapa = 54.5 mg (1.07%)<br>Benzyl Alcohol = 1014.3 mg (19.95%)<br>Olive Oil = 4014.8 mg (78.98%) | S |
| 152 | Rapa = 0 mg (0.00%)<br>Benzyl Alcohol = 269.4 mg (5.421%)<br>Tyloxapol = 608.2 mg (12.238%)<br>Sesame Oil = 4092.2 mg (82.341%) | S |
| 153 | Rapa = 76.3 mg (1.75%)<br>Benzyl Alcohol = 307.0 mg (7.06%)<br>Tyloxapol = 607.8 mg (13.97%)<br>Sesame Oil = 3000.5 mg (68.97%)<br>Span 80 = 63.1 mg (1.45%)<br>EtOH = 295.5 mg (6.79%) | S |
| 154 | Form. # 150 = 200 g (99.998%)<br>BHT = 0.004 g (0.002%) | S |
| 155 | Rapa = 51.0 mg (0.87%)<br>EtOH = 642.3 mg (10.93%)<br>Benzyl Alcohol = 431.8 mg (7.34%)<br>Sesame Oil = 4753.7 mg (80.86%) | S |
| 156 | Rapa = 51.4 mg (1.03%)<br>Benzyl Alcohol = 518.4 mg (10.34%)<br>Olive Oil = 4444.7 mg (88.64%) | S |
| 157 | Rapa = 8.1 g (2%)<br>EtOH = 16.0 g (4%)<br>PEG 400 = 376.0 g (94%) | S |
| 158 | Form. # 157 = 225.00 g (99.998%)<br>BHT = 0.0045 g (0.002%) | S |
| 159 | Rapa = 8.1 g (2%)<br>EtOH = 16.0 g (4%)<br>PEG 400 = 376 g (94%) | S |
| 160 | Form. # 159 = 112.0 g (99.998%)<br>BHT = 0.00224 g (0.002%) | S |
| 161 | Form. # 159 = 112.0 g (99.998%)<br>BHT = 0.0019 g (0.002%) | S |
| 162 | Rapa = 55.4 mg (1.10%)<br>EtOH = 112.7 mg (2.25%)<br>Benzyl Alcohol = 157.8 mg (3.15%)<br>Cotton Seed Oil = 4688.0 mg (93.50%) | S |
| 163 | Rapa = 5.005 g (1%)<br>EtOH = 10.0 g (2%)<br>PEG 400 = 485.5 g (97%) | S |
| 164 | PEG 400 = 9.82 g (98%)<br>EtOH = 0.235 g (2%) | S |
| 165 | Form. # 163 = 100.25 g (99.998%)<br>BHT = 0.0026 g (0.002%) | S |
| 166 | Rapa = 203.1 mg (2.025%)<br>F68 = 30.3 mg (0.303%)<br>Sterile Water = 9792.6 mg (97.672%) | SP |
| 167 | Rapa = 201.4 mg (2.0005%)<br>Tween 20 = 43.9 mg (0.436%)<br>Sterile Water = 9822.8 mg (97.564%) | SP |
| 168 | EtOH = 0.8301 g (4.144%)<br>PEG 400 = 19.2014 g (95.856%) | S |
| 169 | Form. # 168 = 300 μl | S |
| 170 | Form. # 168 = 250 μl<br>Form. # 168 = 50 μl | S |
| 171 | Form. # 168 = 200 μl<br>Form. # 154 = 100 μl | S |
| 172 | Form. # 168 = 150 μl<br>Form. # 154 = 150 μl | S |
| 173 | Form. # 154 = 300 μl | S |
| 174 | Rapa = 102.2 mg (2.041%)<br>F68 = 16.0 mg (0.32%)<br>Sterile Water = 4889.0 mg (97.639%) | SP |
| 175 | Rapa = 101.1 mg (2.010%)<br>Tween 20 = 27.7 mg (0.551%)<br>Sterile Water = 4901.0 mg (97.439%) | SP |
| 176 | BSS+ = 0 μl<br>Sterile Water = 0 μl<br>Form. # 154 = 1000 μl | S |
| 177 | BSS+ = 200 μl<br>Sterile Water = 0 μl<br>Form. # 154 = 800 μl | SP |
| 178 | BSS+ = 400 μl<br>Form. # 154 = 600 μl | SP |
| 179 | BSS+ = 500 μl<br>Form. # 154 = 500 μl | SP |
| 180 | BSS+ = 600 μl<br>Form. # 154 = 400 μl | SP |
| 181 | BSS+ = 800 μl<br>Form. # 154 = 200 μl | SP |
| 182 | Sterile Water = 200 μl<br>Form. # 154 = 800 μl | SP |
| 183 | Sterile Water = 400 μl<br>Form. # 154 = 600 μl | SP |
| 184 | Sterile Water = 500 μl<br>Form. # 154 = 500 μl | SP |
| 185 | Sterile Water = 600 μl<br>Form. # 154 = 400 μl | SP |
| 186 | Sterile Water = 800 μl<br>Form. # 154 = 200 μl | SP |
| 187 | BSS+ = 2536.9 mg (49.98%)<br>Form. # 154 = 2538.7 mg (50.02%) | SP |
| 188 | Sterile Water = 2515.6 mg (49.84%)<br>Form. # 154 = 2532.2 mg (50.16%) | SP |
| 189 | F68 = 12.6 mg (0.25%)<br>Sterile Water = 2524.7 mg (49.79%)<br>Form. # 154 = 2533.1 mg (49.96%) | SP |
| 190 | Rapa = 2.0225 g (2%)<br>EtOH = 3.65 g (4%)<br>PEG 400 = 94.0 g (94%)<br>BHT = 0.002 g (0.002%) | S |
| 191 | F68 = 12.1 mg<br>Sterile Water = 2558.9 mg<br>Form. # 154 = 2556.4 mg | SP |
| 192 | F68 = 19.8 mg<br>Sterile Water = 2564.1 mg<br>Form. # 154 = 25557.5 mg | SP |
| 193 | F68 = 25.3 mg<br>Sterile Water = 2575.1 mg<br>Form. # 154 = 2572.9 mg | SP |
| 194 | F68 = 32.4 mg<br>Sterile Water = 2572.1 mg<br>Form. # 154 = 2562.1 mg | SP |
| 195 | F68 = 38.3 mg<br>Sterile Water = 2563.2 mg<br>Form. # 154 = 2573.5 mg | SP |
| 196 | F68 = 43.6 mg<br>Sterile Water = 2541.1 mg<br>Form. # 154 = 2556.0 mg | SP |
| 197 | F68 = 51.2 mg<br>Sterile Water = 2594.5 mg<br>Form. # 154 = 2594.1 mg | SP |
| 198 | PEG 400 = 1920 (96%)<br>EtOH = 80 g (4%) | S |
| 199 | Form. # 168 = 1000 μl | S |
| 200 | Form. # 168 = 200 μl<br>Form. # 154 = 800 μl | S |

TABLE 2-continued

| Form. # | Composition (mg), % (w/w) | Formulation Type |
|---|---|---|
| 201 | Form. # 168 = 400 µl<br>Form. # 154 = 600 µl | S |
| 202 | Form. # 168 = 500 µl<br>Form. # 154 = 500 µl | S |
| 203 | Form. # 168 = 600 µl<br>Form. # 154 = 400 µl | S |
| 204 | Form. # 168 = 800 µl<br>Form. # 154 = 200 µl | S |
| 205 | PEG 400 = 200 µl<br>Form. # 154 = 800 µl | S |
| 206 | PEG 400 = 400 µl<br>Form. # 154 = 600 µl | S |
| 207 | PEG 400 = 500 µl<br>Form. # 154 = 500 µl | S |
| 208 | PEG 400 = 600 µl<br>Form. # 154 = 400 µl | S |
| 209 | PEG 400 = 800 µl<br>Form. # 154 = 200 µl | S |
| 210 | Phosal 50PG = 6735.0 mg (99.002%)<br>Tween 80 = 67.9 mg (0.998%) | S |
| 211 | Rapa = 0 2.0047 g (2%)<br>EtOH = 4.00 g (4%)<br>PEG 400 = 94.05 g (94%) | S |
| 212 | Phosal 50PG = 20.0662 g (98.999%)<br>Tween 80 = 0.2029 g (1.001%) | S |
| 213 | Form. # 154 = 100 µl<br>Form. # 168 = 900 µl | S |
| 214 | Form. # 154 = 100 µl<br>Form. # 168 = 900 µl | S |
| 215 | Form. # 154 = 100 µl<br>Form. # 168 = 900 µl | S |
| 216 | Form. # 154 = 100 µl<br>PEG 400 = 900 µl | S |
| 217 | Form. # 154 = 100 µl<br>PEG 400 = 900 µl | S |
| 218 | Form. # 154 = 100 µl<br>PEG 400 = 900 µl | S |
| 219 | Form. # 154 = 100 µl<br>BSS+ = 900 µl | SP |
| 220 | Form. # 154 = 100 µl<br>BSS+ = 900 µl | SP |
| 221 | Form. # 154 = 100 µl<br>BSS+ = 900 µl | SP |
| 222 | Form. # 154 = 1000 µl | S |
| 223 | Form. # 154 = 1000 µl | S |
| 224 | Form. # 154 = 100 µl<br>Form. # 168 = 900 µl | S |
| 225 | Form. # 154 = 100 µl<br>Form. # 168 = 900 µl | S |
| 226 | Form. # 154 = 100 µl<br>Form. # 168 = 900 µl | S |
| 227 | Form. # 154 = 100 µl<br>PEG 400 = 900 µl | S |
| 228 | Form. # 154 = 100 µl<br>PEG 400 = 900 µl | S |
| 229 | Form. # 154 = 100 µl<br>PEG 400 = 900 µl | S |
| 230 | Form. # 154 = 100 µl<br>BSS+ = 900 µl | SP |
| 231 | Form. # 154 = µl<br>BSS+ = 900 µl | SP |
| 232 | Form. # 154 = 100 µl<br>BSS+ = 900 µl | SP |
| 233 | Form. # 154 = 200 µl<br>Form. # 168 = 800 µl | S |
| 234 | Form. # 154 = 200 µl<br>Form. # 168 = 800 µl | S |
| 235 | Form. # 154 = 200 µl<br>Form. # 168 = 800 µl | S |
| 236 | Form. # 154 = 200 µl<br>Form. # 168 = 800 µl | S |
| 237 | Form. # 154 = 200 µl<br>PEG 400 = 800 µl | S |
| 238 | Form. # 154 = 200 µl<br>PEG 400 = 800 µl | S |
| 239 | Form. # 154 = 200 µl<br>BSS+ = 800 µl | SP |
| 240 | Form. # 154 = 200 µl<br>BSS+ = 800 µl | SP |
| 241 | Form. # 154 = 200 µl<br>BSS+ = 800 µl | SP |
| 242 | Form. # 154 = 100 µl<br>Form. # 168 = 900 µl | S |
| 243 | Form. # 154 = 100 µl<br>PEG 400 = 900 µl | S |
| 244 | Form. # 154 = 100 µl<br>BSS+ = 900 µl | SP |
| 245 | Form. # 154 = 100 µl<br>BSS+/CMC (0.5%) = 900 µl | SP |
| 246 | Form. # 154 = 400 µl<br>Form. # 168 = 900 µl | S |
| 247 | Form. # 154 = 400 µl<br>PEG 400 = 900 µl | S |
| 248 | Form. # 154 = 400 µl<br>BSS+ = 900 µl | SP |
| 249 | Form. # 154 = 400 µl<br>BSS+/CMC (0.5%) = 900 µl | SP |
| 250 | Form. # 154 = 100 µl<br>BSS+/CMC (0.5%) = 900 µl | SP |
| 251 | Form. # 154 = 100 µl<br>BSS+/CMC (0.5%) = 900 µl | SP |
| 252 | Form. # 154 = 100 µl<br>BSS+/ CMC (0.5%) = 900 µl | SP |
| 253 | Form. # 154 = 200 µl<br>BSS+/CMC (0.5%) = 800 µl | SP |
| 254 | Form. # 154 = 200 µl<br>BSS+/CMC (0.5%) = 800 µl | SP |
| 255 | Form. # 154 = 200 µl<br>BSS+/CMC (0.5%) = 800 µl | SP |
| 256 | Form. # 154 = 400 µl<br>BSS+/CMC (0.5%) = 900 µl | SP |
| 257 | Form. # 154 = 400 µl<br>BSS+/CMC (0.5%) = 900 µl | SP |
| 258 | Form. # 154 = 400 µl<br>BSS+/CMC (0.5%) = 900 µl | SP |
| 259 | EtOH = 17.1 mg (0.57%)<br>PEG 400 = 2997.3 mg (99.43%) | S |
| 260 | EtOH = 40.8 mg (1.35%)<br>PEG 400 = 2980.2 mg (98.65%) | S |
| 261 | EtOH = 47.1 mg (1.57%)<br>PEG 400 = 2950.1 mg (98.43%) | S |
| 262 | Rapa = 2.0032 g (2%)<br>EtOH = 3.92 g (4%)<br>PEG 400 = 94.00 g (94%) | S |
| 263 | Triamcinolone acetomide = 80.8 mg (4.04%)<br>PEG 400 = 1920.8 mg (95.96%) | SP |
| 264 | NFF-0007 filled in glove box | S |
| 265 | PEG 400 = 9.598 g (96%)<br>EtOH = 0.4052 (4%) | S |
| 266 | Triamcinolone acetomide = 42.2 mg (4.123%)<br>PEG 400 = 981.3 mg (95.877%) | SP |
| 267 | Phosal 50PG = 20.0783 g (99.00835%)<br>Tween 80 = 0.2011 g (0.99165%) | S |
| 268 | PEG 400 = 96.1 g (96%)<br>EtOH = 4.00 g (4%) | S |
| 269 | Rapa = 0.4001 g (2%)<br>EtOH = 0.80 g (4%)<br>PEG 400 = 18.8 g (94%) | S |
| 270 | Sterile Water = 9955.8 mg (99.27%)<br>CMC High visc. = 47.8 mg (0.48%)<br>Tween 80 = 25.4 mg (0.25%) | S |
| 271 | Sterile Water = 9947.5 mg (99.00%)<br>CMC Medium visc. = 75 mg (0.75%)<br>Tween 80 = 25.1 mg (0.25%) | S |
| 272 | Rapa = 41 mg (2.01%)<br>Form. # 270 = 2000 mg (97.99%) | SP |
| 273 | Rapa = 40.2 mg (1.97%)<br>MSF-03-172-07E = 2000 mg (98.03%) | SP |
| 274 | NMP (Pharmasolve ®) = 1280.5 mg (65.89%)<br>PLGA 75/25 = 662.9 mg (34.11%) | S |

TABLE 2-continued

| Form. # | Composition (mg), % (w/w) | Formulation Type |
|---|---|---|
| 275 | NMP (Pharmasolve ®) = 1573.3 mg (80.50%)<br>PLGA 75/25 = 381.0 mg (19.50%) | S |
| 276 | NMP (Pharmasolve ®) = 1009.7 mg 49.8%)<br>PLGA 75/25 = 1001.6 mg (50.20%) | S |
| 277 | Sterile Water = 14934.0 mg (99.25%)<br>CMC Medium visc. = 112.4 mg (0.75%) | S |
| 278 | Propylene Glycol = 1893.7 mg (93.85%)<br>EtOH = 83.8 mg (4.16%)<br>Rapa = 40.2 mg (1.99%) | S |
| 279 | Propylene Glycol = 1946.2 mg (95.68%)<br>Benzyl Alcohol = 47.1 mg (2.31%)<br>Rapa = 40.8 mg (2.01%) | S |
| 280 | PEG 300 = 1894.1 mg (93.74%)<br>EtOH = 40.1 mg (1.98%)<br>Rapa = 86.4 mg (4.28%) | S |
| 281 | PEG 300 = 1925.5 mg (95.88%)<br>EtOH = 39.8 mg (1.98%)<br>Rapa = 43.0 mg (2.14%) | S |
| 282 | Rapa = 100.6 mg (2.01%)<br>MSF-03-176-02 = 4910.8 mg (97.99%) | SP |
| 283 | Rapa = 11.5 mg (0.57%)<br>PEG 300 = 2012.5 mg (99.43%) | S |
| 284 | Rapa = 10.3 mg (0.51%)<br>PEG 400 = 2017.2 mg (99.49%) | S |
| 285 | Rapa = 9.8 mg (0.486%)<br>PEG 600 = 2005.9 mg (99.51%) | S |
| 286 | Tacrolimus = 42.7 mg (2.11%)<br>EtOH = 46.0 mg (2.27%)<br>PG = 1938.7 mg (95.62%) | S |
| 287 | Tacrolimus = 40.7 mg (2.01%)<br>EtOH = 43.0 mg (2.12%)<br>PEG 300 = 1942.1 mg (95.87%) | S |
| 288 | Tacrolimus = 40.3 mg (1.99%)<br>EtOH = 43.8 mg (2.16%)<br>PEG 400 = 1942.3 mg (95.85%) | S |
| 289 | Tacrolimus = 40.8 mg (2.03%)<br>EtOH = 44.5 mg (2.21%)<br>PEG 600 = 1924.0 mg (95.76%) | S |
| 290 | Rapa = 61.0 mg (3.17%)<br>NMP = 1226.54 mg (63.80%)<br>PLGA 75/25 = 634.96 mg (33.03%) | S |
| 291 | Rapa = 100.2 mg (5.13%)<br>NMP = 1492.95 mg mg (76.37%)<br>PLGA 75/25 = 361.65 mg (18.50%) | S |
| 292 | Rapa = 62.9 mg (3.04%)<br>NMP = 1103.8 g mg (53.40%)<br>PLGA 75/25 = 900.2 mg (43.56%) | S |
| 293 | Rapa = 62.4 mg (3.00%)<br>NMP = 1205.1 mg mg (58.11%)<br>PLGA 75/25 = 806.4 mg (38.89%) | S |
| 294 | Sterile Water + 1% CMC Med. = 4909.1 mg (97.99%)<br>Rapa = 100.5 mg (2.01%) | SP |
| 295 | Sterile Water + 1% CMC high. = 4903.8 mg (97.96%)<br>Rapa = 101.9 mg (2.04%) | SP |
| 296 | Rapa = 40.5 mg (2.03%)<br>NMP = 1958.7 mg (97.97%) | S |
| 297 | Rapa = 20.5 mg (2.0%)<br>DMA = 41.4 mg (4.0%)<br>PVP = 35.0 mg (3.4%)<br>H2O = 934.7 mg (90.6%) | SP |
| 298 | Rapa = 10.6 mg (2.0%)<br>DMA = 10.6 mg (2.0%)<br>PEG 400 = 506.1 mg (96%) | S |
| 299 | Rapa = 5.2 mg (2.0%)<br>1% DMA in PEG 400 = 257.4 mg (98%) | SP |
| 300 | Rapa = 20.0 mg (2.0%)<br>DMA = 7.8 mg (0.8%)<br>PEG 400 = 974 mg (97.2%) | S |
| 301 | Rapa = 20.1 mg (1.3%)<br>DMA = 19.5 mg (1.3%)<br>PEG 400 = 1449.6 mg (97.3%) | S |
| 302 | Rapa = 20.0 mg (2.0%)<br>PVP = 10.8 mg (1.1%)<br>PEG 400 = 994.5 mg (97.0%) | SP |
| 303 | Rapa = 20.4 mg (2.0%)<br>PVP = 24.5 mg (2.4%)<br>PEG 400 = 990.7 mg (95.7%) | SP |
| 304 | Rapa = 25.5 mg (2.4%)<br>PVP = 51.9 mg (4.8%)<br>PEG 400 = 1000.6 mg (92.8%) | SP |
| 305 | Rapa = 22.5 mg (2.3%)<br>BA = 27.5 mg (2.7%)<br>PEG 400 = 950.7 mg (95.0%) | S |
| 306 | Rapa = 30.2 mg (2.3%)<br>PVP = 240.9 mg (18.6%)<br>PEG 400 = 1021.2 mg (79.0%) | SP |
| 307 | Rapa = 8.7 mg (3.1%)<br>1% PVP in H2O = 273 mg (96.9%) | SP |
| 308 | Rapa = 12.6 mg (2.53%)<br>5% PVP in H2O = 501.6 mg (97.5%) | SP |
| 309 | Rapa = 20.3 mg (3.8%)<br>10% PVP in H2O = 513.9 mg (96.2%) | SP |
| 310 | Rapa = 100.5 mg (2.0%)<br>DMA = 67.8 mg (1.4%)<br>PEG 400 = 4838.3 mg (96.6%) | S |
| 311 | Rapa = 96.8 mg (1.9%)<br>BA = 157.5 mg (3.2%)<br>PEG 400 = 4748.7 mg (94.9%) | S |
| 312 | Rapa = 105.8 mg (2.1%)<br>DMA = 5.63 mg (0.1%)<br>PEG 400 = 4888.9 mg (97.8%) | S |
| 313 | Rapa = 20.2 mg (2.0%)<br>PVP = 99.2 mg (9.9%)<br>H2O = 882.3 mg (88.1%) | SP |
| 314 | Rapa = 100.3 mg (2.0%)<br>PVP = 251.4 mg (5.0%)<br>H2O = 4662.8 mg (93.0%) | SP |
| 315 | Rapa = 20.3 mg (2.0%)<br>DMA = 983.9 mg (98%) | S |
| 316 | Triamcinolone = 22.8 mg (2.0%)<br>DMA = 12.0 mg (1.1%)<br>PEG 400 = 1104.5 mg (96.9%) | S |
| 317 | Triamcinolone = 1.0 mg (0.1%)<br>EtOH = 49.30 mg (4.0%)<br>PEG 400 = 1191.9 mg (96.0%) | S |
| 318 | Triamcinolone = 18.7 mg (0.9%)<br>PEG 400 = 959.8 mg (99.1%) | S |
| 319 | Triamcinolone = 25.5 mg (1.3%)<br>EtOH = 83.0 mg (4.1%)<br>PEG 400 = 1905.6 mg (94.6%) | S |
| 320 | Dexamethasone = 20.4 mg (1.2%)<br>EtOH = 71.7 mg (4.1%)<br>PEG 400 = 1737.6 mg (98.8%) | S |
| 321 | Dexamethasone = 27.5 mg (2.0%)<br>DMA = 5.6 mg (0.4%)<br>PEG 400 = 1347.3 mg (97.6%) | S |
| 322 | Rapa = 9.1 mg (0.152%)<br>EtOH = 90.9 mg (1.514%)<br>F127 = 262.8 mg (4.378%)<br>Water = 1489.1 mg (24.804%)<br>Sesame oil = 4151.5 mg (69.152%) | E |
| 323 | Rapa = 24.4 mg (0.625%)<br>Phosal 50PG = 203.1 mg (5.201%)<br>EtOH = 166.8 mg (4.272%)<br>Labrafac CC = 1502.8 mg (38.486%)<br>Sesame oil = 2007.7 mg (51.416%) | E |
| 324 | Form. # 174 with 2 mm beads | SP |
| 325 | Form. # 175 with 2 mm beads | SP |
| 326 | Rapa = 51 mg (1.47%)<br>EtOH = 407.7 mg (11.77%)<br>Cremophor EL = 1502.9 mg (43.44%)<br>Capmul PG8 = 1502.9 mg (43.44%) | SEF |

TABLE 2-continued

| Form. # | Composition (mg), % (w/w) | Formulation Type | |
|---|---|---|---|
| 327 | Rapa = 60.1 mg (1.956%)<br>EtOH = 125.0 mg (4.067%)<br>Caprol MPGO = 1444.1 mg (46.989%)<br>Softigen 767 = 1444.1 mg (46.989%) | SEF | 5 |

TABLE 3

| | Oxygen Sparged Time (min) | Head-space Gas | % $O_2$ 24 Hours after Treament | | | | 1 Week Stability % SRL (FS) | | 2 Week Stability % SRL (FS) | | 1 Month Stability % SRL (FS) | | 2 Month Stability % SRL (FS) | |
|---|---|---|---|---|---|---|---|---|---|---|---|---|---|---|
| | | | Head space | | Sample | | | | | | | | | |
| | | | Ave | Stdev | Ave | Stdev | Ave | Stdev | Ave | Stdev | Ave | Stdev | Ave | Stdev |
| 1 | 0 (no $O_2$ sparging) | $N_2$ | 0.8 | 0.5 | 15.5 | 1.0 | 99 | 0 | — | | 96 | 1 | 94 | 0 |
| 2 | 0.08 (5 sec) | $N_2$ | 1.3 | 0.5 | 15.4 | 0.9 | 100 | 1 | — | | 96 | 0 | 94 | 0 |
| 3 | 0.33 (20 sec) | $N_2$ | 2.2 | 0.3 | 15.7 | 0.6 | 100 | 1 | — | | 96 | 0 | 96 | 2 |
| 4 | 1 | $N_2$ | 3.0 | 0.1 | 18.7 | 0.1 | 98 | 0 | 97 | 1 | 96 | 0 | 95 | 0 |
| 5 | 3 | $N_2$ | 3.1 | 0.0 | 17.7 | 1.0 | 99 | 0 | 98 | 0 | 96 | 1 | — | |
| 6 | 10 | $N_2$ | 3.5 | 0.5 | 16.6 | 1.2 | 101 | 0 | 99 | 1 | 98 | 0 | — | |
| 7 | 30 | $N_2$ | 3.9 | 0.6 | 17.7 | 0.2 | 101 | 0 | 99 | 0 | 98 | 0 | — | |
| 8 | 0 (no $O_2$ sparging) | Air | 20.4 | 0.1 | 17.0 | 0.1 | 97 | 1 | 93 | 0 | 86 | 0 | 82 | 0 |
| 9 | 1 | Air | 21.8 | — | 21.5 | — | 98 | 0 | 93 | 0 | 82 | 1 | — | |
| 10 | 3 | Air | 21.6 | — | 20.6 | — | 101 | 1 | 95 | 3 | 81 | 1 | — | |
| 11 | 10 | Air | 20.7 | — | 19.6 | — | 99 | 1 | 93 | 0 | 82 | 1 | — | |
| 12 | 30 | Air | 20.6 | 0.5 | 19.0 | 1.1 | 101 | 0 | 93 | 1 | 81 | 2 | — | |
| 13 | 0 (no $O_2$ sparging) | $O_2$ | 84.2 | — | 28.1 | — | 95 | 0 | 83 | 1 | 59 | 2 | | |

TABLE 4

| | 25 C. | | | 5 C. | | −20 C. | |
|---|---|---|---|---|---|---|---|
| Fill volume | 0.5 mL | 1 mL | 2 mL | 0.5 mL | 2 mL | 0.5 mL | 2 mL |
| Headspace/Fill volume | HS/FV = 4 | HS/FV = 1.5 | HS/FV = 0.25 | HS/FV = 4 | HS/FV = 0.25 | HS/FV = 4 | HS/FV = 0.25 |
| µL $O_2$/mg of rapamycin | 1.45 µL $O_2$/ mg of rapamycin | 0.55 µL $O_2$/ mg of rapamycin | 0.09 µL $O_2$ /mg of rapamycin | 1.45 µL $O_2$/mg of rapamycin | 0.09 µL $O_2$/ mg of rapamycin | 1.45 µL $O_2$ /mg of rapamycin | 0.09 µL $O_2$/ mg of rapamycin |
| Time (months) | % FS | % FS | % FS | Time (months) | % FS | % FS | % FS |
| 0 | 98.23 | 99.00 | 96.00 | 0.00 | 98.23 | 96.00 | 98.23 | 96.00 |
| 1 | 86.67 | 96.00 | 91.40 | 1.00 | 97.02 | 95.22 | 98.21 | 95.05 |
| 2 | 82.43 | 94.00 | | 3.00 | 97.71 | 93.7 | 98.4 | 94.81 |
| 3 | 82.04 | | 89.50 | 6.00 | 92.84 | 94.2 | 98.6 | 96.1 |
| | | | | 9.00 | 75.8 | 93.4 | 96.9 | 96.1 |
| | | | | 12.00 | 73.3 | 93.9 | 95.4 | 96.1 |

TABLE 5

| | 25 C. % oxygen in Headsapce | | |
|---|---|---|---|
| | 0.80% | 20.40% | 84.72% |
| | µL O₂/mg of rapamycin | | |
| Time (weeks) | 0.55 µL O₂/ mg of rapamycin % FS | 13.91 µL O₂/mg of rapamycin % FS | 57.76 µL O₂mg of rapamycin % FS |
| 0 | 99.00 | 99.00 | 99.00 |
| 1 | 99.00 | 97.00 | 95.00 |
| 2 | | 93.00 | 83.00 |
| 4 | 96.00 | 86.00 | 59.00 |
| 8 | 94.00 | 82.00 | |

What is claimed is:

1. A method of preparing a stable liquid formulation comprising rapamycin, polyethylene glycol and dissolved gases, wherein the method comprises reducing exposure of the rapamycin to one or more air components and placing the liquid formulation in a sealed vessel, wherein the method does not comprise addition of an antioxidant, and wherein the liquid formulation has a percent of oxygen in the dissolved gases of no greater than 20%, and the liquid formulation is in contact with a head space gas having no greater than 20% oxygen.

2. The method of claim 1, wherein the method comprises one or more of the techniques selected from the group consisting of: sparging one or more components of the liquid formulation with an inert gas, blanketing one or more components of the liquid formulation with an inert gas, having a ratio of the head space volume to liquid formulation volume no greater than 1.5, and having no greater than 1 µl of oxygen in the head space per milligram of the rapamycin in the liquid formulation.

3. The method of claim 1, wherein the one or more air components is oxygen.

4. The method of claim 2, wherein the inert gas is a noble gas.

5. The method of claim 4, wherein the noble gas is nitrogen.

6. The method of either of claims 4 or 5, wherein the method comprises blanketing one or more components of the liquid formulation with the inert gas and having a ratio of the head space volume to liquid formulation volume no greater than 1.5.

7. The method of claim 1, wherein the liquid formulation has a percent of oxygen in the dissolved gases of no greater than 17.5%.

8. The method of claim 1, wherein the liquid formulation has a percent of oxygen in the dissolved gases of no greater than 16.5%.

9. The method of claim 1, wherein the rapamycin in the liquid formulation is between 0.5% to 5.0% of the total weight of the liquid formulation.

10. The method of claim 1, wherein the head space gas has no greater than 10% oxygen gas.

11. The method of claim 1, wherein the head space gas has no greater than 5% oxygen gas.

12. The method of claim 1, further comprising surrounding the sealed vessel by a secondary packaging to reduce light to which the liquid formulation is exposed.

13. The method of claim 1, wherein the polyethylene glycol is between 90 to 99% of the total weight of the liquid formulation.

14. The method of claim 1, wherein the formula strength of the rapamycin is at least 90% for a period of at least 1 month at 25° C. and 60% relative humidity.

15. The method of claim 1, wherein the formula strength of the rapamycin is at least 90% for a period of at least 2 months at 25° C. and 60% relative humidity.

16. The method of claim 1, wherein the formula strength of the rapamycin is at least 90% for a period of at least 3 months at 25° C. and 60% relative humidity.

17. The method of claim 1, wherein the formula strength of the rapamycin is at least 90% for a period of at least about 3 months at 5° C.

18. The method of claim 1, wherein the formula strength of the rapamycin is at least 90% for a period of at least about 1 year at 5° C.

19. The method of claim 1, wherein the formula strength of the rapamycin is at least 90% for a period of at least 2 years at 5° C.

20. The method of claim 1, wherein the liquid formulation further comprises ethanol.

21. The method of claim 20, wherein the rapamycin is present at 2% w/w, the polyethylene glycol is PEG 400 and the PEG 400 is present at 94% w/w, and the ethanol is present at 4% w/w.

22. A method of preparing a stable liquid formulation comprising rapamycin, polyethylene glycol and dissolved gases, wherein the method comprises reducing exposure of the rapamycin to one or more air components and placing the liquid formulation in a sealed vessel, wherein the liquid formulation has a percent of oxygen in the dissolved gases of no greater than 20%, and the liquid formulation is in contact with a head space gas having no greater than 20% oxygen, and wherein the method does not comprise the addition of an antioxidant selected from the group consisting of ascorbic acid, citric acid, sodium sulfite, disodium EDTA, dithiothreitol (DTT), fumaric acid, beta hydroxyanisole (BHA), propyl gallate, alpha and beta tocopherols, toluene solfonic acid, tartaric acid, thioglycerol, thiourea, sodium formaldehyde sulfoxylate, sodium thiosulfate, glutamic acid, butylated hydroxytoluene (BHT), ascorbyl palmitate, benzyl alcohol, benzalkonium chloride, or maleic acid.

23. The method of claim 22, wherein the liquid formulation further comprises ethanol.

24. The method of claim 23, wherein the rapamycin is present at 2% w/w, the polyethylene glycol is PEG 400 and the PEG 400 is present at 94% w/w, and the ethanol is present at 4% w/w.

25. The method of claim 22, wherein the formula strength of the rapamycin in the liquid formulation is at least 90% for a period of at least 1 month at 25° C. and 60% relative humidity.

26. The method of claim 1, wherein
the rapamycin in the liquid formulation is between 0.5% to 5% of the total weight of the liquid formulation;
the polyethylene glycol is between 90 to 99% of the total weight of the liquid formulation;
the liquid formulation further comprises ethanol; and
the formula strength of the rapamycin is at least 90% for a period of at least 1 month at 25° C. and 60% relative humidity.

* * * * *